United States Patent
Hartman

(10) Patent No.: US 10,364,228 B2
(45) Date of Patent: Jul. 30, 2019

(54) AZEPANE DERIVATIVES AND METHODS OF TREATING HEPATITIS B INFECTIONS

(71) Applicant: Novira Therapeutics, Inc., Doylestown, PA (US)

(72) Inventor: George D. Hartman, Lansdale, PA (US)

(73) Assignee: NOVIRA THERAPEUTICS, INC., Doylestown, PA (US)

(*) Notice: Subject to any disclaimer, the term of this patent is extended or adjusted under 35 U.S.C. 154(b) by 42 days.

(21) Appl. No.: 15/671,499

(22) Filed: Aug. 8, 2017

(65) Prior Publication Data

US 2018/0044300 A1 Feb. 15, 2018

Related U.S. Application Data

(63) Continuation of application No. 14/801,126, filed on Jul. 16, 2015, now Pat. No. 9,758,489, which is a continuation of application No. 14/541,487, filed on Nov. 14, 2014, now Pat. No. 9,115,113.

(60) Provisional application No. 61/904,042, filed on Nov. 14, 2013.

(51) Int. Cl.
| | |
|---|---|
| C07D 243/08 | (2006.01) |
| C07D 471/08 | (2006.01) |
| C07D 487/08 | (2006.01) |
| C07D 401/14 | (2006.01) |
| C07D 401/04 | (2006.01) |
| A61K 31/551 | (2006.01) |
| A61K 31/55 | (2006.01) |
| A61K 31/5513 | (2006.01) |
| A61K 45/06 | (2006.01) |
| A61K 39/29 | (2006.01) |
| A61K 38/21 | (2006.01) |
| A61K 31/439 | (2006.01) |

(52) U.S. Cl.
CPC .......... *C07D 243/08* (2013.01); *A61K 31/439* (2013.01); *A61K 31/55* (2013.01); *A61K 31/551* (2013.01); *A61K 31/5513* (2013.01); *A61K 38/21* (2013.01); *A61K 39/292* (2013.01); *A61K 45/06* (2013.01); *C07D 401/04* (2013.01); *C07D 401/14* (2013.01); *C07D 471/08* (2013.01); *C07D 487/08* (2013.01)

(58) Field of Classification Search
None
See application file for complete search history.

(56) References Cited

U.S. PATENT DOCUMENTS

| | | |
|---|---|---|
| 9,115,113 B2 | 8/2015 | Hartman |
| 9,758,489 B2 | 9/2017 | Hartman |

FOREIGN PATENT DOCUMENTS

| | | | |
|---|---|---|---|
| WO | 2001/068640 A1 | 9/2001 | |
| WO | 2001/068641 A1 | 9/2001 | |
| WO | 2007/122411 A1 | 11/2007 | |
| WO | 2007122411 A1 | 11/2007 | |
| WO | WO-2007135427 A1 * | 11/2007 | ........... C07D 213/74 |
| WO | 2009/023059 A2 | 2/2009 | |
| WO | 2009023059 A2 | 2/2009 | |
| WO | 2013006394 A1 | 1/2013 | |
| WO | 2013096744 A1 | 6/2013 | |

OTHER PUBLICATIONS

Registry Entry 958693-85-1 on Dec. 19, 2007 (Year: 2007).*
Registry Entry 693776-85-1 on Jun. 16, 2004. (Year: 2004).*
Registry Entry 691882-00-5 on Jun. 11, 2004. (Year: 2004).*
Registry Entry 262293-90-3 on Apr. 18, 2000. (Year: 2000).*
Registry Entry 1188535-18-3 on Oct. 16, 2009. (Year: 2009).*
Registry Entry 1035142-16-5 on Jul. 22, 2008. (Year: 2008).*
Registry Entry 94855-68-4 on Nov. 16, 1984. (Year: 1984).*
U.S. Appl. No. 14/541,487, filed Nov. 14, 2014, 2015/0132258, May 14, 2015, U.S. Pat No. 9,115,113, Aug. 25, 2015, George D. Hartman.
U.S. Appl. No. 14/801,126, filed Jul. 16 2015, 2015/0315159, Nov. 5, 2015, U.S. Pat No. 9,758,489, Sep. 12, 2017, George D. Hartman.
RN 1413197-87-1 Registry, Database Registry [Online] Retrieved from STN, Dec. 10, 2012, Jul. 19, 2018.
RN 1413479-46-5 Registry, Database Registry [Online] Retrieved from STN, Dec. 11, 2012, Jul. 19, 2018.
RN 1413515-60-2 Registry, Database Registry [Online] Retrieved from STN, Dec. 11, 2012, Jul. 19, 2018.
RN 1394397-49-9 Registry, Database Registry [Online] Retrieved from STN, Sep. 17, 2012, Jul. 19, 2018.
RN 1413425-61-2 Registry, Database Registry [Online] Retrieved from STN, Dec. 10, 2012, Jul. 19, 2018.
RN 1413178-42-3 Registry, Database Registry [Online] Retrieved from STN, Dec. 10, 2012, Jul. 19, 2018.
RN 1422943-97-2 Registry, Database Registry [Online] Retrieved from STN, Mar. 11, 2013, Jul. 19, 2018.
RN 1567331-04-7 Registry, Database Registry [Online] Retrieved from STN, Mar. 12, 2014, Jul. 19, 2018.
[Online] Registry via STN, Nov. 3, 2013, RN 1422943-97-2 (via SciFinder search, pp. 1).
Xu et al. (2010) "Investigation of collision-induced dissociations involving odd-electron ion formation under positive electrospray ionization conditions using accurate mass," Rapid Communications in Mass Spectrometry. 24(3):321-327.
International Search Report with Written Opinion corresponding to International Patent Application No. PCT/US2014/065614, dated Feb. 2, 2014.
Examiner Search Results; STN International; Search Performed Nov. 22, 2016.

(Continued)

Primary Examiner — Jeffrey S Lundgren
Assistant Examiner — Michael J Schmitt
(74) Attorney, Agent, or Firm — Lathrop Gage LLP; Brian C. Trinque; Benjamin A. Vaughan

(57) ABSTRACT

Provided herein are compounds useful for the treatment of HBV infection in a subject in need thereof, pharmaceutical compositions thereof, and methods of inhibiting, suppressing, or preventing HBV infection in the subject.

18 Claims, No Drawings

(56) References Cited

OTHER PUBLICATIONS

[Online] Registry via CAS, Dec. 11, 2012, RN 1413515-60-2.
[Online] Registry via CAS, Dec. 11, 2012, RN 1413479-46-5.
[Online] Registry via CAS, Dec. 10, 2012, RN 1413425-61-2.
[Online] Registry via CAS, Dec. 10, 2012, RN 141197-87-1.
[Online] Registry via CAS, Dec. 10, 2012, RN 1413178-42-3.
[Online] Registry via CAS, Sep. 17, 2012, RN 1394397-49-9.
[Online] Registry via CAS, Nov. 21, 2007, RN 955378-31-1.
[Online] Registry via CAS, Nov. 21, 2007, RN 955378-30-0.
[Online] Registry via CAS, Nov. 21, 2007, RN 955378-29-7.
[Online] Registry via CAS, Nov. 21, 2007, RN 955378-28-6.
[Online] Registry via CAS, Nov. 21, 2007, RN 955378-26-4.
[Online] Registry via CAS, Nov. 21, 2007, RN 955378-24-2.
[Online] Registry via CAS, Nov. 21, 2007, RN 955378-17-3.
[Online] Registry via CAS, Nov. 21, 2007, RN 955378-16-2.
[Online] Registry via CAS, Nov. 21, 2007, RN 955378-08-2.
[Online] Registry via CAS, Jun. 16, 2004, RN 693776-93-1.
[Online] Registry via CAS, Jun. 16, 2004, RN 693776-91-9.

* cited by examiner

AZEPANE DERIVATIVES AND METHODS OF TREATING HEPATITIS B INFECTIONS

RELATED APPLICATIONS

This application is a continuation of U.S. Nonprovisional application Ser. No. 14/801,126, filed Jul. 16, 2015 which is a continuation of U.S. Nonprovisional application Ser. No. 14/541,487, filed Nov. 14, 2014, now U.S. Pat. No. 9,115,113 issued on Aug. 25, 2015 which claims priority to U.S. Provisional Application No. 61/904,042, filed Nov. 14, 2013. The entire contents of these applications are incorporated herein by reference.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in a subject in need thereof.

Accordingly, in an aspect, provided herein are compounds of Formula I:

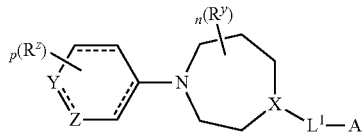

or a pharmaceutically acceptable salt thereof.

In another aspect, provided herein are compounds of Formula Ia:

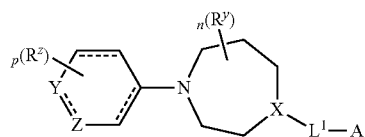

or a pharmaceutically acceptable salt thereof.

In another aspect, provided herein are compounds of Formula II:

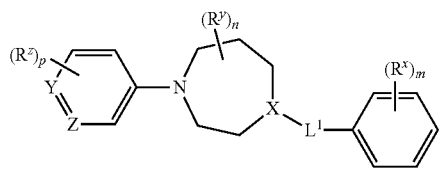

or a pharmaceutically acceptable salt thereof.

In another aspect, provided herein are compounds of Formula IIa:

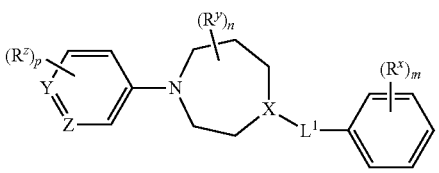

or a pharmaceutically acceptable salt thereof.

In an embodiment, compounds of Formula II, or a pharmaceutically acceptable salt thereof, have the Formula III:

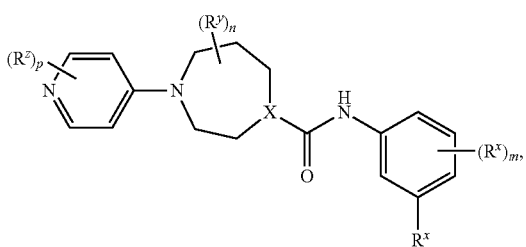

wherein m is 0, 1, or 2.

In a further embodiment, compounds of Formula II, or a pharmaceutically acceptable salt thereof, have the Formula IV:

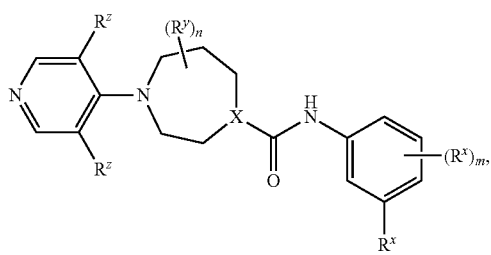

wherein m is 0, 1, or 2.

In another aspect, provided herein are compounds of Formula V:

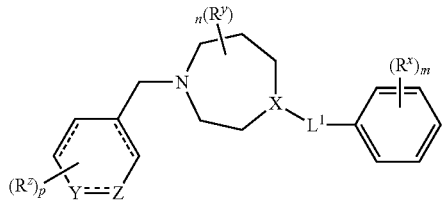

or a pharmaceutically acceptable salt thereof.

In another aspect, provided herein are pharmaceutical compositions comprising a compound of the invention, or a pharmaceutically acceptable salt thereof, together with a pharmaceutically acceptable carrier.

In one aspect, provided herein is a method of treating an HBV infection in an individual in need thereof, comprising administering to the individual a therapeutically effective amount of the compound of the invention.

In another aspect, provided herein is a method of eradicating an HBV infection in an individual in need thereof, comprising administering to the individual a therapeutically effective amount of a compound of the invention.

In another aspect, provided herein is a method of reducing viral load associated with an HBV infection in an individual in need thereof, comprising administering to the individual a therapeutically effective amount of a compound of the invention.

In still another aspect, provided herein is a method of reducing reoccurrence of an HBV infection in an individual in need thereof, comprising administering to the individual a therapeutically effective amount of a compound of the invention.

In yet another aspect, provided herein is a method of reducing an adverse physiological impact of an HBV infection in an individual in need thereof, comprising administering to the individual a therapeutically effective amount of a compound of the invention.

Also provided herein are methods of inducing remission of hepatic injury from an HBV infection in an individual in need thereof, comprising administering to the individual a therapeutically effective amount of a compound of the invention.

In another aspect, provided herein is a method of reducing the physiological impact of long-term antiviral therapy for HBV infection in an individual in need thereof, comprising administering to the individual a therapeutically effective amount of a compound of the invention.

In another aspect, provided herein is a method of prophylactically treating an HBV infection in an individual in need thereof, wherein the individual is afflicted with a latent HBV infection, comprising administering to the individual a therapeutically effective amount of a compound of the invention.

Any of the above methods may further comprise administration to the individual at least one additional therapeutic agent. In an embodiment, the additional therapeutic agent may be selected from, but not limited to, the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, an HBV vaccine, and agents of distinct or unknown mechanism, and a combination thereof.

Any of the above methods may further comprise administration to the individual at least one additional therapeutic agent. In an embodiment, the additional therapeutic agent is selected from the group consisting of a HBV polymerase inhibitor, interferon, viral entry inhibitor, viral maturation inhibitor, literature-described capsid assembly modulator, reverse transcriptase inhibitor, a TLR-agonist, and agents of distinct or unknown mechanism, and a combination thereof.

In another embodiment, the additional therapeutic agent is a reverse transcriptase inhibitor and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the additional therapeutic agent is a TLR agonist. In a preferred embodiment, the TLR agonist is a TLR-7 agonist selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl) phenyl]acetate).

In a further embodiment of the combination therapy, the additional therapeutic agent is an interferon, wherein the interferon is any interferon, which may be optionally pegylated. In yet a further embodiment, the interferon is interferon alpha (IFN-α), interferon beta (IFN-β), interferon lambda (IFN-λ), or interferon gamma (IFN-γ). In a preferred embodiment, the interferon is interferon-alpha-2a, interferon-alpha-2b, interferon-alpha-n1, pegylated interferon-alpha-2a, or pegylated interferon-alpha-2b.

In any of the methods provided herein, the method may further comprise administering to the individual at least one HBV vaccine, a nucleoside HBV inhibitor, or any combination thereof. In an embodiment, the HBV vaccine is at least one of Recombivax HB, Engerix-B, Elovac B, GeneVac-B, or Shanvac B.

In another embodiment of the methods provided herein, the compound of the invention allows for administering of the at least one additional therapeutic agent at a lower dose or frequency as compared to the administering of the at least one additional therapeutic agent alone that is required to achieve similar results in prophylactically treating an HBV infection in an individual in need thereof.

In another embodiment of the methods provided herein, administering of the compound of the invention reduces the viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In another embodiment of the methods provided herein, administering of the compound of the invention reduces the viral load in the individual to a greater extent or at a faster rate compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In another embodiment of the methods provided herein, the administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another aspect, provided herein is a method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. In an embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine In another embodiment of the methods provided herein, the method further comprises monitoring the HBV viral load, and wherein the method is carried out for a period of time such that the HBV virus is undetectable.

DETAILED DESCRIPTION OF THE INVENTION

Provided herein are compounds that are useful in the treatment and prevention of HBV infection in man. In a non-limiting aspect, these compounds can modulate and/or disrupt HBV assembly and other HBV core protein functions necessary for the generation of infectious particles by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly and function of core protein have been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly inhibitors may elicit lower drug resistance emergence rates relative to existing HBV antivirals. Further, drug therapy that targets HBV capsid could be less prone to drug-resistant mutations when compared to drugs that target traditional NA enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit or disrupt) the activity, stability, function, and viral replication properties of HBV cccDNA. In yet another embodiment, the compounds of the invention can be used in methods of diminishing or preventing the formation of HBV cccDNA.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "literature-described capsid assembly modulator" refers a capsid assembly modulator that is not a compound of the present invention.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_{1-6})$alkyl, particularly ethyl, methyl, isopropyl, isobutyl, n-pentyl, n-hexyl and cyclopropylmethyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_{3-10}$ cycloalkyl), or groups having 3 to 7 ring atoms ($C_{3-7}$ cycloalkyl). Illustrative examples of cycloalkyl groups include, but are not limited to, the following moieties:

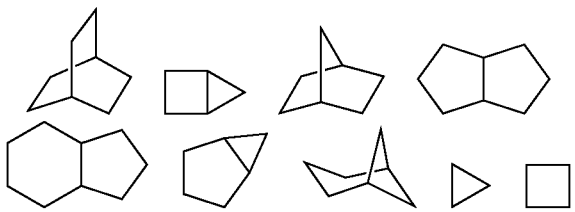

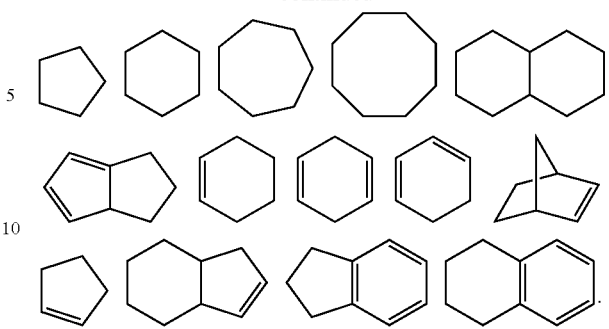

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

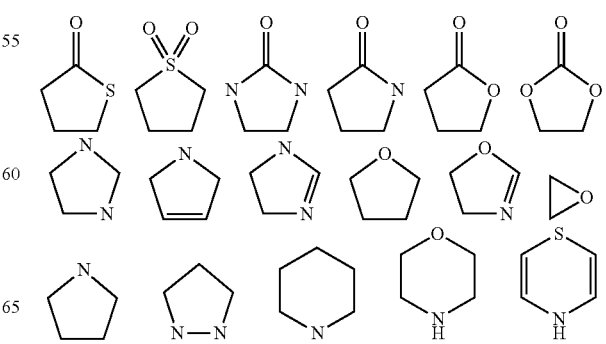

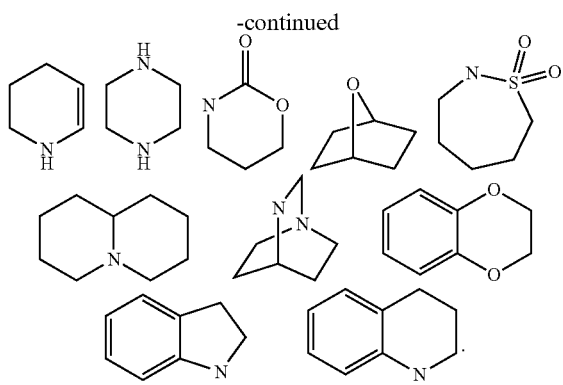

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "heteroaryl" or "heteroaromatic" refers to a heterocycle having aromatic character. A polycyclic heteroaryl may include one or more rings that are partially saturated. Examples include the following moieties:

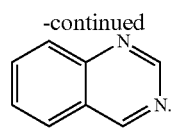

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthenyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

Compounds of the Invention

The present invention relates to the discovery of compounds that are useful in the treatment and prevention of HBV infection in man. In one aspect, the compounds of the invention are useful in HBV treatment by disrupting, accelerating, reducing delaying and/or inhibiting normal viral capsid assembly and/or disassembly of immature or mature particles, thereby inducing aberrant capsid morphology and leading to antiviral effects such as disruption of virion assembly and/or disassembly and/or virion maturation, and/or virus egress.

In another aspect, compounds of the invention bind to core protein thereby inducing aberrant virion and leading to antiviral effects such as disruption of virion assembly, disassembly, maturation, or virus egress.

The capsid assembly disruptors disclosed herein may be used as monotherapy and/or in cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, NA drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein function or degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention can be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

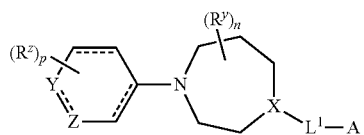

I or a pharmaceutically acceptable salt thereof, wherein a ═══ line denotes an optionally double bond;

X is C or N;

one of Y or Z is N, and the other is C;

$L^1$ is —C(O)NR$^1$—, —SO$_2$NR$^1$—, —C(O)—, —C(O)O—, or —SO$_2$—;

A is $C_{1-6}$ alkyl, -(L$^2$)$_q$-OR$^3$, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl), wherein A is optionally substituted with one or more occurrences of R$^x$;

R$^x$ is independently, at each occurrence, halo, —CN, —NO$_2$, —$C_{1-6}$ haloalkyl, —$C_{1-6}$ dihaloalkyl, —$C_{1-6}$ trihaloalkyl, -(L$^2$)$_q$-C(═O)R$^2$, -(L$^2$)$_q$CO$_2$R$^3$, or -(L$^2$)$_q$-C(═O)N(R$^3$)$_2$;

R$^y$ is independently, at each occurrence, $C_{1-6}$ alkyl, halo, —CN, —NO$_2$, -(L$^2$)$_q$-OR$^3$, -(L$^2$)$_q$-SR$^2$, -(L$^2$)$_q$-S(═O)R$^2$, -(L$^2$)$_q$-S(═O)$_2$R$^2$, -(L$^2$)$_q$-NHS(═O)$_2$R$^2$, -(L$^2$)$_q$-C(═O)R$^2$, -(L$^2$)$_q$-OC(═O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(═O)N(R$^3$)$_2$, -(L$^2$)$_q$-OC(═O)N(R$^3$)$_2$, -(L$^2$)$_q$-NHC(═O)NH(R$^3$), -(L$^2$)$_q$-NHC(═O)R$^2$, -(L$^2$)$_q$-NHC(═O)OR$^2$, -(L$^2$)$_q$-C(OH)(R$^3$)$_2$, -(L$^2$)$_q$C(NH$_2$)(R$^3$)$_2$, —$C_{1-6}$ haloalkyl, —$C_{1-6}$ dihaloalkyl, —$C_{1-6}$ trihaloalkyl, $C_{3-7}$ cycloalkyl, a $C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

or:

two R$^y$ groups on adjacent carbon atoms are taken together to form a fused ring; or two R$^y$ groups on non-adjacent carbon atoms are taken together to form a bridge of a bridged bicyclic group; or two R$^y$ groups on the same carbon atom, together with that carbon atom, form C(O);

R$^z$ is independently, at each occurrence, $C_{1-6}$ alkyl, halo, —CN, —NO$_2$, -(L$^2$)$_q$-OR$^3$, -(L$^2$)$_q$-SR$^2$, -(L$^2$)$_q$-S(═O)R$^2$, -(L$^2$)$_q$-S(═O)$_2$R$^2$, -(L$^2$)$_q$-NHS(═O)$_2$R$^2$, -(L$^2$)$_q$-C(═O)R$^2$, -(L$^2$)$_q$-OC(═O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(═O)N(R$^3$)$_2$, -(L$^2$)$_q$-OC(═O)N(R$^3$)$_2$, -(L$^2$)$_q$-NHC(═O)NH(R$^3$), -(L$^2$)$_q$-NHC(═O)R$^2$, -(L$^2$)$_q$-NHC(═O)OR$^2$, -(L$^2$)$_q$-C(OH)(R$^3$)$_2$, -(L$^2$)$_q$C(NH$_2$)(R$^3$)$_2$, —$C_{1-6}$ haloalkyl, —$C_{1-6}$ dihaloalkyl, —$C_{1-6}$ trihaloalkyl, $C_{3-7}$ cycloalkyl, a $C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

$L^2$ is independently, at each occurrence, a bivalent radical selected from —($C_{1-3}$ alkylene)-, —($C_{3-7}$ cycloalkylene)-, —($C_{1-3}$ alkylene)$_q$-O—($C_{1-3}$ alkylene)-, or —($C_{1-3}$ alkylene)$_q$-NH—($C_{1-3}$ alkylene)$_q$-;

R$^1$ is H or $C_{1-6}$-alkyl;

R$^2$ is $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

each R$^3$ is independently, at each occurrence, H, $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

n is 0, 1, 2, or 3;

p is 1, 2, or 3; and q is 0 or 1.

In an embodiment of Formula I, ═══ denotes a double bond.

In another aspect, the compound of the invention is a compound of Formula Ia:

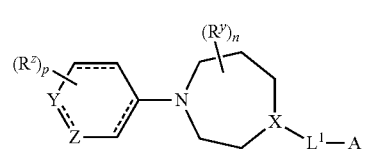

Ia or a pharmaceutically acceptable salt thereof, wherein
a ⸺ line denotes an optionally double bond;
X is C or N;
each Y and Z are independently selected from N and C;
$L^1$ is —C(O)NR$^1$—, —SO$_2$NR$^1$—, —C(O)—, —C(O)O—, C$_{1-4}$ alkyl, or —SO$_2$—;
A is C$_{1-6}$ alkyl, -(L$^2$)$_q$-OR$^3$, C$_{3-10}$ cycloalkyl, C$_{3-10}$ heterocycloalkyl, aryl, heteroaryl, —C$_{1-4}$ alkylene-(C$_{3-10}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl), wherein A is optionally substituted with one or more occurrences of R$^x$;
R$^x$ is independently, at each occurrence, halo, —CN, —NO$_2$, —C$_{1-6}$ haloalkyl, —C$_{1-6}$ dihaloalkyl, —C$_{1-6}$ trihaloalkyl, -(L$^2$)$_q$-C(=O)R$^2$, -(L$^2$)$_q$CO$_2$R$^3$, or -(L$^2$)$_q$-C(=O)N(R$^3$)$_2$;
R$^y$ is independently, at each occurrence, C$_{1-6}$ alkyl, halo, —CN, —NO$_2$, -(L$^2$)$_q$-OR$^3$, -(L$^2$)$_q$-SR$^2$, -(L$^2$)$_q$-S(=O)R$^2$, -(L$^2$)$_q$-S(=O)$_2$R$^2$, -(L$^2$)$_q$-NHS(=O)$_2$R$^2$, -(L$^2$)$_q$-C(=O)R$^2$, -(L$^2$)$_q$-OC(=O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(=O)N(R$^3$)$_2$, -(L$^2$)$_q$-OC(=O)N(R$^3$)$_2$, -(L$^2$)$_q$-NHC(=O)NH(R$^3$), -(L$^2$)$_q$-NHC(=O)R$^2$, -(L$^2$)$_q$-NHC(=O)OR$^2$, -(L$^2$)$_q$-C(OH)(R$^3$)$_2$, -(L$^2$)$_q$C(NH$_2$)(R$^3$)$_2$, —C$_{1-6}$ haloalkyl, —C$_{1-6}$ dihaloalkyl, —C$_{1-6}$ trihaloalkyl, C$_{3-7}$ cycloalkyl, a C$_{3-10}$ heterocycloalkyl, aryl, heteroaryl, —C$_{1-4}$ alkylene-(C$_{3-7}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
or:
two R$^y$ groups on adjacent carbon atoms are taken together to form a fused ring; or
two R$^y$ groups on non-adjacent carbon atoms are taken together to form a bridge of a bridged bicyclic group; or
two R$^y$ groups on the same carbon atom, together with that carbon atom, form C(O);
R$^z$ is independently, at each occurrence, C$_{1-6}$ alkyl, halo, —CN, —NO$_2$, -(L$^2$)$_q$-OR$^3$, -(L$^2$)$_q$-SR$^2$, -(L$^2$)$_q$-S(=O)R$^2$, -(L$^2$)$_q$-S(=O)$_2$R$^2$, -(L$^2$)$_q$-NHS(=O)$_2$R$^2$, -(L$^2$)$_q$-C(=O)R$^2$, -(L$^2$)$_q$-OC(=O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(=O)N(R$^3$)$_2$, -(L$^2$)$_q$-OC(=O)N(R$^3$)$_2$, -(L$^2$)$_q$-NHC(=O)NH(R$^3$), -(L$^2$)$_q$-NHC(=O)R$^2$, -(L$^2$)$_q$-NHC(=O)OR$^2$, -(L$^2$)$_q$-C(OH)(R$^3$)$_2$, -(L$^2$)$_q$C(NH$_2$)(R$^3$)$_2$, —C$_{1-6}$ haloalkyl, —C$_{1-6}$ dihaloalkyl, —C$_{1-6}$ trihaloalkyl, C$_{3-7}$ cycloalkyl, a C$_{3-10}$ heterocycloalkyl, aryl, heteroaryl, —C$_{1-4}$ alkylene-(C$_{3-7}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
L$^2$ is independently, at each occurrence, a bivalent radical selected from —(C$_{1-3}$ alkylene)-, —(C$_{3-7}$ cycloalkylene)-, —(C$_{1-3}$ alkylene)$_q$-O—(C$_{1-3}$ alkylene)-, or —(C$_{1-3}$ alkylene)$_q$-NH—(C$_{1-3}$ alkylene)$_q$-;
R$^1$ is H or C$_{1-6}$-alkyl;
R$^2$ is C$_{1-6}$ alkyl, —C$_{1-6}$ haloalkyl, —C$_{1-6}$ dihaloalkyl, —C$_{1-6}$ trihaloalkyl, C$_{3-10}$ cycloalkyl, C$_{3-10}$ heterocycloalkyl, aryl, heteroaryl, —C$_{1-4}$ alkylene-(C$_{3-10}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
each R$^3$ is independently, at each occurrence, H, C$_{1-6}$ alkyl, —C$_{1-6}$ haloalkyl, —C$_{1-6}$ dihaloalkyl, —C$_{1-6}$ trihaloalkyl, C$_{3-10}$ cycloalkyl, C$_{3-10}$ heterocycloalkyl, aryl, heteroaryl, —C$_{1-4}$ alkylene-(C$_{3-10}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
n is 0, 1, 2, or 3;
p is 1, 2, or 3; and
q is 0 or 1.

In an embodiment of Formula Ia, ⸺ denotes a double bond.

In another aspect, provided herein is a compound of Formula II:

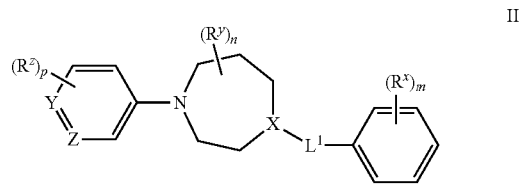

or a pharmaceutically acceptable salt thereof,
wherein:
X is C or N;
one of Y or Z is N, and the other is C;
$L^1$ is —C(O)NR$^1$—, —SO$_2$NR$^1$—, —C(O)—, —C(O)O—, or —SO$_2$—;
R$^x$ is independently, at each occurrence, halo, —CN, —NO$_2$, —C$_{1-6}$ haloalkyl, —C$_{1-6}$ dihaloalkyl, —C$_{1-6}$ trihaloalkyl, -(L$^2$)$_q$-C(=O)R$^2$, -(L$^2$)$_q$CO$_2$R$^3$, or -(L$^2$)$_q$-C(=O)N(R$^3$)$_2$;
R$^y$ is independently, at each occurrence, C$_{1-6}$ alkyl, halo, —CN, —NO$_2$, -(L$^2$)$_q$-OR$^3$, -(L$^2$)$_q$-SR$^2$, -(L$^2$)$_q$-S(=O)R$^2$, -(L$^2$)$_q$-S(=O)$_2$R$^2$, -(L$^2$)$_q$-NHS(=O)$_2$R$^2$, -(L$^2$)$_q$-C(=O)R$^2$, -(L$^2$)$_q$-OC(=O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(=O)N(R$^3$)$_2$, -(L$^2$)$_q$-OC(=O)N(R$^3$)$_2$, -(L$^2$)$_q$-NHC(=O)NH(R$^3$), -(L$^2$)$_q$-NHC(=O)R$^2$, -(L$^2$)$_q$-NHC(=O)OR$^2$, -(L$^2$)$_q$-C(OH)(R$^3$)$_2$, -(L$^2$)$_q$C(NH$_2$)(R$^3$)$_2$, —C$_{1-6}$ haloalkyl, —C$_{1-6}$ dihaloalkyl, —C$_{1-6}$ trihaloalkyl, C$_{3-7}$ cycloalkyl, a C$_{3-10}$ heterocycloalkyl, aryl, heteroaryl, —C$_{1-4}$ alkylene-(C$_{3-7}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
or:
two R$^y$ groups on adjacent carbon atoms are taken together to form a fused ring; or
two R$^y$ groups on non-adjacent carbon atoms are taken together to form a bridge of a bridged bicyclic group; or
two R$^y$ groups on the same carbon atom, together with that carbon atom, form C(O);
R$^z$ is independently, at each occurrence, C$_{1-6}$ alkyl, halo, —CN, —NO$_2$, -(L$^2$)$_q$-OR$^3$, -(L$^2$)$_q$-SR$^2$, -(L$^2$)$_q$-S(=O)R$^2$, -(L$^2$)$_q$-S(=O)$_2$R$^2$, -(L$^2$)$_q$-NHS(=O)$_2$R$^2$, -(L$^2$)$_q$-C(=O)R$^2$, -(L$^2$)$_q$-OC(=O)R$^2$, -(L$^2$)$_q$CO$_2$R$^3$, -(L$^2$)$_q$-OCO$_2$R$^3$, -(L$^2$)$_q$-N(R$^3$)$_2$, -(L$^2$)$_q$-C(=O)N(R$^3$)$_2$, -(L$^2$)$_q$-OC(=O)N(R$^3$)$_2$, -(L$^2$)$_q$-NHC(=O)NH(R$^3$), -(L$^2$)$_q$-NHC(=O)R$^2$, -(L$^2$)$_q$-NHC(=O)OR$^2$, -(L$^2$)$_q$-C(OH)(R$^3$)$_2$, -(L$^2$)$_q$C(NH$_2$)(R$^3$)$_2$, —C$_{1-6}$ haloalkyl, —C$_{1-6}$ dihaloalkyl, —C$_{1-6}$ trihaloalkyl, C$_{3-7}$ cycloalkyl, a C$_{3-10}$ heterocycloalkyl, aryl, heteroaryl, —C$_{1-4}$ alkylene-(C$_{3-7}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);
L$^2$ is independently, at each occurrence, a bivalent radical selected from —(C$_{1-3}$ alkylene)-, —(C$_{3-7}$ cycloalkylene)-, —(C$_{1-3}$ alkylene)$_q$-O—(C$_{1-3}$ alkylene)-, or —(C$_{1-3}$ alkylene)$_q$-NH—(C$_{1-3}$ alkylene)$_q$-;
R$^1$ is H or C$_{1-6}$-alkyl.
R$^2$ is C$_{1-6}$ alkyl, —C$_{1-6}$ haloalkyl, —C$_{1-6}$ dihaloalkyl, —C$_{1-6}$ trihaloalkyl, C$_{3-10}$ cycloalkyl, C$_{3-10}$ heterocycloalkyl, aryl, heteroaryl, —C$_{1-4}$ alkylene-(C$_{3-10}$ cycloalkyl), —C$_{1-4}$ alkylene-(C$_{3-10}$ heterocycloalkyl), —C$_{1-4}$ alkylene-(aryl), or —C$_{1-4}$ alkylene-(heteroaryl);

each $R^3$ is independently, at each occurrence, H, $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

m is 1, 2, or 3;
n is 0, 1, 2, or 3;
p is 1, 2, or 3; and
q is 0 or 1.

In an embodiment of Formula II, ═══ denotes a double bond.

In another aspect, provided herein is a compound of Formula IIa:

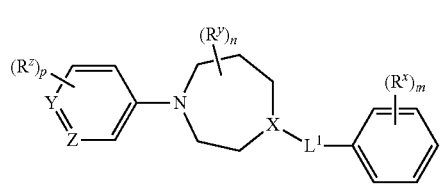

IIa or a pharmaceutically acceptable salt thereof,
wherein:
X is C or N;
one of Y or Z is N, and the other is C;
$L^1$ is —C(O)$NR^1$—, —$SO_2NR^1$—, —C(O)—, —C(O)O—, $C_{1-4}$ alkyl, or —$SO_2$—;
$R^x$ is independently, at each occurrence, halo, —CN, —$NO_2$, —$C_{1-6}$ haloalkyl, —$C_{1-6}$ dihaloalkyl, —$C_{1-6}$ trihaloalkyl, -$(L^2)_q$-C(═O)$R^2$, -$(L^2)_q$$CO_2R^3$, or -$(L^2)_q$-C(═O)N$(R^3)_2$;
$R^y$ is independently, at each occurrence, $C_{1-6}$ alkyl, halo, —CN, —$NO_2$, -$(L^2)_q$-$OR^3$, -$(L^2)_q$-$SR^2$, -$(L^2)_q$-S(═O)$R^2$, -$(L^2)_q$-S(═O)$_2R^2$, -$(L^2)_q$-NHS(═O)$_2R^2$, -$(L^2)_q$-C(═O)$R^2$, -$(L^2)_q$-OC(═O)$R^2$, -$(L^2)_q$$CO_2R^3$, -$(L^2)_q$-$OCO_2R^3$, -$(L^2)_q$-N$(R^3)_2$, -$(L^2)_q$-C(═O)N$(R^3)_2$, -$(L^2)_q$-OC(═O)N$(R^3)_2$, -$(L^2)_q$-NHC(═O)NH$(R^3)$, -$(L^2)_q$-NHC(═O)$R^2$, -$(L^2)_q$-NHC(═O)$OR^2$, -$(L^2)_q$-C(OH)$(R^3)_2$, -$(L^2)_q$C(NH$_2$)$(R^3)_2$, —$C_{1-6}$ haloalkyl, —$C_{1-6}$ dihaloalkyl, —$C_{1-6}$ trihaloalkyl, $C_{3-7}$ cycloalkyl, a $C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);
or:
two $R^y$ groups on adjacent carbon atoms are taken together to form a fused ring; or
two $R^y$ groups on non-adjacent carbon atoms are taken together to form a bridge of a bridged bicyclic group; or
two $R^y$ groups on the same carbon atom, together with that carbon atom, form C(O);
$R^z$ is independently, at each occurrence, $C_{1-6}$ alkyl, halo, —CN, —$NO_2$, -$(L^2)_q$-$OR^3$, -$(L^2)_q$-$SR^2$, -$(L^2)_q$-S(═O)$R^2$, -$(L^2)_q$-S(═O)$_2R^2$, -$(L^2)_q$-NHS(═O)$_2R^2$, -$(L^2)_q$-C(═O)$R^2$, -$(L^2)_q$-OC(═O)$R^2$, -$(L^2)_q$$CO_2R^3$, -$(L^2)_q$-$OCO_2R^3$, -$(L^2)_q$-N$(R^3)_2$, -$(L^2)_q$-C(═O)N$(R^3)_2$, -$(L^2)_q$-OC(═O)N$(R^3)_2$, -$(L^2)_q$-NHC(═O)NH$(R^3)$, -$(L^2)_q$-NHC(═O)$R^2$, -$(L^2)_q$-NHC(═O)$OR^2$, -$(L^2)_q$-C(OH)$(R^3)_2$, -$(L^2)_q$C(NH$_2$)$(R^3)_2$, —$C_{1-6}$ haloalkyl, —$C_{1-6}$ dihaloalkyl, —$C_{1-6}$ trihaloalkyl, $C_{3-7}$ cycloalkyl, a $C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

$L^2$ is independently, at each occurrence, a bivalent radical selected from —($C_{1-3}$ alkylene)-, —($C_{3-7}$ cycloalkylene)-, —($C_{1-3}$ alkylene)$_q$-O—($C_{1-3}$ alkylene)-, or —($C_{1-3}$ alkylene)$_q$-NH—($C_{1-3}$ alkylene)$_q$-;
$R^1$ is H or $C_{1-6}$-alkyl.
$R^2$ is $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);
each $R^3$ is independently, at each occurrence, H, $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);
m is 1, 2, or 3;
n is 0, 1, 2, or 3;
p is 1, 2, or 3; and
q is 0 or 1.

In one embodiment of the compounds of Formulae I, Ia, II and IIa provided herein,
X is C or N;
one of Y or Z is N, and the other is C;
$L^1$ is —C(O)$NR^1$—, or —$SO_2NR^1$—;
$R^x$ is independently, at each occurrence, halo;
$R^y$ is independently, at each occurrence, $C_{1-6}$ alkyl, halo, -$(L^2)_q$-$OR^3$, -$(L^2)_q$$CO_2R^3$, —$C_{1-4}$ alkylene-(aryl); or
two $R^y$ groups on adjacent carbon atoms are taken together to form a fused ring; or
two $R^y$ groups on non-adjacent carbon atoms are taken together to form a bridge of a bridged bicyclic group; or
two $R^y$ groups on the same carbon atom, together with that carbon atom, form C(O);
$R^z$ is independently, at each occurrence, $C_{1-6}$ alkyl, halo, -$(L^2)_q$-$OR^3$, $C_{3-7}$ cycloalkyl;
$L^2$ is independently, at each occurrence, a bivalent radical selected from —($C_{1-3}$ alkylene)-;
each $R^3$ is independently, at each occurrence, H, $C_{1-6}$ alkyl, or —$C_{1-4}$ alkylene-(aryl);
m is 1, 2, or 3;
n is 0, 1, 2, or 3;
p is 1, 2, or 3; and
q is 0 or 1.

In an embodiment of Formula IIa, ═══ denotes a double bond.

In another embodiment of the compounds of Formula I and Formula II provided herein, X is N. In another embodiment of the compounds of Formula I and Formula II provided herein, X is C.

In one embodiment of the compounds of Formula I and Formula II provided herein, Y is N, and Z is C.

In another embodiment of the compounds of Formula I and Formula II provided herein, $L^1$ is —C(O)$NR^1$— or —$SO_2NR^1$—. In a preferred embodiment, $L^1$ is —C(O)$NR^1$, or in a more preferred embodiment, —C(O)NH—.

In one embodiment of the compounds of Formula I and Formula II provided herein, $R^x$ is independently, at each occurrence, halo, —CN, —$NO_2$, —$C_{1-6}$ haloalkyl, —$C_{1-6}$ dihaloalkyl, or —$C_{1-6}$ trihaloalkyl. In another embodiment, $R^x$ is independently, at each occurrence, halo. In a further embodiment, $R^x$ is independently, at each occurrence —F or —Cl.

In one embodiment of the compounds of Formula I and Formula II provided herein, $R^y$ is $C_{1-6}$ alkyl, halo, -$(L^2)_q$-$OR^3$, -$(L^2)_q$$CO_2R^3$ or —$C_{1-4}$ alkylene-(aryl). In another embodiment of the compounds of Formula I and Formula II provided herein, two $R^y$ groups on the same carbon atom, together with that carbon atom, form C(O). In yet another embodiment of the compounds of Formula I and Formula II provided herein, two $R^y$ groups on adjacent carbon atoms are taken together to form a fused ring, and wherein the ring is $C_{3-10}$-cycloalkyl or phenyl. In a further embodiment of the compounds of Formula I and Formula II provided herein, two $R^y$ groups on non-adjacent carbon atoms are taken together to form a bridge of a bridged bicyclic group, and wherein the bridge is a $C_{1-3}$-alkyl chain.

In one embodiment of the compounds of Formula I and Formula II provided herein, $R^z$ is independently, at each occurrence, $C_{1-6}$ alkyl, halo, -$(L^2)_q$-$OR^3$, $C_{3-7}$ cycloalkyl, —$C_{1-4}$ alkylene-($C_{3-7}$ cycloalkyl), —$C_{1-4}$ alkylene-(aryl), or —$C_{1-4}$ alkylene-(heteroaryl). In a further embodiment, $R^z$ is independently, at each occurrence, $C_{1-6}$ alkyl, halo, -$(L^2)_q$-$OR^3$, or $C_{3-7}$ cycloalkyl. In yet a further embodiment, $R^z$ is independently, at each occurrence, $C_{1-6}$ alkyl or halo. In yet another embodiment, $R^z$ is independently, at each occurrence, —Cl, —F, —$CH_3$, —$OCH_3$, or cyclopropyl.

In another embodiment of the compounds of Formula I and Formula II provided herein, $L^2$ is —$(C_{1-3}$ alkylene)-.

In another embodiment of the compounds of Formula I and Formula II provided herein, $R^3$ is H, $C_{1-6}$ alkyl, or —$C_{1-4}$ alkylene-(aryl).

In yet a further embodiment, -$(L^2)_q$-$OR^3$ is —OH, —$OCH_3$, —$CH_2OH$, —$CH_2CH_2OH$, —$CH_2OCH_3$, or —$CH_2 CH_2OCH_3$.

In an embodiment of the compounds of Formula I and Formula II provided herein, X is N; $R^y$ is —$C_{1-6}$ alkyl, halo, -$(L^2)_q$-$OR^3$, -$(L^2)_qCO_2R^3$ or —$C_{1-4}$ alkylene-(aryl); $R^z$ is independently, at each occurrence, $C_{1-6}$ alkyl, halo, or $C_{3-7}$ cycloalkyl; $R^x$ is independently, at each occurrence, halo; and n is 0 or 1.

In an embodiment, compounds of Formula II have the Formula III:

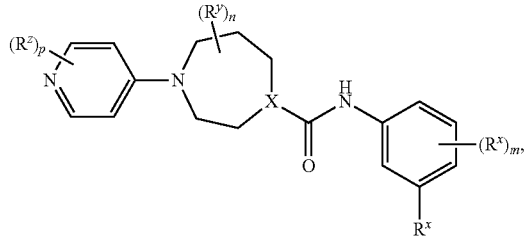

III or a pharmaceutically acceptable salt thereof,
wherein m is C, 1, or 2, and wherein all other variables, e.g., X, $R^x$, $R^y$, $R^z$, n, and p, have the definitions as provided for Formula II.

In an embodiment of the compounds of Formula III provided herein, X is N. In another embodiment of the compounds of Formula III provided herein, X is C.

In one embodiment of the compounds of Formula III, provided herein, $R^x$ is independently, at each occurrence, halo, —CN, —$NO_2$, —$C_{1-6}$ haloalkyl, —$C_{1-6}$ dihaloalkyl, or —$C_{1-6}$ trihaloalkyl. In another embodiment, $R^x$ is independently, at each occurrence, halo. In a further embodiment, $R^x$ is independently, at each occurrence —F or —Cl.

In one embodiment of the compounds of Formula III provided herein, $R^y$ is $C_{1-6}$ alkyl, halo, -$(L^2)_q$-$OR^3$, -$(L^2)_qCO_2R^3$ or —$C_{1-4}$ alkylene-(aryl). In another embodiment of the compounds of Formula III provided herein, two $R^y$ groups on the same carbon atom, together with that carbon atom, form C(O). In yet another embodiment of the compounds of Formula III provided herein, two $R^y$ groups on adjacent carbon atoms are taken together to form a fused ring, and wherein the ring is $C_{3-10}$-cycloalkyl or phenyl. In a further embodiment of the compounds of Formula III provided herein, two $R^y$ groups on non-adjacent carbon atoms are taken together to form a bridge of a bridged bicyclic group, and wherein the bridge is a $C_{1-3}$-alkyl chain.

In one embodiment of the compounds of Formula III provided herein, $R^z$ is independently, at each occurrence, $C_{1-6}$ alkyl, halo, -$(L^2)_q$-$OR^3$, $C_{3-7}$ cycloalkyl, —$C_{1-4}$ alkylene-($C_{3-7}$ cycloalkyl), —$C_{1-4}$ alkylene-(aryl), or —$C_{1-4}$ alkylene-(heteroaryl). In a further embodiment, $R^z$ is independently, at each occurrence, $C_{1-6}$ alkyl, halo, -$(L^2)_q$-$OR^3$, or $C_{3-7}$ cycloalkyl. In yet a further embodiment, $R^z$ is independently, at each occurrence, $C_{1-6}$ alkyl or halo. In yet another embodiment, $R^z$ is independently, at each occurrence, —Cl, —F, —$CH_3$, —$OCH_3$, or cyclopropyl.

In another embodiment of the compounds of Formula III provided herein, $L^2$ is —$(C_{1-3}$ alkylene)-.

In another embodiment of the compounds of Formula III provided herein, $R^3$ is H, $C_{1-6}$ alkyl, or —$C_{1-4}$ alkylene-(aryl).

In yet a further embodiment, -$(L^2)_q$-$OR^3$ is —OH, —$OCH_3$, —$CH_2OH$, —$CH_2CH_2OH$, —$CH_2OCH_3$, or —$CH_2 CH_2OCH_3$.

In an embodiment of the compounds of Formula III provided herein, X is N; $R^y$ is —$C_{1-6}$ alkyl, halo, -$(L^2)_q$-$OR^3$, -$(L^2)_qCO_2R^3$ or —$C_{1-4}$ alkylene-(aryl); $R^z$ is independently, at each occurrence, $C_{1-6}$ alkyl, halo, or $C_{3-7}$ cycloalkyl; $R^x$ is independently, at each occurrence, halo; and n is 0 or 1.

In a further embodiment, compounds of Formula II have the Formula IV:

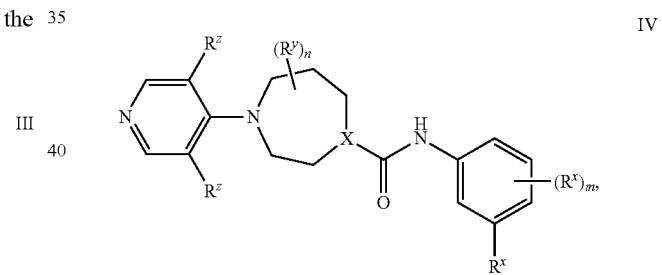

IV or a pharmaceutically acceptable salt thereof,
wherein m is C, 1, or 2, and wherein all other variables, e.g., X, $R^x$, $R^y$, $R^z$, and n, have the definitions as provided for Formula II.

In an embodiment of the compounds of Formula IV provided herein, X is N. In another embodiment of the compounds of Formula IV provided herein, X is C.

In one embodiment of the compounds of Formula IV, provided herein, $R^x$ is independently, at each occurrence, halo, —CN, —$NO_2$, —$C_{1-6}$ haloalkyl, —$C_{1-6}$ dihaloalkyl, or —$C_{1-6}$ trihaloalkyl. In another embodiment, $R^x$ is independently, at each occurrence, halo. In a further embodiment, $R^x$ is independently, at each occurrence —F or —Cl.

In one embodiment of the compounds of Formula IV provided herein, $R^y$ is H, $C_{1-6}$ alkyl, halo, -$(L^2)_q$-$OR^3$, -$(L^2)_qCO_2R^3$ or —$C_{1-4}$ alkylene-(aryl). In another embodiment of the compounds of Formula IV provided herein, two $R^y$ groups on the same carbon atom, together with that carbon atom, form C(O). In yet another embodiment of the compounds of Formula IV provided herein, two $R^y$ groups on adjacent carbon atoms are taken together to form a fused ring, and wherein the ring is $C_{3-10}$-cycloalkyl or phenyl. In a further embodiment of the compounds of Formula IV provided herein, two $R^y$ groups on non-adjacent carbon atoms are taken together to form a bridge of a bridged bicyclic group, and wherein the bridge is a $C_{1-3}$-alkyl chain.

In one embodiment of the compounds of Formula IV provided herein, $R^z$ is independently, at each occurrence, $C_{1-6}$ alkyl, halo, -$(L^2)_q$-$OR^3$, $C_{3-7}$ cycloalkyl, —$C_{1-4}$ alkylene-($C_{3-7}$ cycloalkyl), —$C_{1-4}$ alkylene-(aryl), or —$C_{1-4}$ alkylene-(heteroaryl). In a further embodiment, $R^z$ is independently, at each occurrence, $C_{1-6}$ alkyl, halo, -$(L^2)_q$-$OR^3$, or $C_{3-7}$ cycloalkyl. In yet a further embodiment, $R^z$ is independently, at each occurrence, $C_{1-6}$ alkyl or halo. In yet another embodiment, $R^z$ is independently, at each occurrence, —Cl, —F, —$CH_3$, —$OCH_3$, or cyclopropyl.

In another embodiment of the compounds of Formula IV provided herein, $L^2$ is —($C_{1-3}$ alkylene)-.

In another embodiment of the compounds of Formula IV provided herein, $R^3$ is H, $C_{1-6}$ alkyl, or —$C_{1-4}$ alkylene-(aryl).

In yet a further embodiment, -$(L^2)_q$-$OR^3$ is —OH, —$OCH_3$, —$CH_2OH$, —$CH_2CH_2OH$, —$CH_2OCH_3$, or —$CH_2CH_2OCH_3$.

In a preferred embodiment of the compounds of Formula IV provided herein, X is N; $R^y$ is —$C_{1-6}$ alkyl, halo, -$(L^2)_q$-$OR^3$, -$(L^2)_q$$CO_2R^3$ or —$C_{1-4}$ alkylene-(aryl); $R^z$ is independently, at each occurrence, $C_{1-6}$ alkyl, halo, or $C_{3-7}$ cycloalkyl; $R^x$ is independently, at each occurrence, halo; and n is 0 or 1.

In yet a further embodiment of Formula IV, or a pharmaceutically acceptable salt thereof, X is C or N;

$R^x$ is independently, at each occurrence, halo;

$R^y$ is independently, at each occurrence, $C_{1-6}$ alkyl, halo, -$(L^2)_q$-$OR^3$, -$(L^2)_q$$CO_2R^3$, —$C_{1-4}$ alkylene-(aryl); or two $R^y$ groups on adjacent carbon atoms are taken together to form a fused ring; or two $R^y$ groups on non-adjacent carbon atoms are taken together to form a bridge of a bridged bicyclic group; or two $R^y$ groups on the same carbon atom, together with that carbon atom, form C(O);

$R^z$ is independently, at each occurrence, $C_{1-6}$ alkyl, halo, -$(L^2)_q$-$OR^3$, $C_{3-7}$ cycloalkyl;

$L^2$ is independently, at each occurrence, a bivalent radical selected from —($C_{1-3}$ alkylene)-;

each $R^3$ is independently, at each occurrence, H, $C_{1-6}$ alkyl, or —$C_{1-4}$ alkylene-(aryl); and q is 0 or 1.

In one aspect, the compound of the invention is a compound of Formula V:

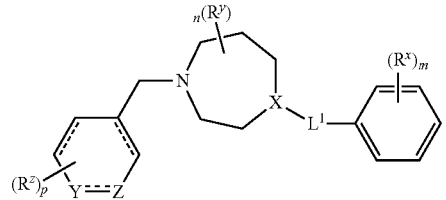

or a pharmaceutically acceptable salt thereof, wherein

X is C or N;

each Y and Z are independently selected from N and C;

$L^1$ is —C(O)$NR^1$—, or —$SO_2NR^1$—;

$R^x$ is independently, at each occurrence, halo;

$R^y$ is independently, at each occurrence, $C_{1-6}$ alkyl, halo, -$(L^2)_q$-$OR^3$, -$(L^2)_q$$CO_2R^3$, —$C_{1-4}$ alkylene-(aryl); or two $R^y$ groups on adjacent carbon atoms are taken together to form a fused ring; or two $R^y$ groups on non-adjacent carbon atoms are taken together to form a bridge of a bridged bicyclic group; or two $R^y$ groups on the same carbon atom, together with that carbon atom, form C(O);

$R^z$ is independently, at each occurrence, $C_{1-6}$ alkyl, halo, -$(L^2)_q$-$OR^3$, $C_{3-7}$ cycloalkyl;

$L^2$ is independently, at each occurrence, a bivalent radical selected from —($C_{1-3}$ alkylene)-;

each $R^3$ is independently, at each occurrence, H, $C_{1-6}$ alkyl, or —$C_{1-4}$ alkylene-(aryl);

m is 1, 2, or 3;

n is 0, 1, 2, or 3;

p is 1, 2, or 3; and q is 0 or 1.

In an embodiment of Formula V, $\rightleftharpoons$ denotes a double bond, Y is N and Z is C.

Preferred embodiments of Formulas I-V, including pharmaceutically acceptable salts thereof, are shown below in Table 1. All compounds of Formulas I, Ia, II, IIa, III, IV, and V as well as pharmaceutically acceptable salts thereof, and the compounds of Table 1, as well as pharmaceutically acceptable salts thereof, are considered to be "compounds of the invention."

Synthetic method codes refer to the synthesis methodologies provided in the experimental section. For example, "A01B01C01D01" refers the use of intermediate A01 for region A, intermediate B01 for region B, intermediate C01 for region C, and intermediate D01 for region D.

TABLE 1

| Cmp. ID<br>Synthetic Method | Structure<br>MS (M + H)+<br>$^1$H NMR |
|---|---|
| 001<br>General procedure A<br>A01B01C01D01 | 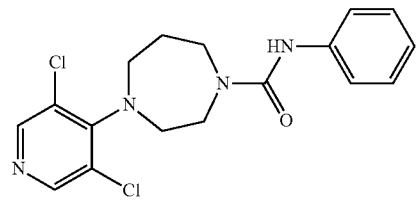<br>365/367 |

$^1$H NMR (400 MHz, $CD_3OD$) δ 8.44 (s, 2H), 7.40-7.42 (m, 2H), 7.07-7.31 (m, 2H), 7.05-7.07 (m, 1H), 3.77-3.83 (m, 4H), 3.43-3.47 (m, 4H), 2.00-2.06 (m, 2H).

TABLE 1-continued
| | Structure |
|---|---|
| Cmp. ID | MS (M + H)+ |
| Synthetic Method | ¹H NMR |
002
General procedure A
A01B01C01D02
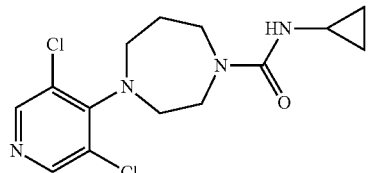
329/331
003
General procedure A
A01B01C01D03
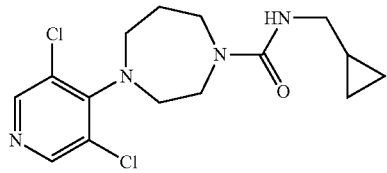
343/345
004
General procedure A
A01B01C01D04
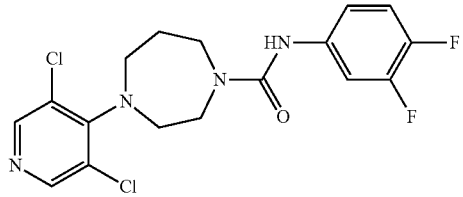
401/403
¹H NMR (400 MHz, CD₃OD) δ 8.45 (s, 2H), 7.47-7.50 (m, 1H), 7.15-7.18 (m, 2H), 3.75-3.81 (m, 4H), 3.42-3.46 (m, 4H), 1.99-2.05 (m, 2H).
005
General procedure A
A01B01C01D05
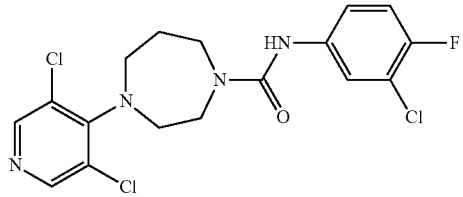
417/419
006
General procedure A
A01B01C01D07
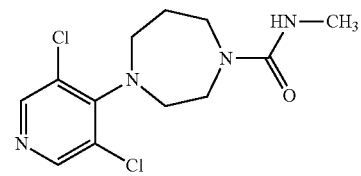
303/305

TABLE 1-continued

| Cmp. ID<br>Synthetic Method | Structure<br>MS (M + H)⁺<br>¹H NMR |
|---|---|
| 007<br>General procedure A<br>A01B01C01D08 | [Structure: 3,5-dichloropyridin-4-yl diazepane carboxamide with 3-pyridyl]<br>366/368<br>¹H NMR (400 MHz, CD₃OD) δ 8.66 (d, J = 2.4 Hz, 1H), 8.45 (s, 2H), 8.21 (dd, J = 1.2, 4.8 Hz, 1H), 7.97-7.99 (m, 1H), 7.30 (dd, J = 4.8 Hz, 8.4 Hz, 1H), 3.78-3.84 (m, 4H), 3.45-3.48 (m, 4H), 2.00-2.06 (m, 2H). |
| 008<br>General procedure A<br>A01B01C01D09 | [Structure: 3,5-dichloropyridin-4-yl diazepane carboxamide with 2-hydroxyethyl]<br>333/335 |
| 009<br>General procedure A<br>A01B01C01D10 | [Structure: 3,5-dichloropyridin-4-yl diazepane carboxamide with 2-methoxyethyl]<br>347/349 |
| 010<br>General procedure A<br>A01B01C01D11 | [Structure: 3,5-dichloropyridin-4-yl diazepane carboxamide with 3-chlorophenyl]<br>399/401<br>¹H NMR (400 MHz, CD₃OD) δ 8.44 (s, 2H), 7.58 (t, J = 2.0 Hz, 1H), 7.32-7.35 (m, 1H), 7.26 (t, J = 8.0 Hz, 1H), 7.02-7.05 (m, 1H), 3.76-3.82 (m, 4H), 3.42-3.47 (m, 4H), 1.99-2.05 (m, 2H). |
| 011<br>General procedure A<br>A01B01C01D12 | [Structure: 3,5-dichloropyridin-4-yl diazepane carboxamide with 3-fluorophenyl]<br>383/385 |

TABLE 1-continued
| Cmp. ID<br>Synthetic Method | Structure<br>MS (M + H)+<br>1H NMR |
|---|---|
| 012<br>General procedure A<br>A01B01C01D13 | 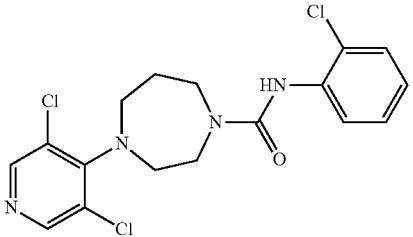<br>399/401 |
| 013<br>General procedure A<br>A01B01C01D14 | 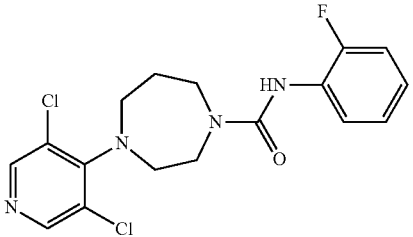<br>383/385 |
| 014<br>General procedure B<br>A01B01C01D15 | 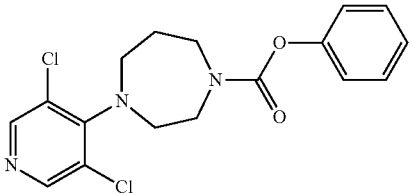<br>366/368 |
| 015<br>General procedure B<br>A01B01C01D16 | 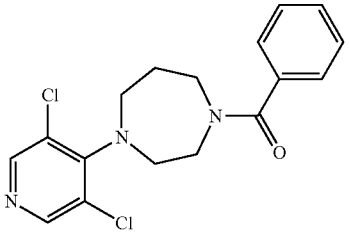<br>350/352 |
| 016<br>General procedure B<br>A01B01C01D17 | 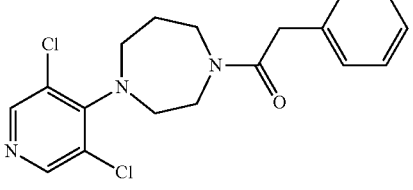<br>364/366 |

TABLE 1-continued

| Cmp. ID<br>Synthetic Method | Structure<br>MS (M + H)+<br>¹H NMR |
|---|---|
| 017<br>General procedure A<br>A02B01C01D01 | 331/333<br>¹H NMR (400 MHz, CD₃OD) δ 8.28 (s, 1 H), 8.13-8.16 (m, 2 H), 7.24-7.32 (m, 4 H), 7.04-7.11 (m, 2 H), 3.83 (s, 4 H), 3.69-3.74 (m, 4 H), 2.12-2.15 (m, 2 H). |
| 018<br>General procedure F<br>A03B01C01D01 | 397 |
| 019<br>General procedure F<br>A04B01C01D01 | 364/366 |
| 020<br>General procedure F<br>A05B01C01D01 | 297/299 |
| 021<br>General procedure F<br>A06B01C01D01 | 317 |
| 022<br>General procedure F<br>A07B01C01D01 | 310<br>¹H NMR (400 MHz, CD₃OD) δ 7.35-7.54 (m, 7 H), 7.25-7.32 (m, 2 H), 7.03-7.10 (m, 1 H), 4.13 (s, 2 H), 3.73-3.80 (m, 2 H), 3.67 (t, J = 6.27 Hz, 2 H), 3.12-3.21 (m, 4 H), 2.13-2.16 (m, 2 H). |

TABLE 1-continued

| Cmp. ID Synthetic Method | Structure MS (M + H)+ ¹H NMR |
|---|---|

023
General procedure F
A08B01C01D01

378/380

024
General procedure A
A01B02C01D01

351/353

025
General procedure A
A01B01C01D06

419/421

¹H NMR (400 MHz, CD₃OD) δ 8.45 (s, 2H), 7.26-7.34 (m, 2H), 3.74-3.81 (m, 4H), 3.41-3.46 (m, 4H), 1.99-2.05 (m, 2H).

026
General procedure D
A01B01C02D12

419/421

027
General procedure D
A01B01C02D24

419/421

TABLE 1-continued
| Cmp. ID<br>Synthetic Method | Structure<br>MS (M + H)+<br>¹H NMR |
|---|---|
| 028<br>General procedure D<br>A01B01C02D11 | 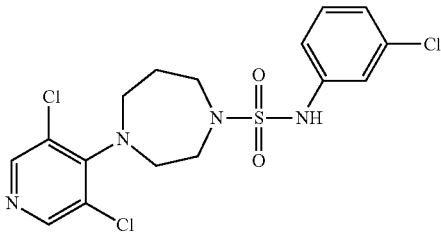<br>435/437 |
| 029<br>General procedure D<br>A01B01C02D25 | 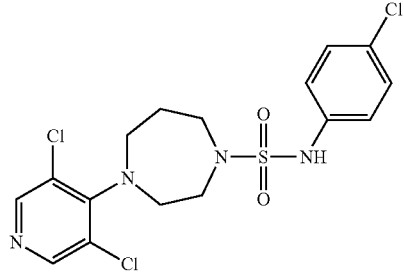<br>435/437 |
| 030<br>General procedure D<br>A01B01C02D05 | 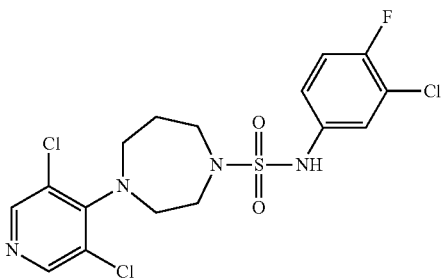<br>453/455 |
| 031<br>General procedure D<br>A01B01C02D07 | 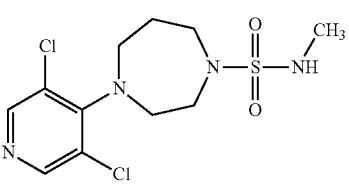<br>339/341<br>¹H NMR (400 MHz, CD₃OD) δ 8.45 (s, 2H), 3.63 (t, J = 6.0 Hz, 2H), 3.56-3.58 (m, 2H), 3.43-3.47 (m, 4H), 2.64 (s, 3H), 2.03-2.09 (m, 2H). |
| 032<br>General procedure D<br>A01B01C02D03 | 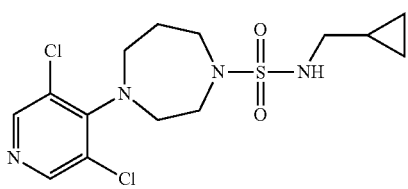<br>379/381 |

TABLE 1-continued

| Cmp. ID Synthetic Method | Structure MS (M + H)+ ¹H NMR |
|---|---|
| 033 General procedure D A01B01C02D10 | [Structure: 3,5-dichloropyridin-4-yl homopiperazine sulfonamide with N-(2-methoxyethyl)] 383/385 |
| 034 General procedure D A01B01C02D21 | [Structure: 3,5-dichloropyridin-4-yl homopiperazine sulfonamide with N-isopropyl] 367/369 |
| 035 General procedure D A01B01C02D22 | [Structure: 3,5-dichloropyridin-4-yl homopiperazine sulfonamide with N-cyclohexyl] 407/409 |
| 036 General procedure C A01B01C02D16 | [Structure: 3,5-dichloropyridin-4-yl homopiperazine phenylsulfonyl] 386/388 |
| 037 General procedure C A01B01C02D17 | [Structure: 3,5-dichloropyridin-4-yl homopiperazine benzylsulfonyl] 400/402 |
| 038 General procedure D A01B01C02D01 | [Structure: 3,5-dichloropyridin-4-yl homopiperazine sulfonamide with N-phenyl] 401/403 |

¹H NMR (400 MHz, CD₃OD) δ 8.40 (s, 2H), 7.31-7.36 (m, 2H), 7.23-7.26 (m, 2H), 7.11-7.14 (m, 1H), 3.60 (t, J = 6.0 Hz, 2H), 3.53-3.55 (m, 2H), 3.32-3.55 (m, 2H), 3.27 (t, J = 6.0 Hz, 2H), 1.93-7.99 (m, 2H).

TABLE 1-continued
| | Structure |
|---|---|
| Cmp. ID<br>Synthetic Method | MS (M + H)+<br>1H NMR |
039
General procedure C
A01B01C02D23
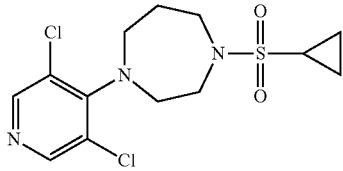
350/352
1H NMR (400 MHz, CD3OD) δ 8.45 (s, 2H), 3.69 (t, J = 6.0 Hz, 2H), 3.61-3.63 (m, 2H), 3.44-3.47 (m, 4H), 2.58-2.62 (m, 1H), 2.05-2.09 (m, 2H), 1.00-1.11 (m, 4H).
040
General procedure A
A02B01C01D05
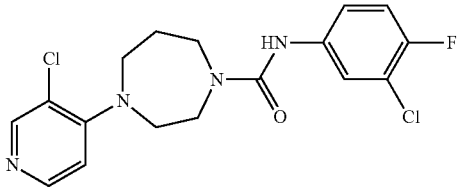
383/385
1H NMR (400 MHz, MeOD) δ 8.13-8.15 (m, 2 H), 7.51-7.53 (m, 1 H), 7.23-7.25 (m, 1 H), 7.08-7.15 (m, 2 H), 3.79-3.86 (m, 4H), 3.68-3.72 (m, 4 H), 2.10-2.16 (m, 2H).
041
General procedure A
A09B01C01D05
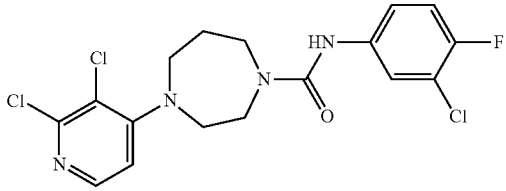
417/419
042
General procedure A
A10B01C01D05
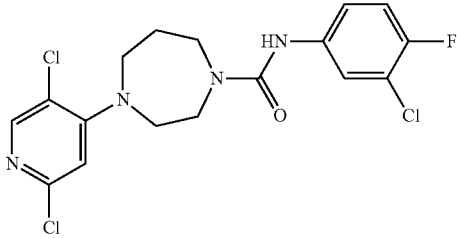
417/419
043
General procedure E
A11B01C01D05
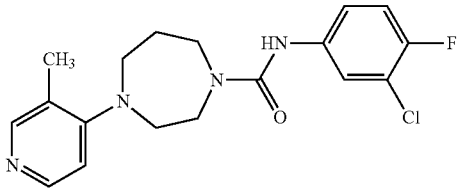
363/365

TABLE 1-continued

| Cmp. ID<br>Synthetic Method | Structure<br>MS (M + H)+<br>1H NMR |
|---|---|
| 044<br>General procedure G<br>A12B01C01D05 | 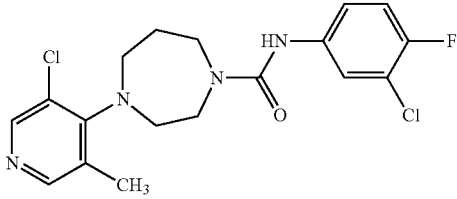<br>397/399 |
| 045<br>General procedure J<br>A13B01C01D05 | 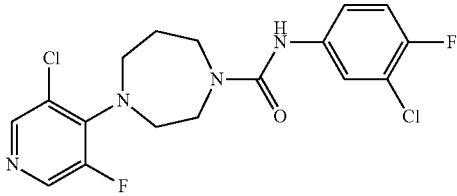<br>401/403<br>1H NMR (400 MHz, CD3OD) δ 8.45 (s, 2 H), 7.43-7.52 (m, 1 H), 7.12-7.20 (m, 2 H), 3.79 (dt, J = 13.49 Hz, 5.80 Hz, 4 H), 3.44 (q, J = 5.94 Hz, 4 H), 2.02 (dt, J = 11.29 Hz, 5.90 Hz, 2 H). |
| 046<br>General procedure K<br>A14B01C01D05 | 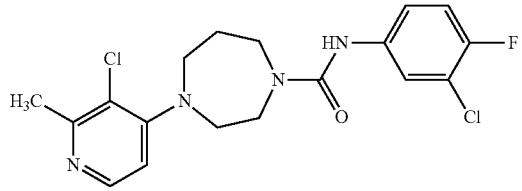<br>397/399 |
| 047<br>General procedure G<br>A15B01C01D05 | 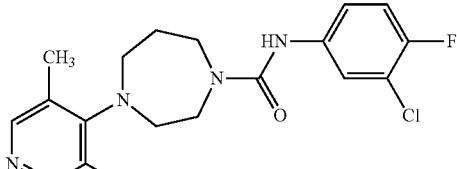<br>377/379<br>1H NMR (400 MHz, CD3OD) δ 8.19 (s, 2H), 7.56 (dd, J = 2.8 Hz, 6.4 Hz, 1H), 7.19-7.22 (m, 1H), 7.06 (t, J = 8.8 Hz, 1H), 6.64 (s, 1H), 3.67-3.73 (m, 4H), 3.19-3.25 (m, 4H), 2.24 (s, 6H), 1.95-2.00 (m, 2H). |
| 048<br>General procedure A<br>A16B01C01D05 | 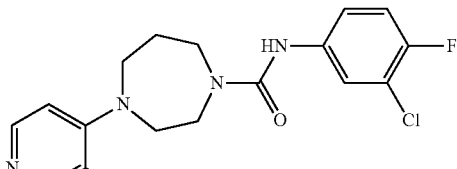<br>379/381 |

TABLE 1-continued

| Cmp. ID<br>Synthetic Method | Structure<br>MS (M + H)⁺<br>¹H NMR |
|---|---|
| 049<br>General procedure A<br>A01B01C01D018 | [Structure: 3,5-dichloropyridin-4-yl homopiperazine carboxamide with 4-chloro-3-fluorophenyl]<br>417/419 |
| 050<br>General procedure A<br>A17B01C01D05 | [Structure: 2,6-dichlorophenyl homopiperazine carboxamide with 3-chloro-4-fluorophenyl]<br>416/418 |
| 051<br>General procedure A<br>A18B01C01D05 | [Structure: 2,4-dichloropyridin-3-yl homopiperazine carboxamide with 3-chloro-4-fluorophenyl]<br>417/419<br>¹H NMR (400 MHz, MeOD) δ 7.64-7.67 (m, 2 H), 7.19-7.23 (m, 1 H), 7.10-7.15 (m, 2 H), 3.27-3.33 (m, 8 H), 1.70-1.76 (m, 2H). |
| 052<br>General procedure D<br>A01B01C02D04 | [Structure: 3,5-dichloropyridin-4-yl homopiperazine sulfamide with 3,4-difluorophenyl]<br>437/439 |
| 053<br>General procedure A<br>A01B01C01D19 | [Structure: 3,5-dichloropyridin-4-yl homopiperazine N-methyl carboxamide with 3-chloro-4-fluorophenyl]<br>431/433<br>¹H NMR (400 MHz, CD₃OD) δ 8.42 (s, 2H), 7.31-3.33 (m, 1H), 7.27 (t, J = 9.0 Hz, 1H), 7.14-7.15 (m, 1H), 3.43-3.48 (m, 4H), 3.30-3.32 (m, 4H), 3.18 (s, 3H), 1.88-1.94 (m, 2H). |

TABLE 1-continued

| Cmp. ID<br>Synthetic Method | Structure<br>MS (M + H)⁺<br>¹H NMR |
|---|---|

054
General procedure H
A01B23C01D01

364/366

055
General procedure H
A01B23C01D05

416/418

¹H NMR (400 MHz, CD$_3$OD-d4) δ 8.45 (s, 2H), 7.85-7.87 (m, 1H), 7.44-7.47 (m, 1H), 7.17-7.22 (m, 1H), 3.31-3.48 (m, 4H), 2.78-2.82 (m, 1H), 2.01-2.10 (m, 6H).

056
General procedure H
A01B23C01D04

400/402

057
General procedure I
A01B24C01D01

379/381

058
General procedure I
A01B24C01D04

415/417

¹H NMR (400 MHz, CD$_3$OD-d4) δ 8.64 (s, 2H), 7.48-7.51 (m, 1H), 7.14-7.19 (m, 2H), 4.56 (s, 2H), 3.88-3.92 (m, 4H), 2.14-2.16 (m, 2H).

TABLE 1-continued

| Cmp. ID  
Synthetic Method | Structure  
MS (M + H)+  
¹H NMR |
|---|---|

059  
General procedure I  
A01B24C01D05

431/433

060  
General procedure I

379/381

¹H NMR (400 MHz, CD₃OD) δ 8.68 (s, 2 H), 7.40 (d, J = 7.78 Hz, 2 H), 7.27-
7.33 (m, 2 H), 7.04-7.09 (m, 1 H), 3.99-4.03 (m, 2 H), 3.88-3.95 (m, 4
H), 3.00-3.05 (m, 2 H).

061  
General procedure I  
A01B25C01D04

415/417

062  
General procedure I  
A01B25C01D05

431/433

063  
General procedure L  
A01B26C01D01

377/379

¹H NMR (400 MHz, CD₃OD) δ 8.36 (s, 2H), 7.24-7.35 (m, 4H), 7.03-7.05 (m,
1H), 4.53 (t, J = 4.4 Hz, 1H), 4.29 (d, J = 11.6 Hz, 1H), 4.21 (d, J = 8.8 Hz,
1H), 3.74 (d, J = 13.2 Hz, 1H), 3.24 (d, J = 12.0 Hz, 1H), 3.13-3.17 (m, 1H),
3.07 (d, J = 12.0 Hz, 1H), 2.71 (s, 1H), 2.27-2.33 (m, 1H), 1.96 (d, J = 10.8
Hz, 1H).

TABLE 1-continued
| Cmp. ID<br>Synthetic Method | Structure<br>MS (M + H)+<br>¹H NMR |
|---|---|
| 064<br>General procedure L<br>A01B26C01D04 | 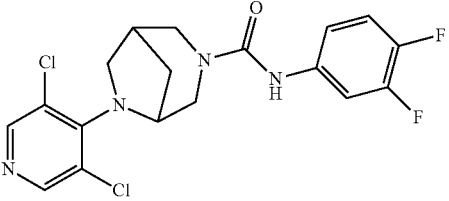 [SMILES: O=C(Nc1ccc(F)c(F)c1)N1CC2CCC(C1)N(c1c(Cl)cncc1Cl)C2]<br>413/415 |
| 065<br>General procedure L<br>A01B26C01D05 | 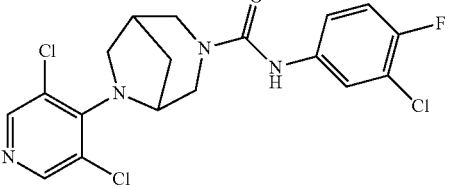<br>429/431 |
| 066<br>General procedure L<br>A01B27C01D01 | 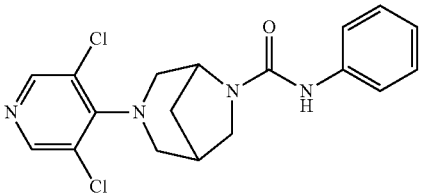 [SMILES: O=C(Nc1ccccc1)N1CCC2CC1CN2c1c(Cl)cncc1Cl]<br>377/379 |
| 067<br>General procedure L<br>A01B27C01D04 | 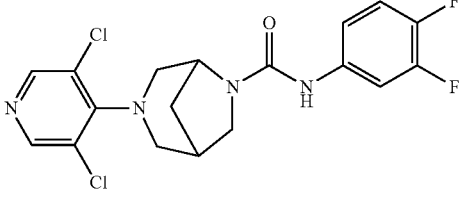<br>¹HNMR (400 MHz, CD₃OD) δ 8.43 (s, 2H), 7.47-7.52 (m, 2H), 7.14-7.18 (m, 1H), 4.34 (t, J = 4.4 Hz, 1H), 3.82 (d, J = 10.8 Hz, 1H), 3.78 (d, J = 9.6 Hz, 1H), 3.63-3.64 (m, 1H), 3.44 (dd, J = 2.8 Hz, 11.2 Hz, 1H), 3.31-3.32 (m, 1H), 3.00 (d, J = 10.4 Hz, 1H), 2.67 (s, 1H), 2.13 (s, 1H), 1.95 (d, J = 10.8 Hz, 1H). |
| 068<br>General procedure L<br>A01B27C01D05 | 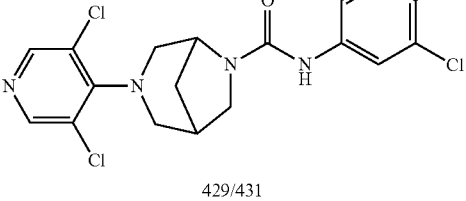<br>429/431 |
| 069 | 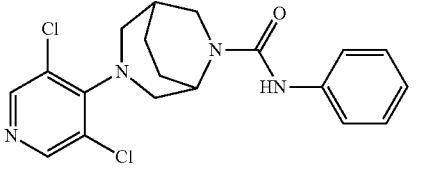 |

TABLE 1-continued

| Cmp. ID Synthetic Method | Structure MS (M + H)⁺ ¹H NMR |
|---|---|
| 070 | |
| 071 | |
| 072 | |
| 073 | |
| 074 | |
| 075 | |
| 076 | |

TABLE 1-continued

| Cmp. ID Synthetic Method | Structure MS (M + H)+ ¹H NMR |
|---|---|
| 077 | |
| 078 | |
| 079 | |
| 080 | |
| 081 | |
| 082 | |
| 083 | |

TABLE 1-continued

| Cmp. ID<br>Synthetic Method | Structure<br>MS (M + H)+<br>¹H NMR |
|---|---|
| 084 | *(structure: 3,5-dichloropyridine-diazabicyclic urea with phenyl)* |
| 085 | *(structure: 3,5-dichloropyridine-diazabicyclic urea with 3,4-difluorophenyl)* |
| 086 | *(structure: 3,5-dichloropyridine-diazabicyclic urea with 3-chloro-4-fluorophenyl)* |
| 087<br>General procedure A<br>A01B03C01D05 | *(structure: 3,5-dichloropyridine-methyl-diazepane urea with 3-chloro-4-fluorophenyl)*<br>431/433<br>¹H NMR (400 MHz, MeOD) δ 8.45 (s, 2 H), 7.15-7.63 (m, 3 H), 3.67-4.39 (m, 3 H), 3.15-3.47 (m, 4 H), 1.77-2.35 (m, 2 H), 1.14 (d, J = 6.4 Hz, 3H). |
| 088<br>General procedure A<br>A01B04C01D05 | *(structure: 3,5-dichloropyridine-ethyl-diazepane urea with 3-chloro-4-fluorophenyl)*<br>445/447<br>¹H NMR (400 MHz, CD₃OD) δ 8.45 (s, 2H), 7.60 (dd, J = 2.6 Hz, 6.8 Hz, 2H), 7.29-7.31 (m, 1H), 7.16 (t, J = 9.0 Hz, 1H), 4.26 (s, 1H), 3.98 (d, J = 11.2 Hz, 1H), 3.75-3.80 (m, 1H), 3.36-3.38 (m, 2H), 3.21-3.24 (m, 2H), 2.28-2.33 (m, 1H), 1.76 (d, 1H), 1.53-1.61 (m, 2H), 0.92-0.95 (t, 3H). |
| 089_R<br>General procedure A<br>A01B05C01D05 | *(structure: 3,5-dichloropyridine-isopropyl-diazepane urea with 3-chloro-4-fluorophenyl)*<br>459/461 |

TABLE 1-continued

| Cmp. ID<br>Synthetic Method | Structure<br>MS (M + H)+<br>1H NMR |
|---|---|

089_S
General procedure A
A01B05C01D05

459/461

1H NMR (400 MHz, CD3OD) δ 8.45 (s, 2 H), 7.59 (d, J = 4.77 Hz, 1 H), 7.30 (br. s., 1 H), 7.12-7.20 (m, 1 H), 4.02 (br. s., 2 H), 3.87 (dd, J = 14.81, 5.52 Hz, 1 H), 3.34-3.41 (m, 2 H), 3.21-3.31 (m, 2 H), 2.32 (d, J = 5.77 Hz, 1 H), 1.93 (dd, J = 14.68, 6.90 Hz, 1 H), 1.73 (br. s., 1 H), 0.95 (d, J = , 6.02 Hz, 6 H).

090

091

507/509

092
General procedure A
A01B08C01D05

431/433

1H NMR (400 MHz, CD3OD) δ 8.41 (s, 2 H), 7.64 (dd, J = 6.78, 2.51 Hz, 1 H), 7.36 (dt, J = 9.03, 3.39 Hz, 1 H), 7.17 (t, J = 8.91 Hz, 1 H), 4.34 (br. s., 1 H), 4.05 (d, J = 14.30 Hz, 1 H), 3.46-3.56 (m, 2 H), 3.35-3.41 (m, 3 H), 2.25-2.36 (m, 1 H), 1.90-2.02 (m, 1 H), 1.26 (d, J = 6.27 Hz, 3 H).

093

TABLE 1-continued

| Cmp. ID Synthetic Method | Structure MS (M + H)+ ¹H NMR |
|---|---|
| 094 | |
| 095 | |
| 096 | |
| 097 General procedure A A01B13C01D05 | 431/433 |

¹H NMR (400 MHz, MeOD) δ 8.46 (s, 2 H), 7.11-7.61 (m, 3 H), 3.97-4.11 (m, 2 H), 3.05-3.67 (m, 8 H), 2.17-2.31 (m, 1 H), 0.93 (d, J = 6.8 Hz, 3H).

TABLE 1-continued
| Cmp. ID Synthetic Method | Structure MS (M + H)+ ¹H NMR |
|---|---|
098
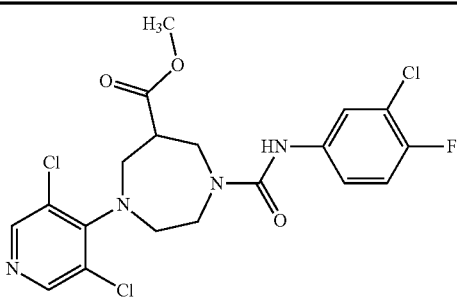
475/477
¹H NMR (400 MHz, CD3OD) δ 8.49 (s, 2H), 7.61-7.63 (s, 1H), 7.30-7.32 (m, 1H), 7.16-7.20 (m, 1H), 4.05-4.30 (m, 2H), 3.89-3.94 (m, 2H), 3.68-3.75 (m, 2H), 3.60 (s, 3H), 3.25-3.30 (m, 2H), 3.11-3.13 (m, 1H).
099
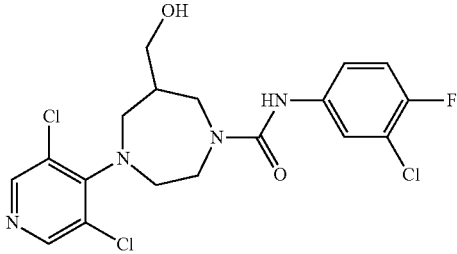
447/449
¹H NMR (400 MHz, CDCl3) δ 8.46 (s, 2H), 7.57-7.59 (s, 1H), 7.28-7.30 (m, 1H), 7.05-7.09 (m, 1H), 3.80-4.21 (m, 2H), 3.67-3.81 (m, 3H), 3.40-3.51 (m, 5H), 3.11-3.17 (m, 1H), 2.30-2.32 (m, 1H)
100
General procedure A
A01B16C01D05
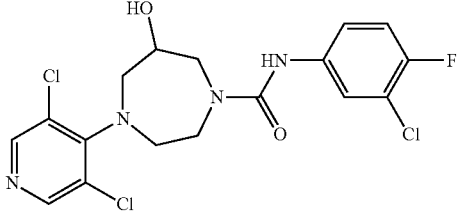
433/435
¹H NMR (400 MHz, MeOD) δ 8.49 (s, 2 H), 7.59 (d, J = 6.8 HZ, 1 H), 7.12-7.31 (m, 2 H), 3.82-4.21 (m, 3 H), 3.15-3.61 (m, 6 H).
101
General procedure A
A01B17C01D05
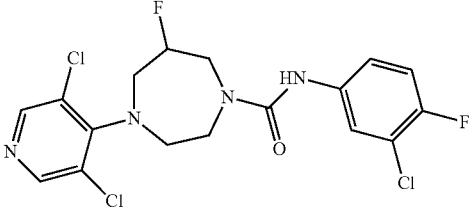
435/437
¹H NMR (400 MHz, MeOD) δ 8.43 (s, 2 H), 7.12-7.65 (m, 3 H), 4.52-4.79 (m, 3 H), 3.75-4.16 (m, 6 H).

TABLE 1-continued

| Cmp. ID Synthetic Method | Structure MS (M + H)+ ¹H NMR |
|---|---|

102
General procedure A
A01B18C01D05

465/467

¹H NMR (400 MHz, MeOD) δ 8.53 (s, 2 H), 7.05-7.67 (m, 7 H), 3.62-3.85 (m, 2 H), 3.32 (s, 2H), 2.05-2.17 (m, 2 H).

103
General procedure A
A01B20C01D05

465/467

¹H NMR (400 MHz, MeOD) δ 8.62 (s, 2 H), 7.05-7.67 (m, 7 H), 3.62-3.85 (m, 2 H), 3.32 (s, 2H), 2.05-2.17 (m, 2 H).

104

105

106
General procedure H
A01B23C01D20

316/318

1H NMR (400 MHz, CDCl₃) δ 8.43 (s, 2H), 3.30-3.46 (m, 3H), 3.24 (t, d, J = 4.0 Hz, 13.5 Hz, 1H), 3.07-3.16 (m, 4H), 2.99 (s, 3H), 1.81-2.07 (m, 5H), 1.68-1.79 (m, 1H)

TABLE 1-continued

| Cmp. ID<br>Synthetic Method | Structure<br>MS (M + H)+<br>¹H NMR |
|---|---|

107

411/413

¹H NMR (400 MHz, CD3OD) δ 8.36 (s, 2H), 8.32 (s, 1H), 7.65-7.67 (m, 1H), 7.33-7.36 (m, 1H), 7.15-7.19 (m, 1H), 3.75-3.78 (m, 2H), 3.35-3.37 (m, 2H), 2.75-2.81 (m, 2H), 1.94-1.99 (m, 1H), 1.21-1.24 (m, 1H).

108

393/395

109

423/425

¹H NMR (400 MHz, CD3OD) δ 8.31 (s, 2H), 7.99 (s, 1H), 7.63-7.65 (m, 1H), 7.30-7.33 (m, 1H), 7.14-7.19 (m, 1H), 3.76-3.81 (m, 4H), 3.44-3.48 (m, 4H), 2.17-2.21 (m, 1H), 1.96-2.00 (m, 2H), 1.00-1.04 (m, 2H), 0.76-0.78 (m, 2H).

110

405/407

¹H NMR (400 MHz, CD3OD) δ 8.30 (s, 2H), 7.78 (s, 1H), 7.57-7.58 (m, 1H), 7.31-7.34 (m, 1H), 7.24-7.28 (m, 1H), 7.02-7.05 (m, 1H), 3.76-3.83 (m, 4H), 3.45-3.48 (m, 4H), 2.17-2.22 (m, 1H), 1.98-2.02 (m, 2H), 0.99-1.02 (m, 2H), 0.75-0.78 (m, 2H).

TABLE 1-continued

| Cmp. ID
Synthetic Method | Structure
MS (M + H)+
1H NMR |
|---|---|
| 111 | |
| 112 | |
| 113 | |
| 114 | |
| 115 | |
| 116 | |

TABLE 1-continued

| | Structure |
|---|---|
| Cmp. ID | MS (M + H)+ |
| Synthetic Method | ¹H NMR |

117

[Structure: 3-pyridylmethyl and chloro-substituted pyridine linked to diazepane carboxamide with 3-chloro-4-fluorophenyl]

118

[Structure: 3-pyridylmethyl and chloro-substituted pyridine linked to diazepane carboxamide with 3-chlorophenyl]

119
General procedure L
A01B34C01D01

[Structure: 3,5-dichloropyridine linked to diazabicyclic carboxamide with phenyl]

391/393

¹H NMR (400 MHz, CD₃OD) δ 8.45 (s, 2H), 7.43-7.45 (m, 2H), 7.27-7.31 (m, 2H), 7.03-7.07 (m, 1H), 4.58-4.59 (m, 2H), 3.80 (dd, J = 2.7 Hz, 12.2 Hz, 1H), 3.28-3.30 (m, 2H), 2.97 (d, J = 12.4 Hz, 1H), 2.19-2.32 (m, 5H), 1.92-1.94 (m, 1H).

120
General procedure L
A01B34C01D04

[Structure: 3,5-dichloropyridine linked to diazabicyclic carboxamide with 3,4-difluorophenyl]

427/429

121
General procedure L
A01B34C01D05

[Structure: 3,5-dichloropyridine linked to diazabicyclic carboxamide with 3-chloro-4-fluorophenyl]

443/445

TABLE 1-continued
| Cmp. ID<br>Synthetic Method | Structure<br>MS (M + H)+<br>$^1$H NMR |
|---|---|
| 122<br>General procedure L<br>A01B35C01D01 | 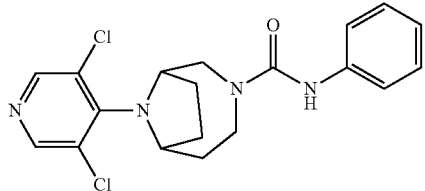 [SMILES: O=C(Nc1ccccc1)N1CCC2CCC1CN2c1c(Cl)cncc1Cl]<br>391/393 |
| 123<br>General procedure L<br>A01B35C01D04 | 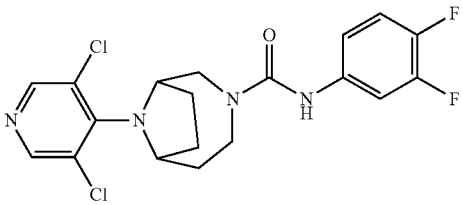 [SMILES: O=C(Nc1ccc(F)c(F)c1)N1CCC2CCC1CN2c1c(Cl)cncc1Cl]<br>427/429 |
| 124<br>General procedure L<br>A01B35C01D05 | 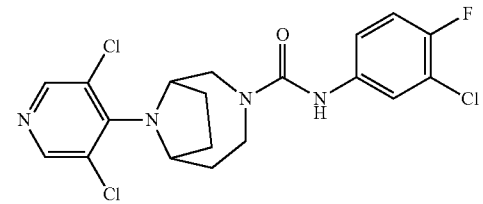 [SMILES: O=C(Nc1ccc(F)c(Cl)c1)N1CCC2CCC1CN2c1c(Cl)cncc1Cl]<br>443/445<br>$^1$H NMR (400 MHz, CD$_3$OD) δ 8.39 (s, 2H), 7.61 (dd, J = 2.8 Hz, 6.8 Hz, 1H), 7.30-7.32 (m, 1H), 7.16 (t, J = 8.8 Hz, 1H), 4.35-4.40 (m, 1H), 4.22-4.24 (m, 1H), 4.15 (d, J = 14.4 Hz, 1H), 3.98-4.02 (m, 1H), 3.82-3.85 (m, 1H), 3.48-3.52 (dd, 1H), 2.39-2.43 (m, 1H), 2.16-2.22 (m, 2H), 1.77-1.93 (m, 3H). |
| 125<br>General procedure A<br>A01B19C01D05 | 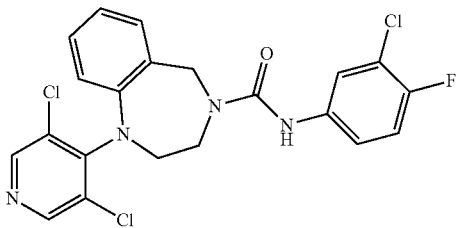<br>465/467 |
| 126 | 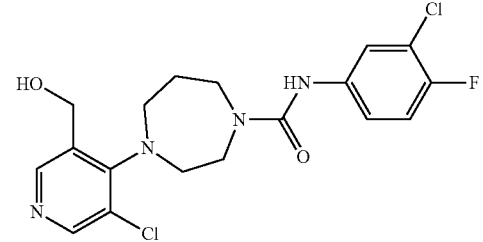 [SMILES: O=C(Nc1ccc(F)c(Cl)c1)N1CCCN(c2c(Cl)cncc2CO)CC1] |

TABLE 1-continued

| Cmp. ID<br>Synthetic Method | Structure<br>MS (M + H)+<br>1H NMR |
|---|---|
| 127 | [Structure: pyridine with Cl, CH3-O-CH2- substituent, connected to diazepane-carboxamide-N-(3-chloro-4-fluorophenyl)] |
| 128 | [Structure: pyridine with Cl, HO-CH2CH2- substituent, connected to diazepane-carboxamide-N-(3-chloro-4-fluorophenyl)] |
| 129 | [Structure: pyridine with Cl, CH3-O-CH2CH2- substituent, connected to diazepane-carboxamide-N-(3-chloro-4-fluorophenyl)] |
| 130<br>General procedure M<br>A01B36C01D05 | [Structure with H3C-O- on diazepane, 3,5-dichloropyridinyl, N-(3-chloro-4-fluorophenyl)carboxamide]<br>447/449 |
| 131<br>General procedure M<br>A01B37C01D05 | [Structure with H3C-CH2-O- on diazepane, 3,5-dichloropyridinyl, N-(3-chloro-4-fluorophenyl)carboxamide]<br>461/463 |

1H NMR (400 MHz, CD3OD) δ 8.47 (s, 2H), 7.32 (s, 5H), 7.17-7.27 (m, 1H), 6.89-7.03 (m, 1H), 6.67-6.81 (m, 1H), 4.50-4.58 (m, 2H), 3.87-4.29 (m, 4H), 3.63-3.76 (m, 1H), 3.45 (dd, J = 7.53, 14.81 Hz, 3H), 3.22-3.29 (m, 1H)

TABLE 1-continued

| Cmp. ID<br>Synthetic Method | Structure<br>MS (M + H)+<br>$^1$H NMR |
|---|---|
| 132<br>General procedure M<br>A01B38C01D05 | 523/525 |

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O, and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

Methods of the Invention

The invention provides a method of treatment of an HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention also provides a method of reducing viral load associated with an HBV infection in an individual in need thereof, comprising administering to the individual a therapeutically effective amount of a compound of the invention.

The invention further provides a method of reducing reoccurrence of an HBV infection in an individual in need thereof, comprising administering to the individual a therapeutically effective amount of a compound of the invention.

The invention also provides a method of reducing the physiological impact of an HBV infection in an individual in need thereof, comprising administering to the individual a therapeutically effective amount of a compound of the invention.

The invention further provides a method of reducing, slowing, or inhibiting an HBV infection in an individual in need thereof, comprising administering to the individual a therapeutically effective amount of a compound of the invention.

The invention also provides a method of inducing remission of hepatic injury from an HBV infection in an individual in need thereof, comprising administering to the individual a therapeutically effective amount of a compound of the invention.

The invention further provides a method of reducing the physiological impact of long-term antiviral therapy for HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention further provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated.

In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent compared to the extent that other therapeutic classes of HBV drugs reduce viral load in the individual.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of compound of Formula Ia, or a pharmaceutically acceptable salt thereof.

In another embodiment, provided herein is a method of treating an HBV infection in an individual in need thereof, comprising administering to the individual a therapeutically effective amount of compound of Formula II, or a pharmaceutically acceptable salt thereof.

In another embodiment, provided herein is a method of treating an HBV infection in an individual in need thereof, comprising administering to the individual a therapeutically effective amount of compound of Formula IIa, or a pharmaceutically acceptable salt thereof.

In another embodiment, provided herein is a method of treating an HBV infection in an individual in need thereof, comprising administering to the individual a therapeutically effective amount of compound of Formula III, or a pharmaceutically acceptable salt thereof.

In another embodiment, provided herein is a method of treating an HBV infection in an individual in need thereof, comprising administering to the individual a therapeutically effective amount of compound of Formula IV, or a pharmaceutically acceptable salt thereof.

In another embodiment, provided herein is a method of treating an HBV infection in an individual in need thereof, comprising administering to the individual a therapeutically effective amount of compound of Formula V, or a pharmaceutically acceptable salt thereof.

Accordingly, in one embodiment, provided herein is a method of treating an HBV infection in an individual in need thereof, comprising administering to the individual a therapeutically effective amount of compound 005.

Accordingly, in one embodiment, provided herein is a method of treating an HBV infection in an individual in need thereof, comprising administering to the individual a therapeutically effective amount of compound 010.

Accordingly, in one embodiment, provided herein is a method of treating an HBV infection in an individual in need thereof, comprising administering to the individual a therapeutically effective amount of compound 044.

Accordingly, in one embodiment, provided herein is a method of treating an HBV infection in an individual in need thereof, comprising administering to the individual a therapeutically effective amount of compound 045.

Accordingly, in one embodiment, provided herein is a method of treating an HBV infection in an individual in need thereof, comprising administering to the individual a therapeutically effective amount of compound 091.

Accordingly, in one embodiment, provided herein is a method of treating an HBV infection in an individual in need thereof, comprising administering to the individual a therapeutically effective amount of compound 092.

Accordingly, in one embodiment, provided herein is a method of treating an HBV infection in an individual in need thereof, comprising administering to the individual a therapeutically effective amount of compound 098.

Accordingly, in one embodiment, provided herein is a method of treating an HBV infection in an individual in need thereof, comprising administering to the individual a therapeutically effective amount of compound 099.

Accordingly, in one embodiment, provided herein is a method of treating an HBV infection in an individual in need thereof, comprising administering to the individual a therapeutically effective amount of compound 100.

Accordingly, in one embodiment, provided herein is a method of treating an HBV infection in an individual in need thereof, comprising administering to the individual a therapeutically effective amount of compound 107.

Accordingly, in one embodiment, provided herein is a method of treating an HBV infection in an individual in need thereof, comprising administering to the individual a therapeutically effective amount of compound 108.

Accordingly, in one embodiment, provided herein is a method of treating an HBV infection in an individual in need thereof, comprising administering to the individual a therapeutically effective amount of compound 109.

Accordingly, in one embodiment, provided herein is a method of treating an HBV infection in an individual in need thereof, comprising administering to the individual a therapeutically effective amount of compound 110.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as, but not limited to BAY 41-4109;

compounds of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member of the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In one embodiment, the additional therapeutic agent is a TLR modulator such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl]acetate).

In any of the methods provided herein, the method may further comprise administering to the individual at least one HBV vaccine, a nucleoside HBV inhibitor, an interferon or any combination thereof. In an embodiment, the HBV vaccine is at least one of Recombivax HB®, Engerix-B®, Elovac B®, GeneVac-B®, or Shanvac B®.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a HBV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HBV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat HBV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in a range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Library General Design

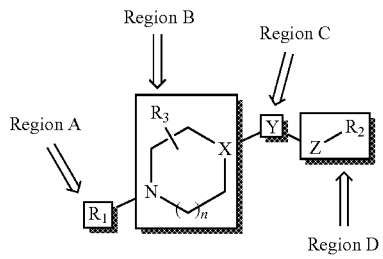

Region A:

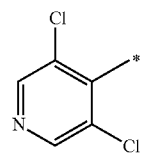 A01

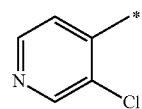 A02

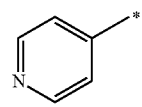 A03

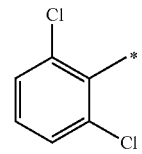 A04

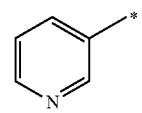 A05

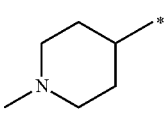 A06

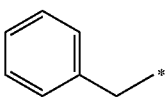 A07

-continued

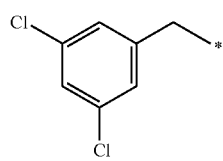 A08

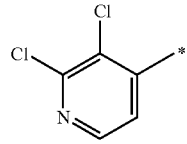 A09

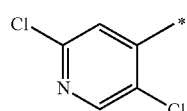 A10

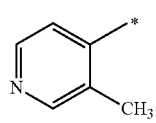 A11

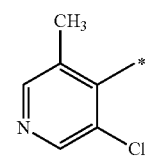 A12

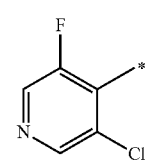 A13

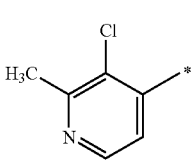 A14

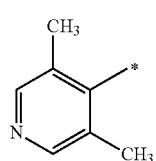 A15

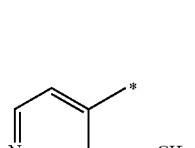 A16

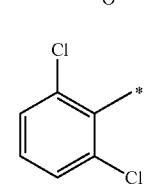 A17

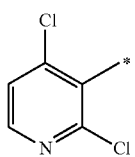
A18
Region B:
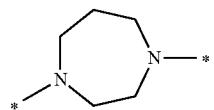
B01
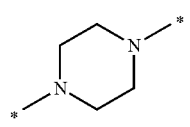
B02
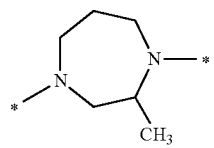
B03
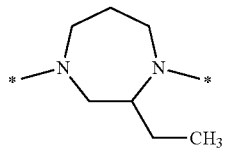
B04
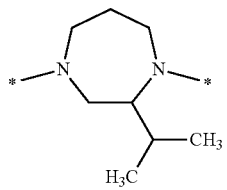
B05
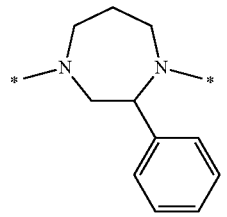
B06
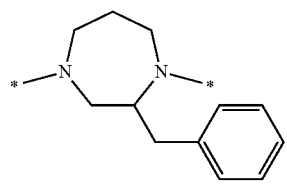
B07
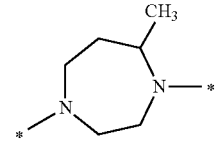
B08
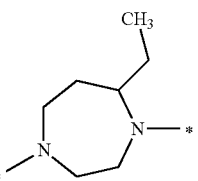
B09
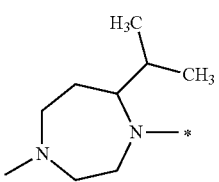
B10
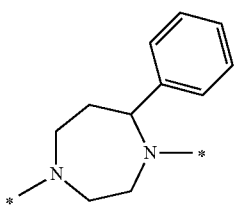
B11
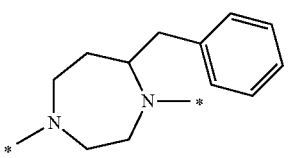
B12
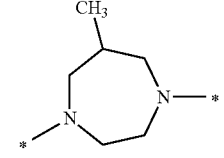
B13
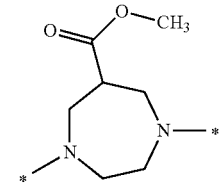
B14
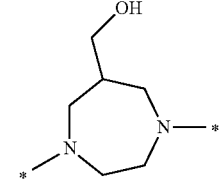
B15
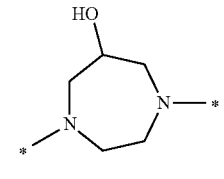
B16

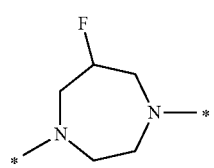 B17
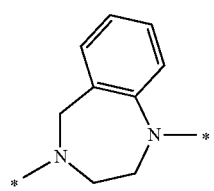 B18
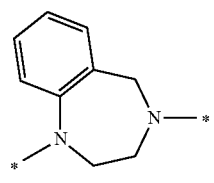 B19
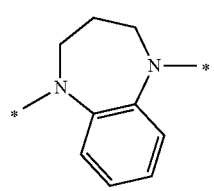 B20
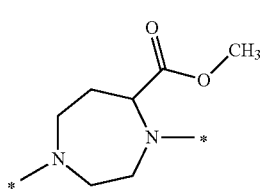 B21
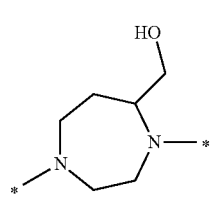 B22
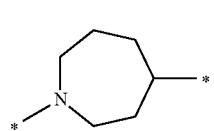 B23
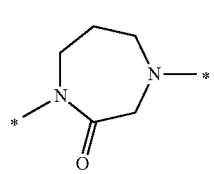 B24
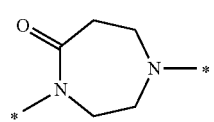 B25
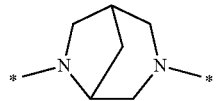 B26
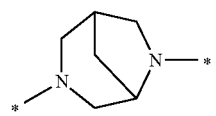 B27
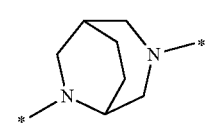 B28
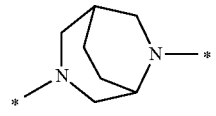 B29
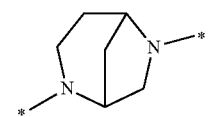 B30
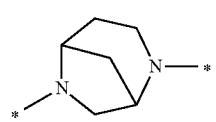 B31
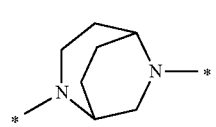 B32
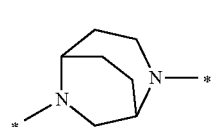 B33
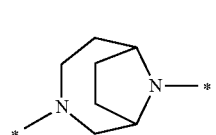 B34
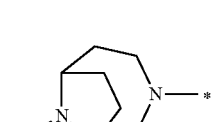 B35
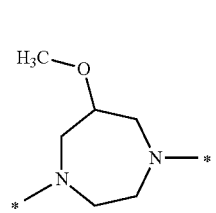 B36

-continued
B37 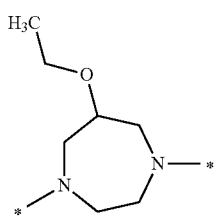
B38 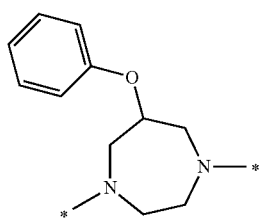
Region C:
C01 
C02 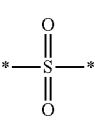
Region D:
D01 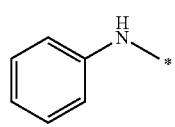
D02 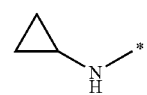
D03 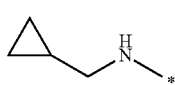
D04 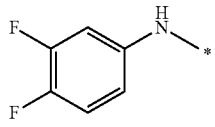
D05 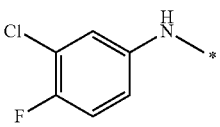
D06 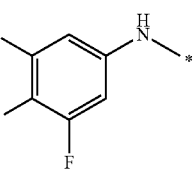
D07 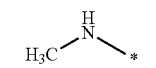
D08 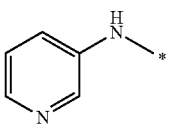
D09 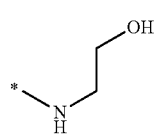
D10 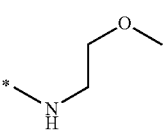
A11 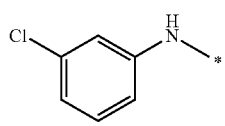
D12 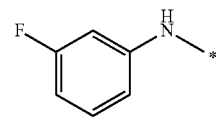
D13 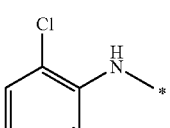
D14 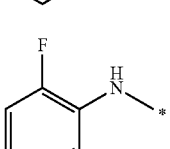
D15 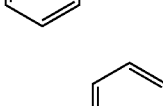
D16 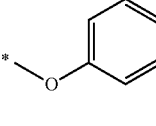
D17 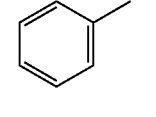

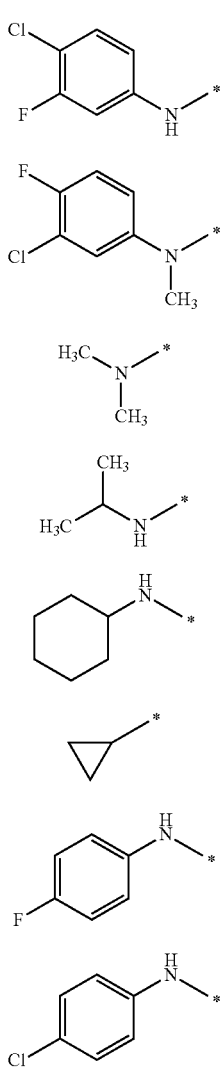

Part I Intermediate Synthesis (Regions A and B)

1 Preparation of Region A Intermediates
1.1 Preparation of A09

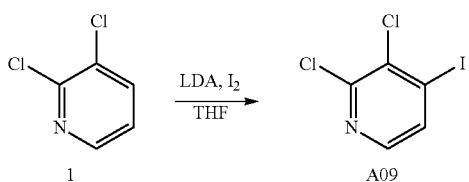

To a solution of LDA in dry THF (40 mmol, 50 mL) at −78° C., a solution of compound 1 (5.0 g, 34.0 mmol) in THF (30 mL) was added dropwise. After addition, the reaction mixture was stirred for 0.5 h at −78° C. Then a solution of I₂ (10 g, 40 mmol) in THF (10 mL) was added dropwise at −78° C. The resulting mixture was stirred at rt for 2 h. Aqueous NH₄Cl (50 mL) was added to quench the reaction. The mixture was extracted with EA (ethyl acetate) (300 mL). The combined organic layer was dried and concentrated in vacuo. The residue was purified by column chromatography on silica gel (PE:EA=50:1) to give the product, A09 (4.3 g, 46.5%) as white solid. LCMS: 274/276 [M+1].

1.2 Preparation of A13

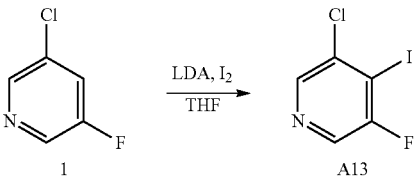

To a solution of LDA in dry THF (12 mmol, 20 mL) at −78° C., a solution of compound 1 (1.3 g, 1.0 mmol) in THF (30 mL) was added dropwise. After addition, the reaction mixture was stirred for 0.5 h at −78° C. Then a solution of I₂ (3.8 g, 1.5 mmol) in THF (10 mL) was added dropwise at −78° C. The resulting mixture was stirred at rt for 2 h. Aqueous NH₄Cl (50 mL) was added to quench the reaction. The mixture was extracted with EA (300 mL). The combined organic layer was dried and concentrated in vacuo. The residue was purified by column chromatography on silica gel (PE:EA=50:1) to give the product, A13 (2.1 g, yield: 84%). LCMS: 258/260 [M+1].

1.3 Preparation of A16

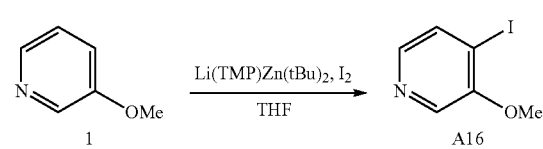

ZnCl₂ (540 mg, 4 mmol) was dissolved in THF (10 mL) and cooled to −78° C. under N₂ atmosphere. t-BuLi (5.6 mL, 8 mmol) was added dropwise and the solution was allowed to stir at −78° C. for 40 min. In a separated vial containing TMPH (4 mmol) and THF (10 mL), n-BuLi (4 mmol) was added dropwise at −78° C. and the solution was allowed to stir for 40 min reaching rt. Then LiTMP solution was introduced to the in situ t-Bu₂Zn solution at −78° C., stirred for 30 min and warmed gradually to 0° C. Compound 1 (436 mg, 4 mmol) was added and the resulting mixture stirred at rt for 2 h. Then the mixture was cooled to 0° C. and I₂ (1 g, 4 mmol) in THF (10 mL) was added and stirred for 1 h. A 10% solution of Na₂S₂O₃ was added and the mixture was extracted with EA. The organic layer was dried and concentrated to give the crude product, and purified by column to give the product, A1. (185 mg, yield: 19%). LCMS: 236[M+1].

2 Preparation of Region B Intermediates
Preparation of B03

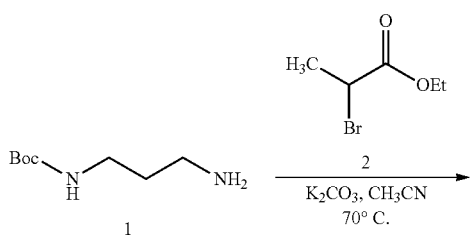

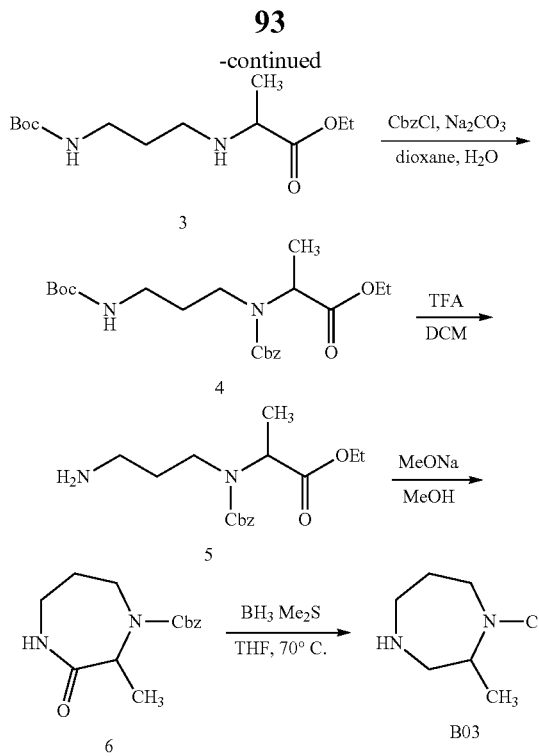

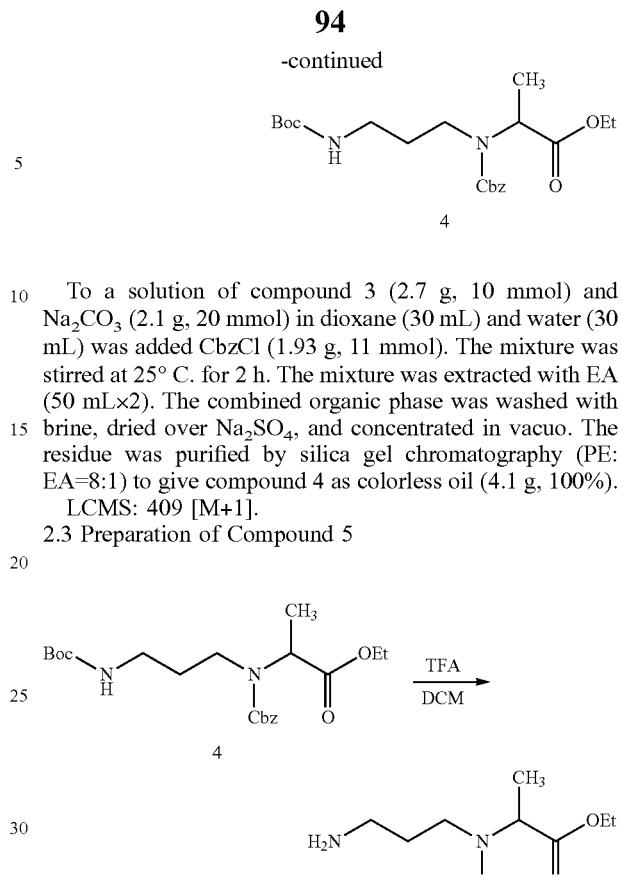

2.1 Preparation of Compound 3

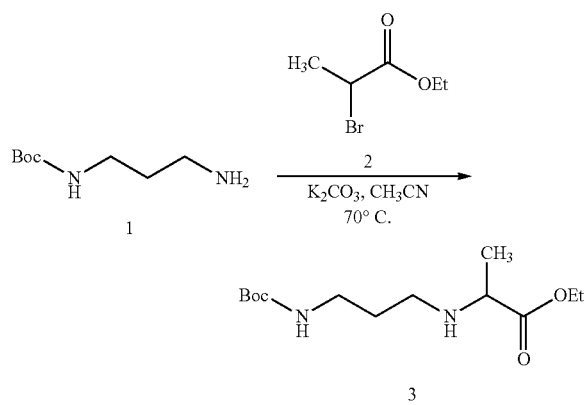

To a solution of compound 1 and K₂CO₃ (4.2 g, 30 mmol) (3.8 g, 22 mmol) in CH₃CN (100 mL) was added compound 2 (3.6 g, 20 mmol). The mixture was heated to 80° C. and stirred for 2 h. The mixture was concentrated in vacuo. The residue was purified by silica gel chromatography (PE: EA=2:1) to give compound 3 as colorless oil (2.7 g, 50.2%).

LCMS: 275 [M+1].

2.2 Preparation of Compound 4

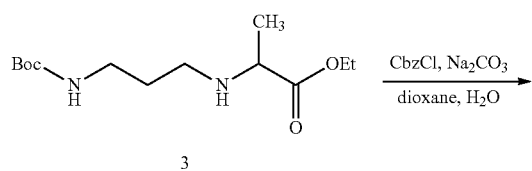

To a solution of compound 3 (2.7 g, 10 mmol) and Na₂CO₃ (2.1 g, 20 mmol) in dioxane (30 mL) and water (30 mL) was added CbzCl (1.93 g, 11 mmol). The mixture was stirred at 25° C. for 2 h. The mixture was extracted with EA (50 mL×2). The combined organic phase was washed with brine, dried over Na₂SO₄, and concentrated in vacuo. The residue was purified by silica gel chromatography (PE: EA=8:1) to give compound 4 as colorless oil (4.1 g, 100%). LCMS: 409 [M+1].

2.3 Preparation of Compound 5

To a solution of compound 4 (4.1 g, 10 mmol) in DCM (30 mL) was added CF₃CO₂H (30 mL). The mixture was stirred at 30° C. for 2 h. The mixture was concentrated in vacuo. The residue was adjusted pH to 8 with a saturated NaHCO₃, and then extracted with DCM. The combined organic phase was washed with brine, dried over Na₂SO₄, and concentrated in vacuo to give compound 5 as colorless oil (3.1 g, 100%) which was used for the next step without purification. LCMS: 309 [M+1].

2.4 Preparation of Compound 6

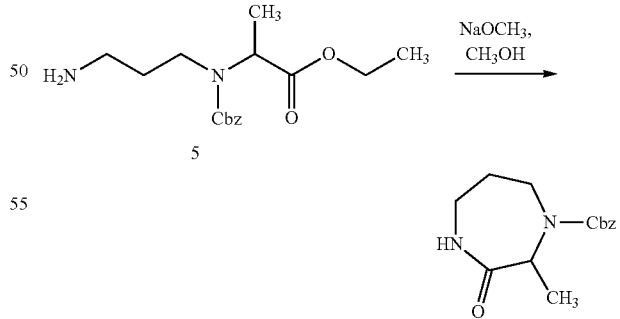

To a solution of compound 5 (3.1 g, 10 mmol) in MeOH (50 mL) was added NaOCH₃ (1.62 g, 30 mmol). The mixture was stirred at 30° C. for 12 h. The mixture was neutralized with 1 N HCl and concentrated in vacuo. The combined organic phase was washed with brine, dried over Na₂SO₄, and concentrated in vacuo. The residue was purified by silica gel chromatography (DCM:MeOH=20:1) to give compound 6 as colorless oil (2.1 g, yield: 79%). LCMS: 309 [M+1].

2.5 Preparation of B03

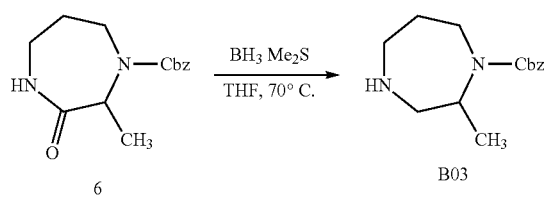

Compound 6 (1.3 g, 5 mmol) was dissolved in THF (20 mL), then BH₃-Me₂S (1 mL, 10 mmol) was added. The mixture was heated to 60° C. and stirred for 5 h. 2 N HCl (3 mL) was added and the mixture was refluxed for 30 min. The mixture was concentrated in vacuo. The residue was neutralized with NaHCO₃, and extracted with EA. The combined organic phase was washed with brine, dried over Na₂SO₄, and concentrated in vacuo. The residue was was purified by silica gel chromatography (DCM:MeOH=10:1) to give compound B03 as yellow solid (750 mg, yield: 60.2%). LCMS: 249 [M+1].

Preparation of B20

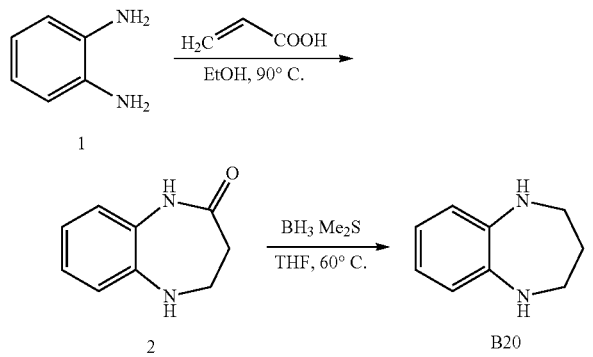

2.6 Preparation of Compound 2

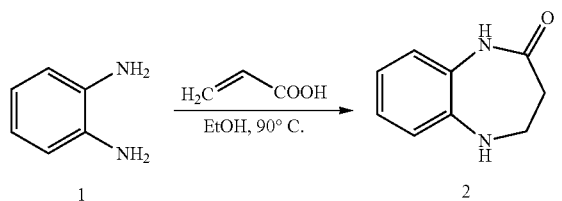

A solution of compound 1 (10.8 g, 100 mmol) and acrylic acid (10.8 g, 150 mmol) in EtOH (300 mL) was heated to 90° C. for 24 h. The mixture was concentrated in vacuo. The residue was purified by silica gel chromatography (PE: EA=2:1) to give compound 2 as yellow solid (6.9 g, yield: 42.5%). LCMS: 163 [M+1].

2.7 Preparation of Compound B20

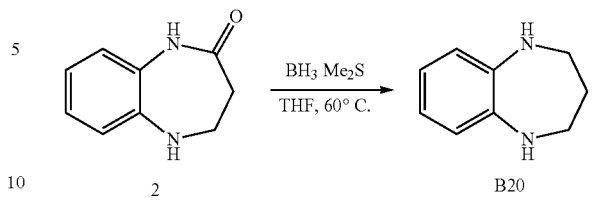

To a solution of compound 2 (3.3 g, 20 mmol) in THF (50 mL) was added BH₃-Me₂S (3 mL, 30 mmol). The mixture was heated to 60° C. for 5 h. The mixture was concentrated in vacuo. The residue was purified by silica gel chromatography (PE:EA=1:1) to give B20 as yellow solid (2.1 g, yield: 73.9%). ¹H NMR (400 MHz, CDCl₃): δ ppm: 6.85-6.71 (m, 4H), 3.09-2.97 (m, 4H), 1.95-1.86 (m, 2H). LCMS: 149 [M+1].

Preparation of B16/17

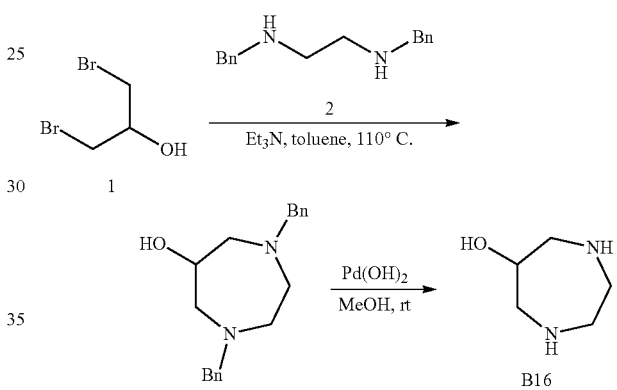

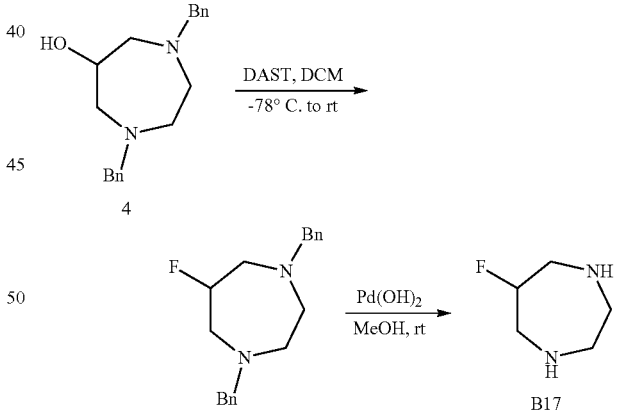

2.8 Preparation of Compound 3

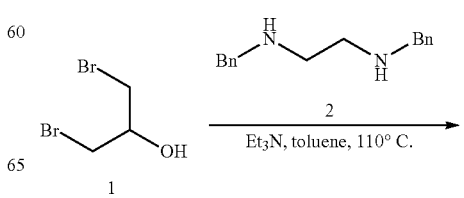

-continued

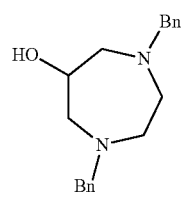

2.11 Preparation of B17

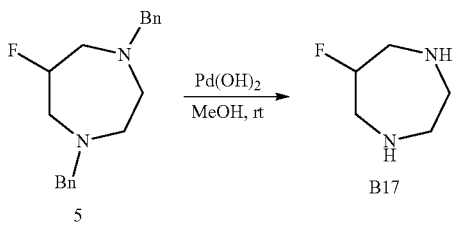

To a solution of compound 1 (12.37 g, 56.5 mmol) and compound 2 (13.56 g, 56.5 mmol) in toluene (800 mL) was added Et$_3$N (17.17 g, 170 mmol). The mixture was heated to 120° C. for 48 h. The mixture was concentrated in vacuo. The residue was purified by silica gel chromatography (PE:EA=2:1) to give compound 3 as yellow solid (6.9 g, 41.2%). $^1$H NMR (400 MHz, CDCl$_3$): δ ppm: 7.47-7.21 (m, 10H), 3.87-3.61 (m, 5H), 2.97-2.41 (m, 8H).

LCMS: 297 [M+1].

2.9 Preparation of B16

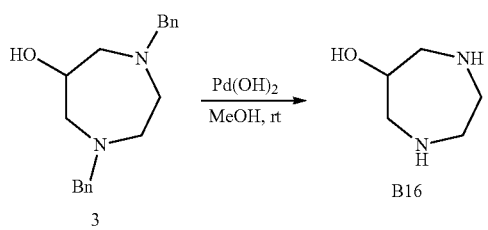

A mixture of compound 3 (2.2 g, 7.5 mmol) and Pd(OH)$_2$/C (500 mg) in MeOH (80 mL), was hydrogenated overnight under H$_2$ balloon atmosphere. The catalyst was filtered and the filtrate was concentrated to give the desired product B16 (0.8 g, 100%) as colorless oil. $^1$H NMR (400 MHz, MeOD): δ ppm: 3.89-3.71 (m, 1H), 2.97-2.63 (m, 8H).

2.10 Preparation of Compound 5

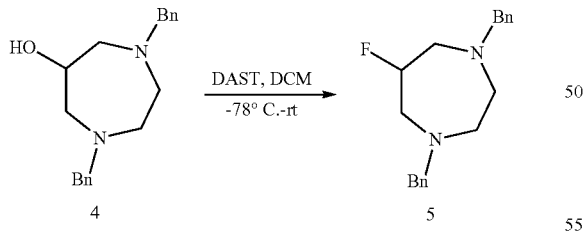

To a solution of compound 4 (2.97 g, 10 mmol) in DCM (50 mL) was added DAST (1.94 g, 12 mmol) at −78° C. under N$_2$ atmosphere. The mixture was warmed back to 20° C. and stirred for 2 h. The mixture was quenched with saturated NaHCO$_3$ (50 mL), and extracted with DCM. The combined organic phase was washed with brine, dried over Na$_2$SO$_4$, and concentrated in vacuo. The residue was purified by silica gel chromatography (PE:EA=5:1) to give compound 5 as white solid (2.3 g, 77.2%). LCMS: 299 [M+1].

To a mixture of compound 5 (1.5 g, 5 mmol) in MeOH (80 mL), Pd(OH)$_2$/C (500 mg) was added. The mixture was hydrogenated overnight under H$_2$ balloon atmosphere. The catalyst was filtered and the filtrate was concentrated to give the desired product B17 (510 mg, 98%) as colorless oil. $^1$H NMR (400 MHz, MeOD): δ ppm: 4.51-4.11 (m, 1H), 2.97-2.63 (m, 8H).

Preparation of B23

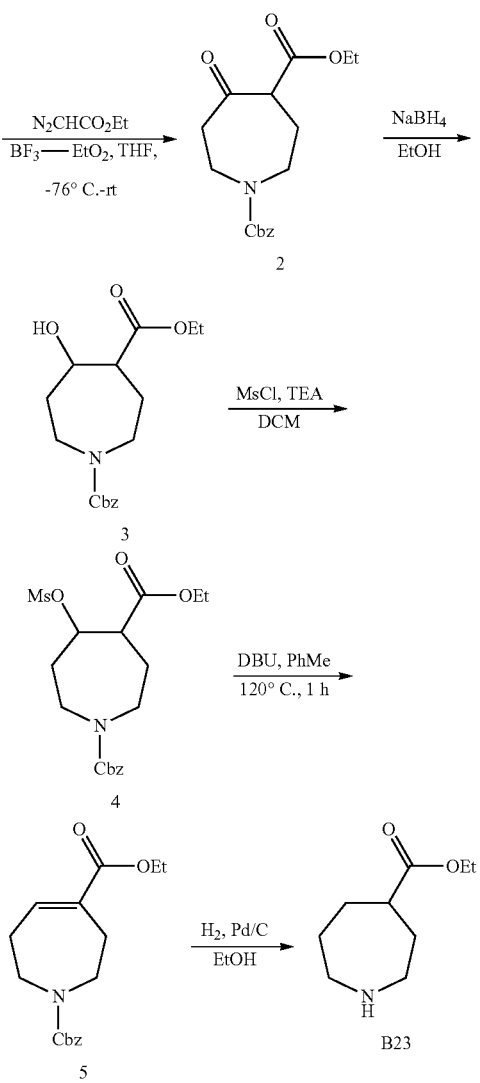

2.12 Preparation of Compound 2

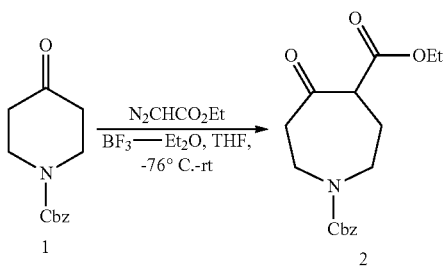

To a solution of compound 1 (15.0 g, 64.5 mmol) in THF (130 mL) was added N₂CH₂COOEt (8.79 mL, 84.0 mmol) and followed by BF₃-Et₂O (8.1 mL, 64.5 mmol) at −78° C. The mixture was stirred at −78° C. for 1 h, then warmed back to 25-30° C. for another 1 h to give a clear yellow solution. The mixture was added a saturated aqueous solution of K₂CO₃ dropwise until no gas evolution was observed. The mixture was concentrated to remove solvents. The aqueous layer was extracted with DCM (100 mL×4). The combined organic layer was dried over Na₂SO₄, and concentrated in vacuo. The residue was purified by silica gel chromatography (PE:EA=30:1 to PE:EA=12:1) to give the desired compound 2 (14.8 g, 70.4%) as a yellow oil. ¹H NMR (400 MHz, CDCl₃): δ ppm: 7.45-7.31 (m, 5H), 5.23-5.06 (m, 2H), 4.29-4.17 (m, 2H), 3.98-3.70 (m, 3H), 3.69-3.36 (m, 6H), 2.97-2.43 (m, 2H), 2.18-1.98 (m, 2H), 1.66 (s, 2H), 1.38-1.23 (m, 4H). LCMS: 320 [M+1].

2.13 Preparation of Compound 3

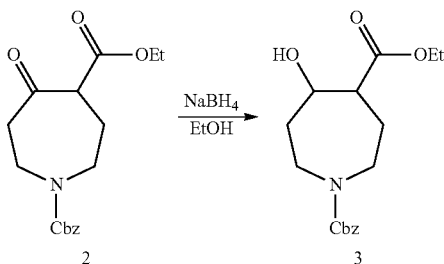 [SMILES: "EtOH" ; CCOC(=O)C1CCN(C(=O)OCc2ccccc2)CCC1=O ; "NaBH4" ; CCOC(=O)C1CCN(C(=O)OCc2ccccc2)CCC1O]

To a solution of Compound 2 (5.0 g, 15.6 mmol) in EtOH (50 mL) was added NaBH₄ (237 mg, 6.24 mmol) in portions at 0° C. The mixture was stirred at at 25° C. for 15 min. The mixture was neutralized with 1N aq HCl. The mixture was concentrated in vacuo to remove EtOH. The aqueous layer was extracted with DCM (50 mL×3). The combined organic layer was dried with Na₂SO₄, and concentrated in vacuo to give compound 3 (4.9 g, 97%) as a yellow oil.

¹H NMR (400 MHz, CDCl₃): δ ppm: 7.43-7.30 (m, 5H), 5.22-5.09 (m, 2H), 4.31-4.11 (m, 3H), 3.84-3.60 (m, 2H), 3.54-3.38 (m, 4H), 3.37-3.00 (m, 1H), 2.66-2.48 (m, 1H), 2.43-2.24 (m, 1H), 2.20-1.86 (m, 2H), 1.85-1.67 (m, 3H), 1.38-1.23 (m, 3H). LCMS: 322 [M+1].

2.14 Preparation of Compound 4

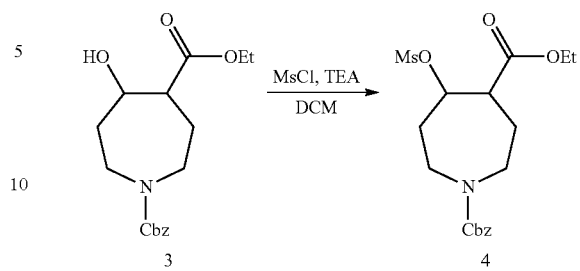

To a solution of Compound 3 (5.0 g, 15.6 mmol) and TEA (6.3 g, 62.4 mmol) in DCM (50 mL) was added MsCl (5.34 g, 46.8 mmol) at 0° C., and stirred at 25° C. under N₂ for 16 h. The mixture was washed with H₂O (20 mL). The organic layer was dried over Na₂SO₄, and concentrated to give desired compound 4 (6.5 g crude, yellow oil) which was used directly in the next step without further purification.

2.15 Preparation of Compound 5

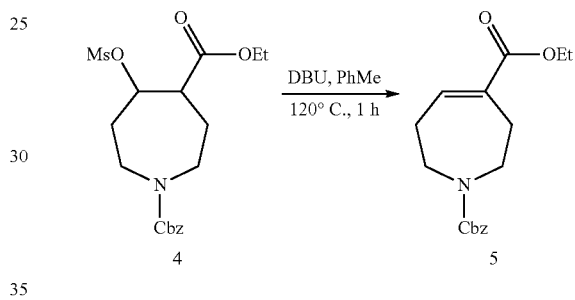

A solution of compound 4 (6.5 g, 16.3 mmol) and DBU (3.72 g, 24.5 mmol) in toluene (50 mL) was stirred at 120° C. for 5 h. TLC monitored that the reaction was completed. The mixture was adjusted pH to 6 with aq HCl (1N). Then the mixture was concentrated to remove solvents. The residue was dissolved in DCM (60 mL), and washed with H₂O. The combined organic layer was dried over Na₂SO₄, and concentrated in vacuo. The residue was purified through a silica gel column (PE:EA=50:1 to PE:EA=20:1) to give compound 5 (2.1 g, 43%) as a yellow oil. LCMS: 304[M+1].

2.16 Preparation of B23

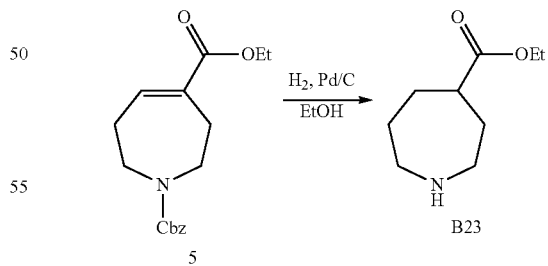

A mixture of compound 5 (2.1 g, 6.9 mmol) and Pd/C (0.4 g) in EtOH (25 mL) was stirred at 25° C. under H₂ (50 psi) for 24 h. The mixture was filtered and the filtrates were concentrated to give desired product B23 (1.1 g, 91%) as a colorless oil. ¹H NMR (400 MHz, CDCl₃): δ ppm: 4.24-4.08 (m, 2H), 3.51-3.34 (m, 1H), 3.32-3.03 (m, 3H), 3.01-2.80 (m, 1H), 2.80-2.68 (m, 1H), 2.44-2.29 (m, 1H), 2.20-2.03 (m, 2H), 2.03-1.91 (m, 2H), 1.90-1.76 (m, 1H), 1.27 (m, 4H)

Preparation of B24

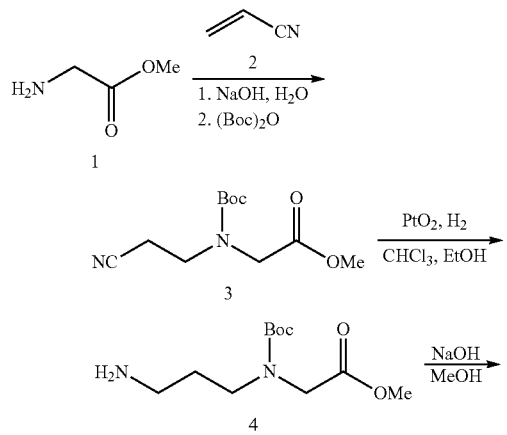

2.17 Preparation of Compound 3

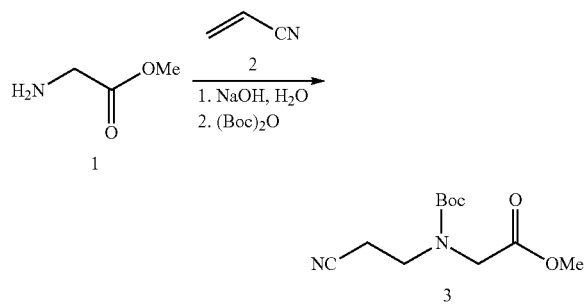

To a solution of compound 1 (5.0 g, 40.0 mmol) and NaOH (1.8 g, 45.0 mmol) in H₂ (80 mL) was added compound 2 (2.5 g, 50.0 mmol) at 0° C. The reaction mixture was heated to 75° C. for 3 h and then cooled to 25° C. (Boc)₂O (10.5 g, 50.0 mmol) was added and the mixture was continued to stir for 16 h. The formed mixture was diluted with water, and extracted with EA (100 mL×2). The organic layer was dried over Na₂SO₄ and concentrated in vacuo to give the crude product, which was purified by flash column chromatography to give the desired product (5.5 g, 57%). ¹H NMR (400 MHz, CDCl₃): δ ppm: 4.03 (s, 2H), 3.78-3.77 (m, 3H), 3.60-3.57 (m, 2H), 2.72-2.67 (m, 2H), 1.51-1.45 (m, 9H)

2.18 Preparation of Compound 4

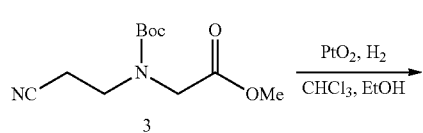

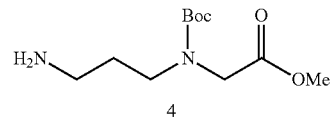

To a solution of compound 3 (2.8 g, 11.6 mmol) in EtOH—CHCl₃ (90 mL/2 mL) was added PtO₂ (560 mg). The formed mixture was hydrogenated at 25° C. for 16 h under 50 Psi pressure of H₂ atmosphere. The catalyst was filtered and the filtrate was concentrated to give the crude product, which was used in the next step directly (2.8 g, 98%). ¹H NMR (400 MHz, CDCl₃): δ ppm: 8.45-8.43 (m, 2H), 3.91-3.89 (m, 2H), 3.76-3.73 (m, 3H), 3.51-3.48 (m, 2H), 3.21-3.19 (m, 2H), 2.10-1.99 (m, 2H), 1.50-1.44 (m, 9H).

2.19 Preparation of B24

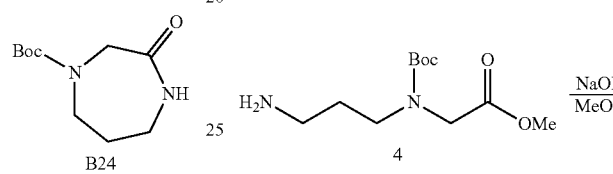

A solution of compound 4 (2.3 g, 9.3 mmol) in MeOH (20 mL) and NaOH (3N, 4 mL) was stirred at 25° C. for 2 h. TLC monitored that the reaction completed. The mixture was diluted with EA (150 mL) and washed with brine (100 mL). The organic layer was dried and concentrated to give the crude product, which was purified by column chromatography to give the desired product, B24 (1.25 g, 63%). ¹H NMR (400 MHz, CDCl₃): δ ppm: 4.10-4.05 (m, 2H), 3.60-3.58 (m, 2H), 3.31-3.28 (m, 2H), 1.91-1.85 (m, 2H), 1.63-1.45 (m, 9H).

Preparation of B26/27

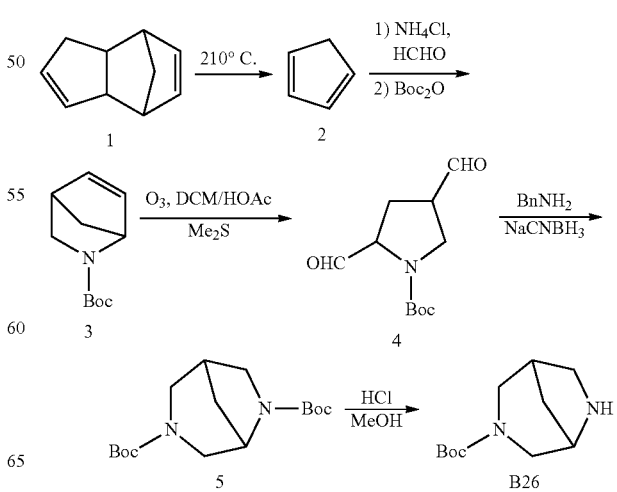

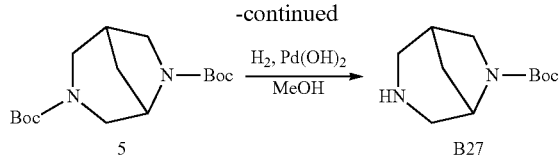

2.20 Preparation of Compound 2

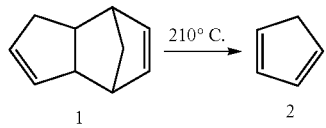 [SMILES: C1=CC2C3C=CC(C3)C2C1 ; C1=CCC=C1]

Compound 1 (80.4 g) was depolymerized at 210° C. and the mixture was distilled in vacuum (210° C., 0.1 MPa) to afford pure product (68.4 g, 84.5%) as colorless liquid.

2.21 Preparation of Compound 3

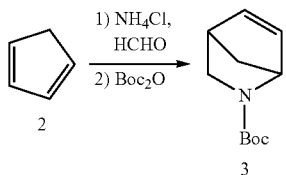 [SMILES: C1=CCC=C1 ; CC(C)(C)OC(=O)N1CC2C=CC1C2]

A solution of NH$_4$Cl (167 g, 3.09 mol) in water (500 mL) was added to aqueous formalin (125 mL, 1.54 mmol). Freshly distilled compound 2 (720 mg, 2 mmol) was added, and the mixture was stirred at rt for 3 days. The mixture was basified by 1M NaOH till pH around 9 and Boc$_2$O (224 g, 1.03 mmol) was added. Then the mixture was stirred at rt overnight. The mixture was extracted with (PE:EA=5:1), the organic layer was concentrated to give the crude product, which was purified by distilling followed by chromatography to give the pure product, compound 3 (9.1 g, 4.5%). $^1$H NMR (400 MHz, CDCl$_3$): δ ppm: 6.26 (s, 1H), 4.71 (d, J=5.5 Hz, 1H), 3.30 (dd, J=2.8 Hz, 8.8 Hz, 1H), 3.15 (s, 1H), 2.58-2.64 (m, 1H), 1.51-1.57 (m, 2H), 1.44 (s, 9H).

2.22 Preparation of Compound 4

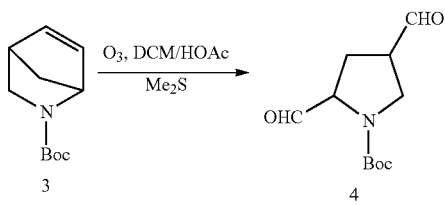 [SMILES: "Me2S" ; CC(C)(C)OC(=O)N1CC2C=CC1C2 ; CC(C)(C)OC(=O)N1CC(C=O)CC1C=O]

A stream of O$_3$ was bubbled through a solution of compound 3 (8.0 g, 41 mmol) in CH$_3$CO$_2$H (21 mL) and DCM (350 mL) at −50~60° C. until the solution turned blue. Excess O$_3$ was removed with O$_2$, and Me$_2$S (7.7 mL) was added dropwise to the solution. The mixture was allowed to warm gradually to rt and stirred for 16 h under N$_2$. The solution was concentrated and the residue was used for the next step directly.

2.23 Preparation of Compound 5

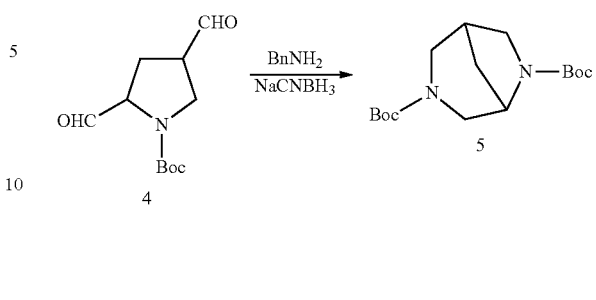

In an ice bath, to a solution of compound 4 (40 g, 41 mmol) in MeOH (210 mL) were added BnNH$_2$ (10.5 mL, 98 mmol) and NaBH$_3$CN. Then the mixture was stirred at rt under N$_2$ overnight. An aqueous solution of NaHCO$_3$ was added into the reaction mixture and the volatile was evaporated in vacuo. The residue was extracted with EA (400 mL×2). The combined organic phase was dried over Na$_2$SO$_4$, and concentrated in vacuo. The residue was purified by chromatography to give the desired product (8.0 g, 65%). $^1$H NMR (400 MHz, CDCl$_3$): δ ppm: 7.27-7.31 (m, 4H), 7.23-7.25 (m, 1H), 3.91-4.04 (m, 1H), 3.43-3.62 (m, 3H), 3.28-3.36 (m, 1H), 3.01-3.21 (m, 1H), 2.76-2.85 (m, 1H), 2.31-2.35 (m, 1H), 2.26 (t, J=12 Hz, 1H), 2.01 (t, J=10 Hz, 1H), 1.83-1.94 (m, 2H), 1.54 (s, 4H), 1.42 (s, 5H).

2.24 Preparation of B26

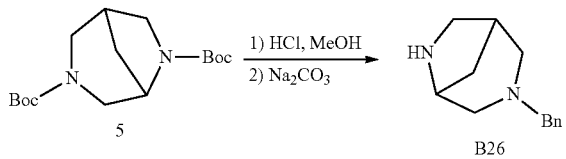 [SMILES: CC(C)(C)OC(=O)N1CC2CC(C1)N(C(=O)OC(C)(C)C)C2 ; "B26" ; c1ccc(CN2CC3CNC(C3)C2)cc1]

Compound 5 (1.0 g, 3.3 mmol) was treated with 4M HCl-MeOH (20 mL). Then the mixture was stirred at rt for 0.5 h, and evaporated in vacuo. The residue was used for the next step directly.

2.25 Preparation of B27

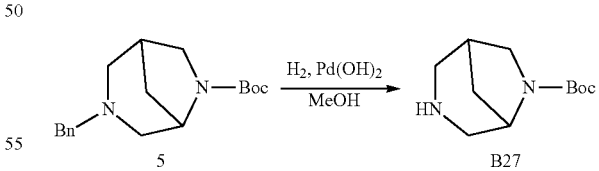

To a solution of compound 5 (450 mg, 1.49 mmol) in MeOH (20 mL) was added Pd(OH)$_2$/C (150 mg). The mixture was stirred under H$_2$ balloon at rt overnight. The mixture was filtered and the filtrate was concentrated to give desired product B27 as an oil (260 g, 82.2%). $^1$H NMR (400 MHz, CDCl$_3$): δ ppm: 3.88-4.02 (d, J=54.8 Hz, 1H), 3.33-3.47 (m, 2H), 2.80-3.01 (m, 3H), 2.63-2.67 (d, J=13.2 Hz, 1H), 2.22-2.25 (m, 1H), 1.96 (m, 1H), 1.79 (m, 1H), 1.48 (s, 9H).

Preparation of B34/35

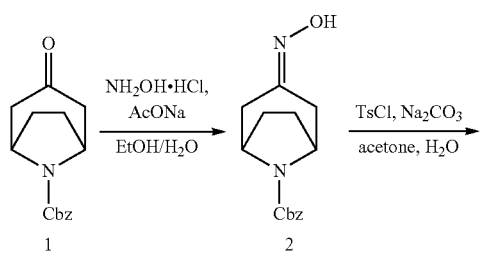

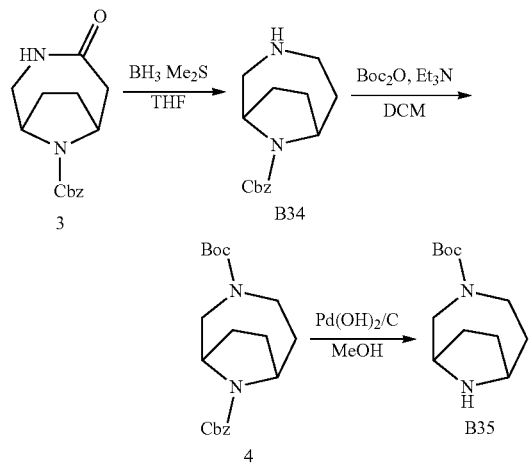

2.26 Preparation of Compound 2

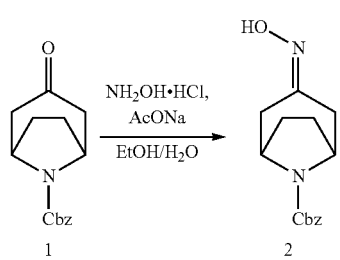 [SMILES: O=C1CC2CCC(C1)N2C(=O)OCc1ccccc1 ; O=C(OCc1ccccc1)N1C2CCC1CC(=NO)C2]

To a solution of compound 1 (8.6 g, 33.2 mmol) and AcONa (8.1 g, 99.6 mmol) in EtOH (170 mL) and H$_2$O (9 mL) was added NH$_2$OH HCl (11.4 g, 165 mmol). Then the mixture was stirred at rt for 1 h. The mixture was concentrated in vacuo and the residue was extracted with EA (200 mL×2). The organic layer was washed with NaHCO$_3$ and concentrated to give the crude product, which was used for the next step directly (8.9 g, 97%).

2.27 Preparation of Compound 3

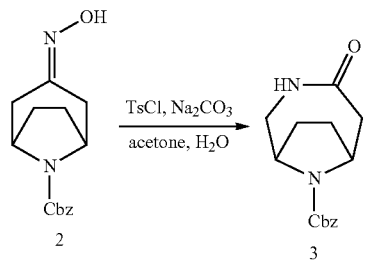 [SMILES: O=C(OCc1ccccc1)N1C2CCC1CC(=NO)C2 ; O=C1CC2CCC(CN1)N2C(=O)OCc1ccccc1]

To a solution of compound 2 (9.4 g, 34.3 mmol) in acetone (100 mL) was added a solution of Na$_2$CO$_3$ (10.9 g, 103 mmol) in H$_2$O (60 mL), followed by a solution of TosCl (9.8 g, 51.6 mmol) in acetone (50 mL). Then the mixture was stirred at 75° C. for 4 h. The mixture was concentrated in vacuo and the residue was extracted with DCM (200 mL×2). The organic layer was washed with brine and concentrated in vacuo to give the crude product, which was purified by chromatography to give the desired product (8.4 g, 89%).

2.28 Preparation of B34

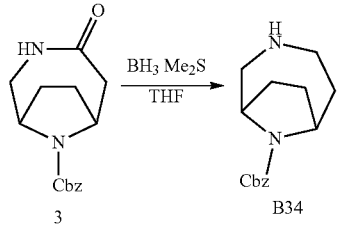

In an ice bath, to a solution of compound 3 (7.4 g, 27 mmol) in THF (100 mL) was added BH$_3$-Me$_2$S (12.1 ml, 121 mmol) dropwise. Then the mixture was stirred at rt overnight. The mixture was quenched with MeOH and concentrated in vacuo. The residue was dissolved in 2M HCl (160 mL) and heated to reflux for 3 h. The mixture was basified with Na$_2$CO$_3$ to a pH of around 9. The mixture was extracted with DCM and the organic layer was concentrated to give the crude product, which was purified by chromatography to give the desired product, B34 (4.0 g, 56.9%). LCMS: 261.0 [M+1].

2.29 Preparation of Compound 4

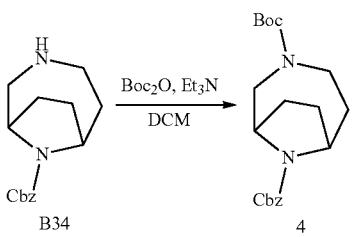

To a solution of B34 (2.0 g, 7.7 mmol) and Et$_3$N (1.16 g, 11.5 mmol) in DCM (20 mL) was added Boc$_2$O (2.0 g, 9.2 mmol). Then the mixture was stirred at rt for 2 h. It was purified by silica gel chromatography to give the pure product as oil (2.3 g, 83%).

2.30 Preparation of B35

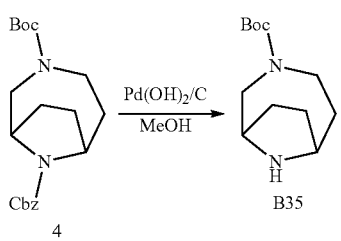

To a solution of compound 4 (1.88 g, 5.2 mmol) in MeOH (50 mL) was added Pd(OH)$_2$/C (210 mg). The mixture was stirred under H₂ balloon at rt for 3 h. The mixture was filtered and the filtrate was concentrated to give desired compound 3 as an oil (260 g, 82.2%). LCMS: 227 [M+1].

Part II General Procedure for Targets

General Procedure A:

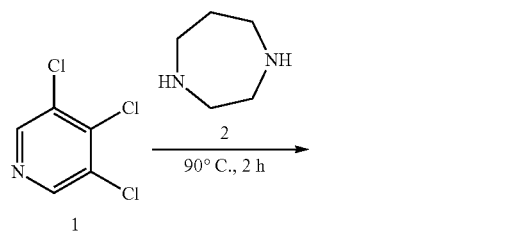

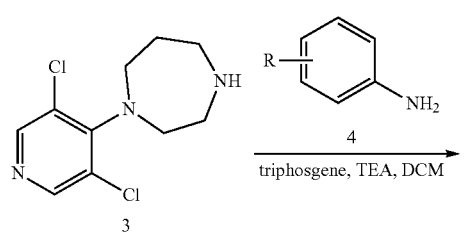

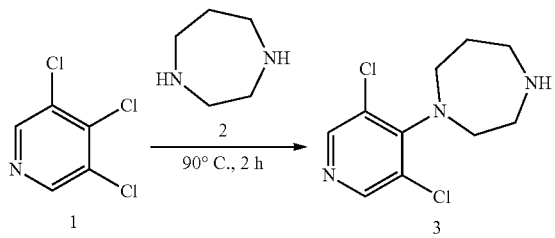

3.1 Preparation of Compound 3

Compound 1 (5.00 g, 27.50 mmol) and compound 2 (13.75 g, 137.50 mmol) were combined without solvent and the mixture was stirring at 90-100° C. for 2 h. The mixture was diluted with DCM (250 mL) and washed with NH₄Cl (100 mL×2). The combined organic layer was concentrated to give the crude product, which was purified by silica chromatography gel to give the desired product (5.80 g, 72%). ¹H NMR (400 MHz, CDCl₃): δ ppm: 8.43 (s, 2H), 3.40 (m, 4H), 3.16 (t, J=5.6 Hz, 2H), 3.09 (m, 2H), 1.99 (m, 2H).

3.2 Preparation of A01B01C01D

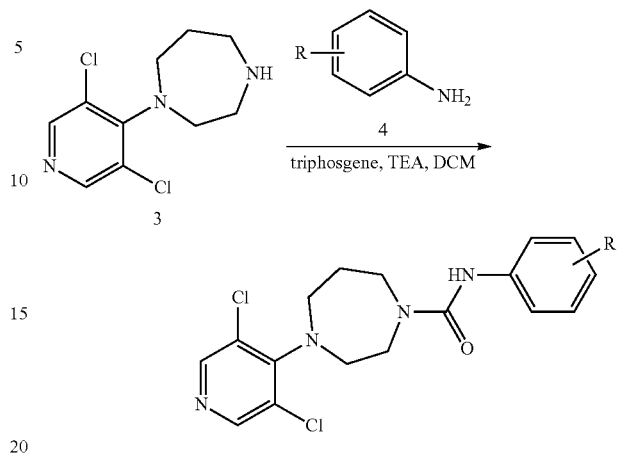

To a solution of compound 4 (0.40 mmol) and Et₃N (202 mg, 2.00 mmol) in DCM (10 mL) was added triphosgene (72 mg, 0.24 mmol). After the mixture stirring for 5 minutes, compound 3 (98 mg, 0.40 mmol) was added and stirred at rt for 30 min. The solvent was removed and the residue was purified by prep-HPLC (FA) to give the desired product.

General Procedure B:

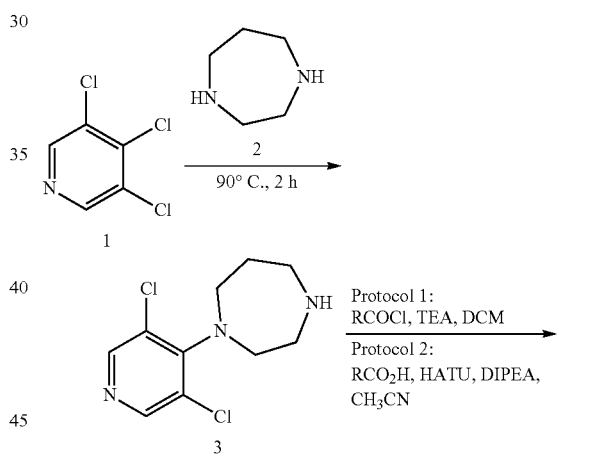

3.3 Preparation of Compound 3

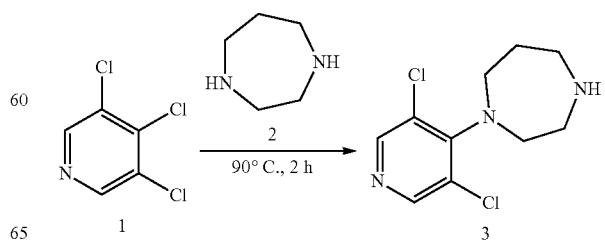

Compound 3 was prepared as described in Section 3.1 of General procedure A.

3.4 Preparation of A01B01C01R

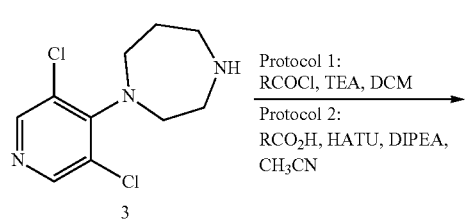

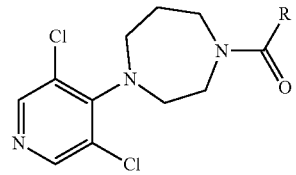

Protocol 1:
To a solution of compound 2 (98 mg, 0.40 mmol) and Et₃N (81 mg, 0.80 mmol) in DCM (2 mL) was added acyl chloride (0.40 mmol) and stirred at rt for 30 min. The solvent was removed and the residue was dissolved in CH₃CN, which was purified by prep-HPLC (FA) to give the desired product.

Protocol 2:
To a solution of compound 3 (55 mg, 0.40 mmol) and DIPEA (77 mg, 0.60 mmol) in CH₃CN (2 mL) was added HATU (198 mg, 0.52 mmol) under N₂. After the mixture stirring at rt for 30 min, carboxylic acid (0.40 mmol) was added and stirred for another 30 min. The mixture was diluted with EA (50 mL) and washed with water (20 mL×2). The organic layer was concentrated to give the crude product, which was purified by prep-HPLC (FA) to give the desired product.

General procedure C:

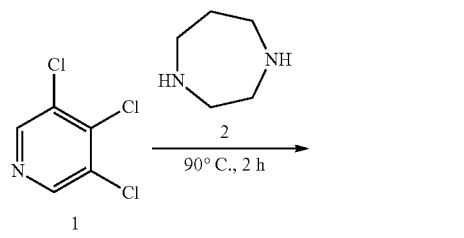

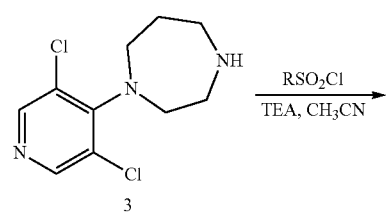

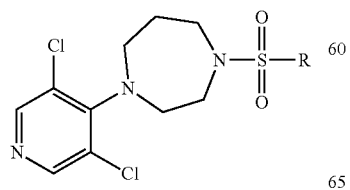

3.5 Preparation of Compound 3

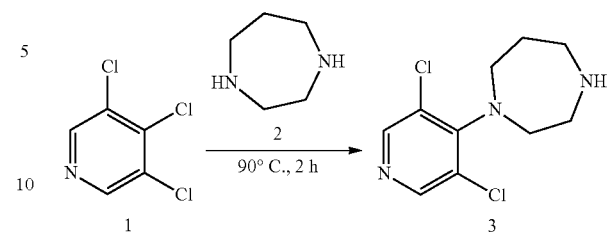

Compound 3 was prepared as described in 3.1 of General procedure A.

3.6 Preparation of A01B01C02R

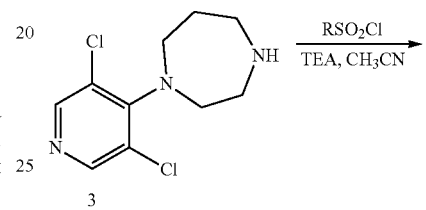

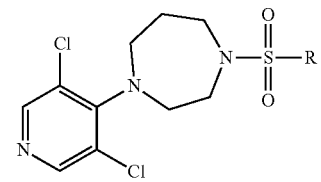

To a solution of compound 3 (98 mg, 0.40 mmol) and Et₃N (81 mg, 0.80 mmol) in CH₃CN (4 mL) was added RSO₂Cl (0.40 mmol) and stirred at rt for 30 min. It was purified by prep-HPLC (FA) to give the desired product.

General Procedure D:

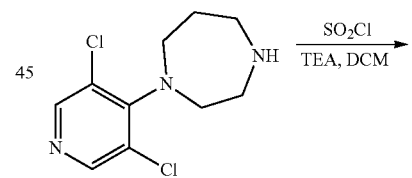

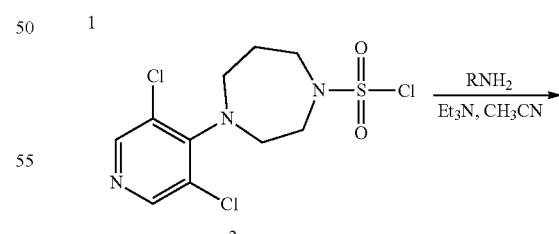

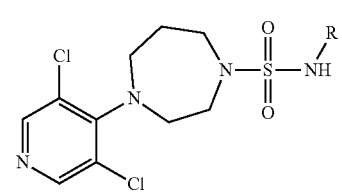

3.7 Preparation of Compound 2

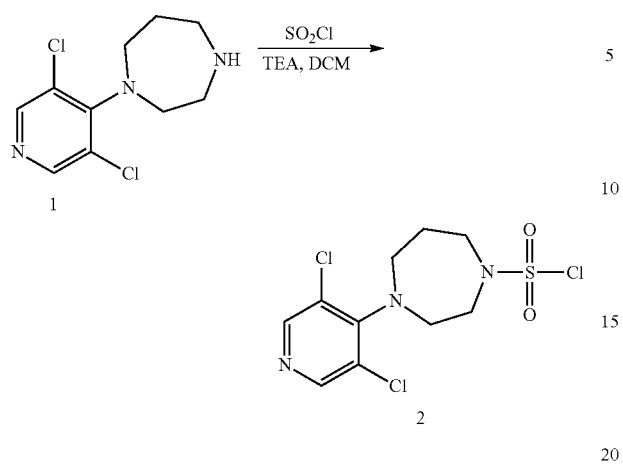

At −40° C., to a solution of compound 1 (2.78 g, 11.30 mmol) and Et₃N (2.29 g, 22.70 mmol) in DCM (50 mL) was added SO₂Cl₂ (3.06 g, 22.7 mmol) under N₂. Then the mixture was stirred at rt for 1 h. The mixture was quenched with water and extracted with DCM (200 mL). The organic layer was concentrated to give the crude product (3.39 g, 96.7%).

3.8 Preparation of Compounds 031-038, and 052 (A01B01C02R)

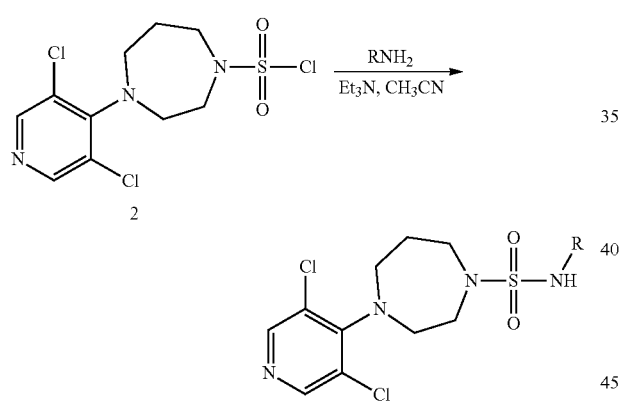

To a solution of RNH₂ (0.35 mmol) and Et₃N (58 mg, 0.58 mmol) in CH₃CN (4 mL) was added compound 2 (100 mg, 0.29 mmol) and the reaction was stirred at rt. The reaction was heated to 80° C. for the unreactive amines and anilines. LCMS was used to monitor reaction completion. The mixture was purified by prep-HPLC (FA) to give the desired product.

General Procedure E:

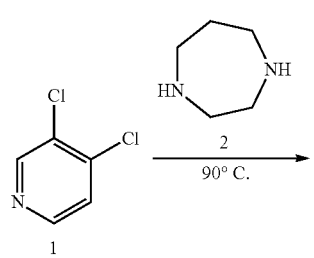

-continued

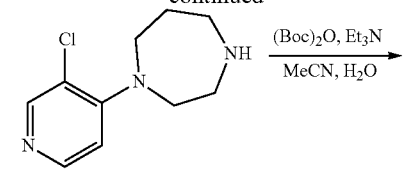

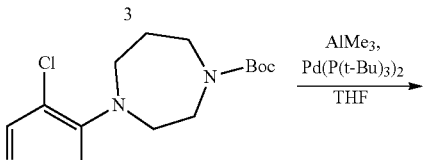

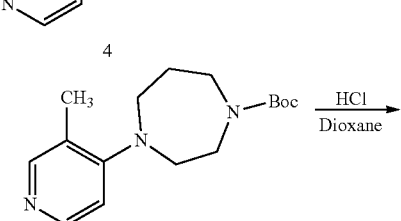

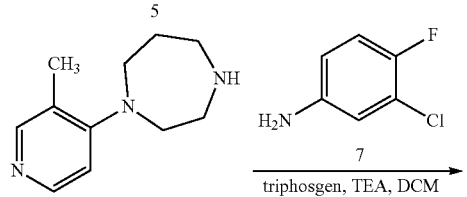

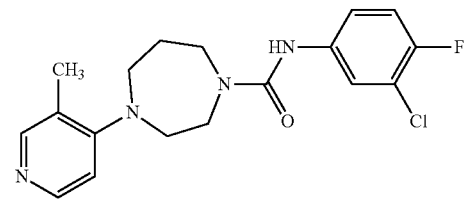

Compound 043

3.9 Preparation of Compound 3

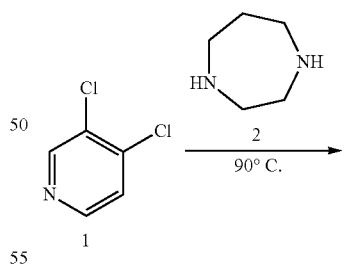

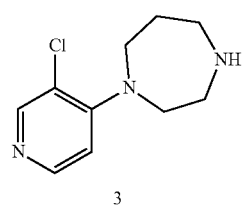

A mixture of compound 1 (1.5 g, 10 mmol) and compound 2 (5.0 g, 50 mmol) was heated to 90-100° C. for 2 h. The mixture was diluted with DCM (250 mL) and washed with NH4Cl (50 mL×2). The combined organic layer was concentrated to give the crude product, which was used in next step directly.

3.10 Preparation of Compound 4

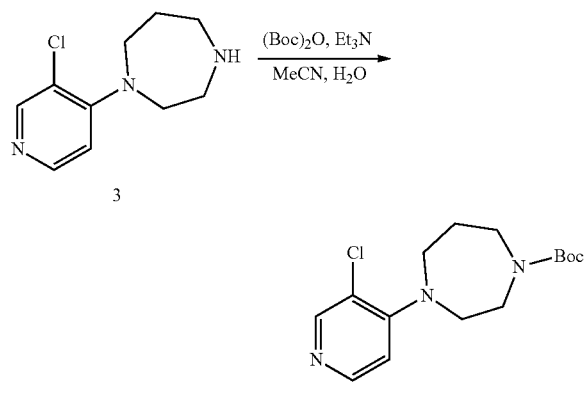

To a solution of compound 3 (468 mg, 2.21 mmol) in MeCN/H2O (10 ml/2 ml) added (Boc)2O (703 mg, 3.32 mmol) followed by Et3N (1.02 g, 10.1 mmol). The reaction mixture was stirred at 26° C. for 16 h, The mixture was concentrated in vacuum and extracted with EA, dried over Na2SO4. The crude product was purified by column chromatography on silica gel (DCM:MeOH=20:1) to give product (467 mg, 74.4%) as brown oil. LCMS: 312/314 [M+1].

3.11 Preparation of Compound 5

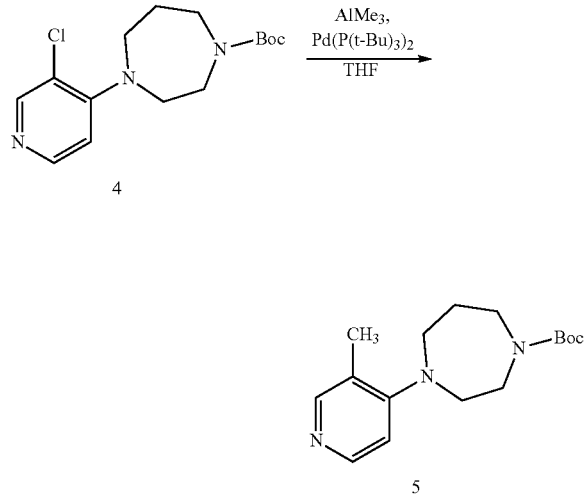

To a solution of compound 4 (467 mg, 1.5 mmol) and Pd(P(t-Bu)3)2 (115 mg, 0.225 mmol) in THF (5.0 mL) added AlMe3 (2.0 M, 1.13 mL) in one portion at 26° C. under N2. The mixture was heated to 70° C. for 2 h. The mixture was quenched with NH4Cl, and extracted with EA, The combined organic layer was washed with aq. Na2CO3 and brine, dried over Na2SO4, and concentrated in vacuum. The resulting crude product was purified by column chromatography on silica gel (DCM:MeOH=40:1) to give product (306 mg, 69.8%) as brown oil. LCMS: 292[M+1].

3.12 Preparation of Compound 6

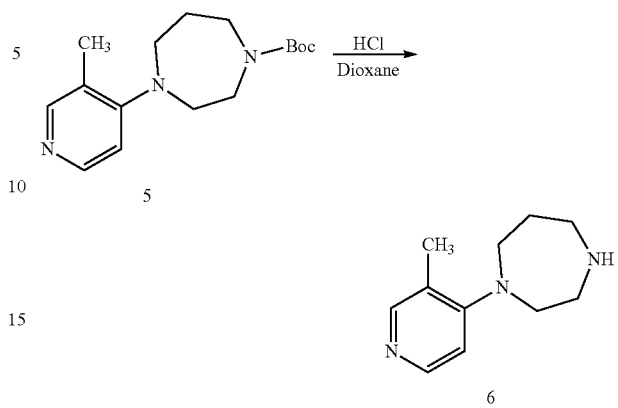

To a solution of Compound 5 (306 mg, 1.05 mmol) in DCM (10.0 mL) added HCl/dioxane (10 mL), and stirred at 25° C. for 3 h. The mixture was concentrated in vacuum to give product (199 mg, 99%) as brown oil. LCMS: 192[M+1].

3.13 Preparation of Compound 043

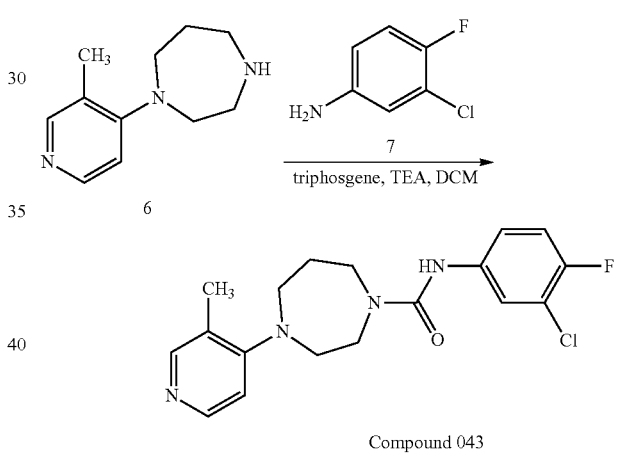

Compound 043

To a solution of compound 7 (73 mg, 0.50 mmol) and Et3N (255 mg, 2.5 mmol) in DCM (10 mL) was added triphosgene (90 mg, 0.3 mmol). After the mixture stirring for 5 min, compound 6 (90 mg, 0.50 mmol) was added and stirred at rt for 30 min. The solvent was removed and the residue was purified prep-HPLC (FA) to give the desired product (54 mg, 30%). LCMS: 363/365 [M+1].

General Procedure F:

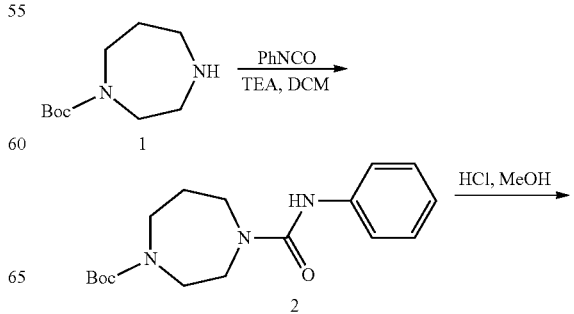

-continued

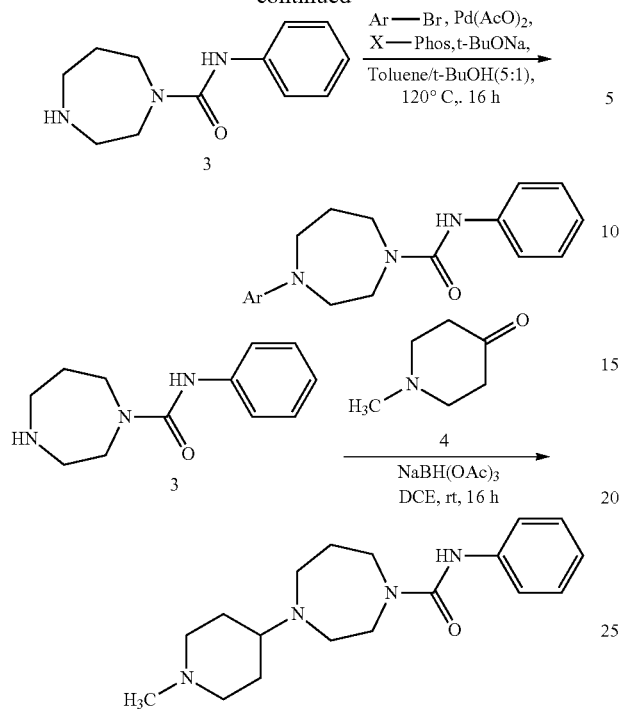

3.15 Preparation of Compound 3

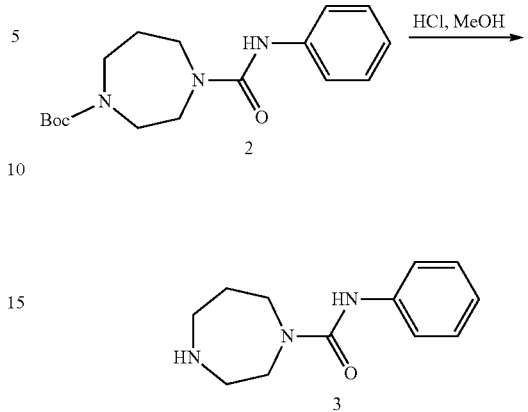

Compound 2 (638 mg, 2 mmol) was treated with 4 N HCl in methanol (10 mL), and stirred at rt for 30 min. The mixture was concentrated in vacuo to give a HCl salt (500 mg, 99%).

3.16 Preparation of Compounds 018-020

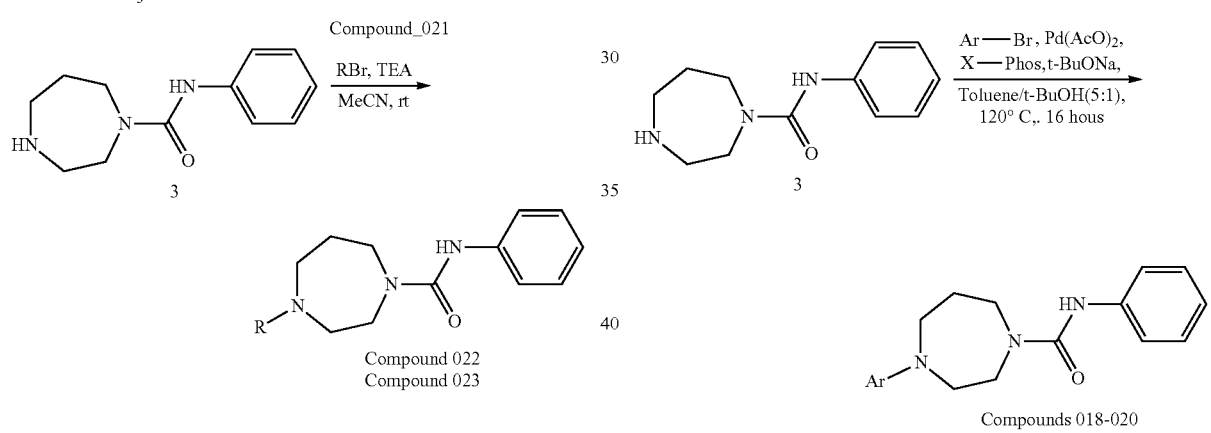

To a solution of compound 3 (0.6 mmol) and ArBr (0.66 mmol) in Toluene/t-BuOH (6 mL, 5:1) was added Pd(OAc)$_2$ (0.03 mmol), X-Phos (0.06 mmol) and t-BuONa (0.72 mmol), and the mixture was stirred at 120° C. for 16 h under N$_2$ atmosphere. The mixture was concentrated in vacuo. The residue was diluted with DCM (20 mL) and washed with water. The organic phase was concentrated in vacuo to give the crude product, which was purified by prep-HPLC (FA) to give desired product.

3.17 Preparation of Compound 021

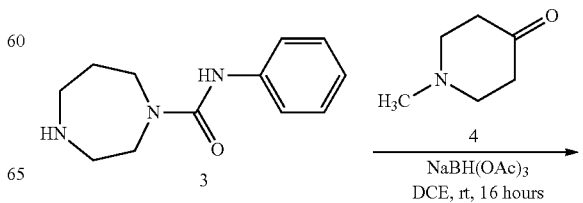

3.14 Preparation of Compound 2

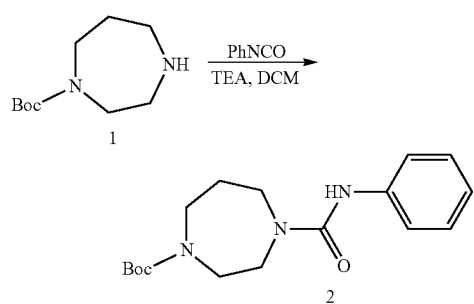

To a solution of compound 1 (2 g, 10 mmol) and TEA (2 g, 20 mmol) in DCM (40 mL) was added PhNCO (1.19 g, 10 mmol) at 0° C., and the mixture was stirred at rt for 2 h. The mixture was diluted with DCM (20 mL) and washed with water. The organic phase was concentrated in vacuo to give compound 2 as colorless oil. (2.5 g, yield: 78%). LCMS: 320 [M+1].

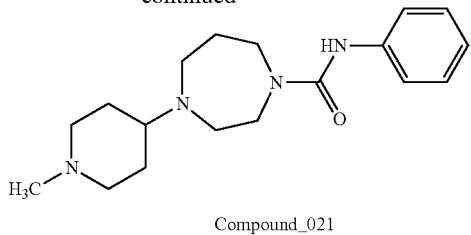

Compound_021

To a solution of compound 3 (0.6 mmol) and compound 4 (0.72 mmol) in DCE (5 mL) was added NaBH(OAc)$_3$ (1.2 mmol), and the mixture was stirred at rt for 16 h under N$_2$ atmosphere. Saturated NH$_4$Cl aqueous was added to quench the reaction. The mixture was extracted with EA (50 mL×3). The organic phase was concentrated in vacuo to give the crude product, which was purified by prep-HPLC (FA) to give desired product compound 021 as a white solid. (22 mg, yield: 11%). LCMS: 317 [M+1].

3.18 Preparation of Compounds 022 and 023

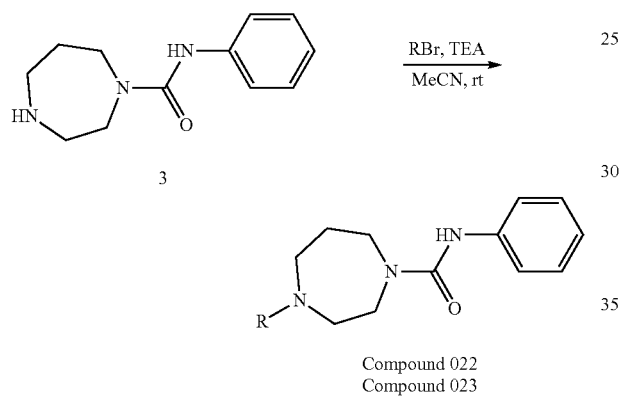

Compound 022
Compound 023

To a solution of compound 3 (0.6 mmol) and TEA (1.2 mmol) in MeCN (10 mL), was added RBr (0.66 mmol), and the mixture was stirred at rt for 16 h. The mixture was diluted with DCM (30 mL) and washed with water. The organic phase was concentrated in vacuo to give the crude product, which was purified by prep-HPLC (FA) to give desired product.

General Procedure G:

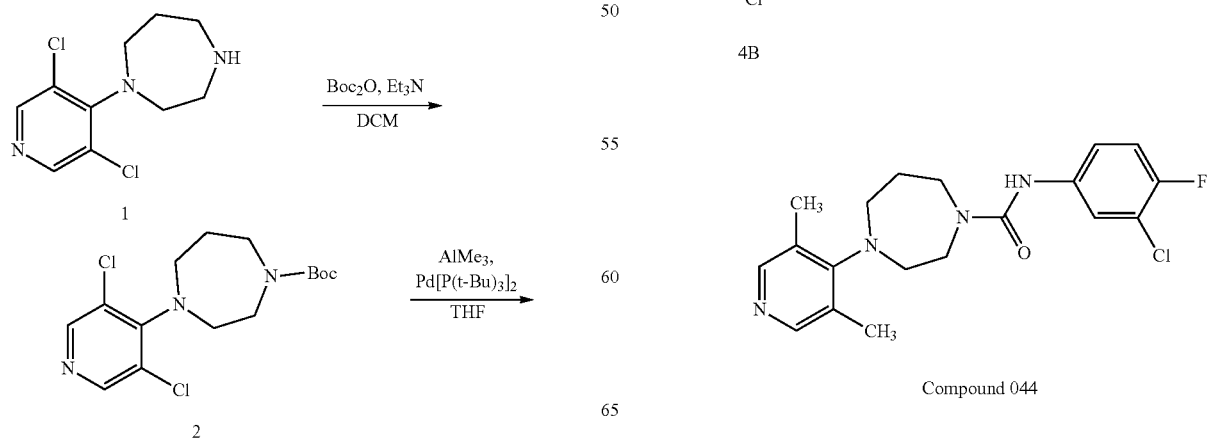

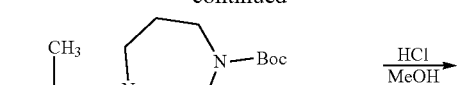

3A

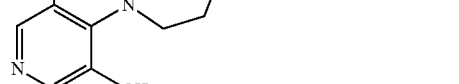

3B

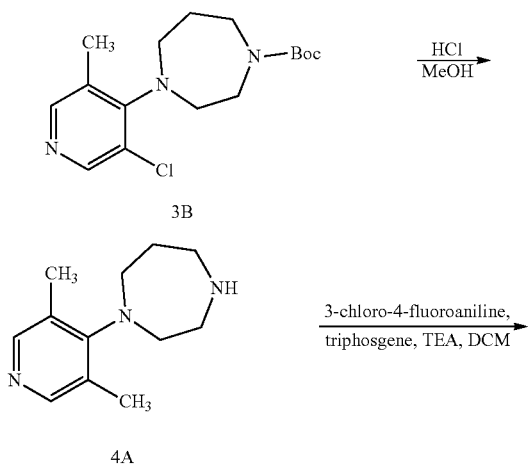

4A

Compound 047

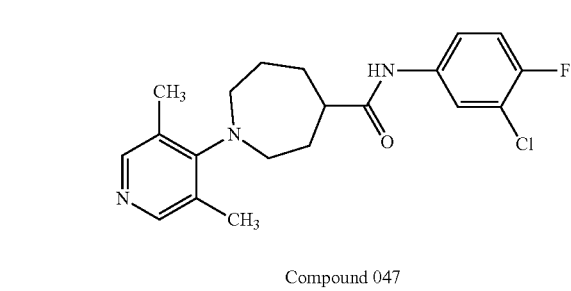

4B

Compound 044

3.19 Preparation of Compound 2

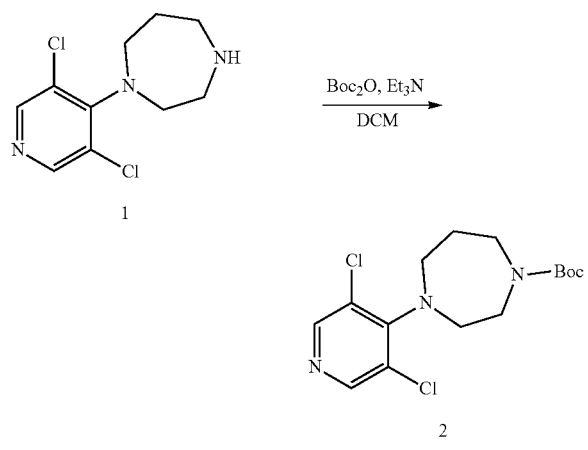

To a solution of compound 1 (1.0 g, 4.0 mmol) and Et₃N (0.49 g, 4.8 mmol) in DCM (10 mL) was added Boc₂O (1.14 g, 5.2 mmol). Then the mixture was stirred at rt for 30 min. It was purified by silica gel chromatography to give the pure product (1.38 g, 98.5%).

3.20 Preparation of Compound 3A & 3B

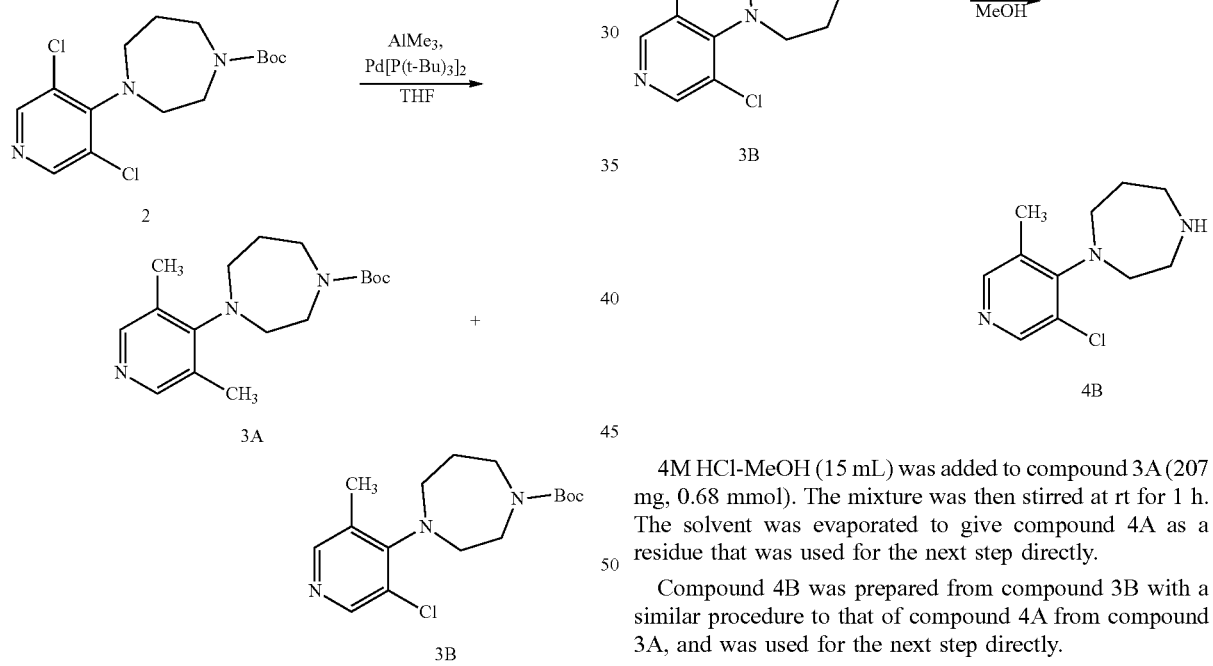

To a solution of compound 1 (345 mg, 1.0 mmol) in THF (5 mL) were added AlMe₃ (0.77 mg, 1.54 mmol) and Pd[P(t-Bu)₃]₂ (79 mg, 0.15 mmol) under N₂. Then the mixture was heated to reflux for 1.5 h. The mixture was poured into Na₂CO₃ aqueous and extracted with EA (50 mL×2). The organic layer was concentrated to give the crude product, which was purified by silica gel chromatography to give 3A (207 mg, 68%). LCMS: 306 [+1].

To a solution of compound 2 (345 mg, 1.0 mmol) in THF (5 mL) were added AlMe₃ (0.4 mL, 0.8 mmol) and Pd[P(t-Bu)₃]₂ (79 mg, 0.15 mmol) under N₂. Then the mixture was heated to reflux for 2 h. The mixture was poured into Na₂CO₃ aqueous and extracted with EA (50 mL×2). The organic layer was concentrated to give the crude product, which was purified by silica gel chromatography to give 3B (33 mg, 10%). LCMS: 326 [M+1].

3.21 Preparation of Compound 4A & 4B

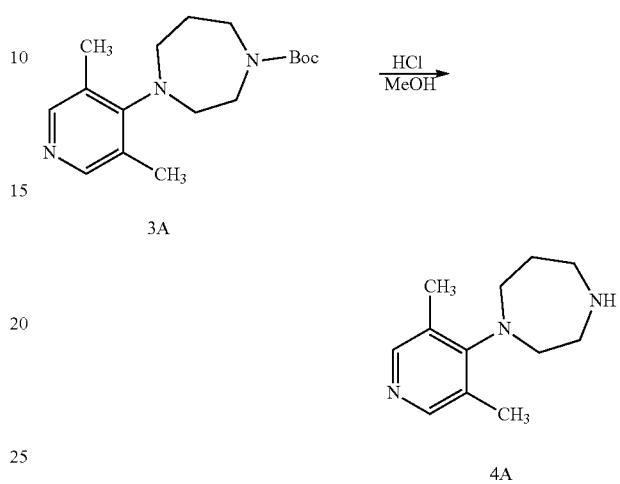

4M HCl-MeOH (15 mL) was added to compound 3A (207 mg, 0.68 mmol). The mixture was then stirred at rt for 1 h. The solvent was evaporated to give compound 4A as a residue that was used for the next step directly.

Compound 4B was prepared from compound 3B with a similar procedure to that of compound 4A from compound 3A, and was used for the next step directly.

3.22 Preparation of Compounds 047 & 044

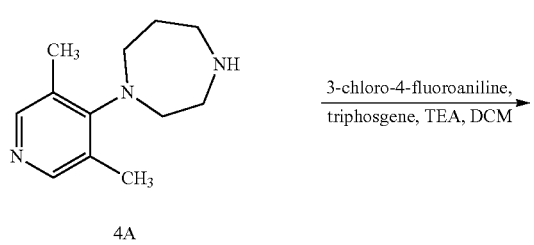

-continued

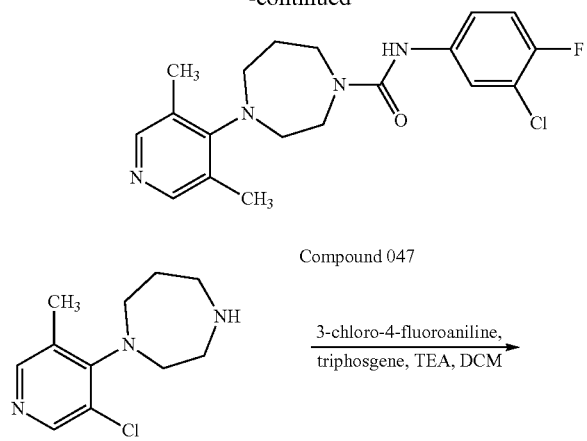

Compound 047

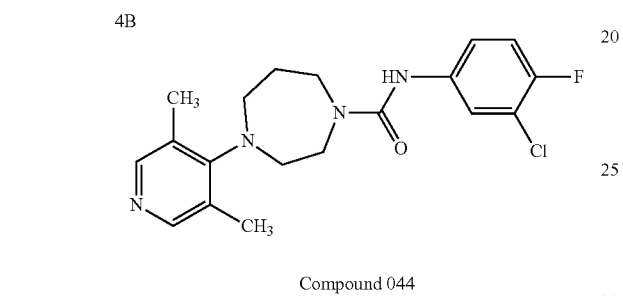

Compound 044

To a solution of 3-chloro-4-fluoroaniline (55 mg, 0.38 mmol) and Et$_3$N (171 mg, 1.70 mmol) in DCM (10 mL) was added triphosgene (61 mg, 0.20 mmol). After the mixture stirring for 2 min, compound 4A (82 mg, 0.34 mmol) was added and stirred at rt for 30 min. The solvent was removed and the residue was dissolved in CH$_3$CN, which was purified by prep-HPLC (FA) to give the desired product, compound 047 (44 mg, 34%). $^1$H NMR (400 MHz, MeOD): δ ppm: 8.19 (s, 2H), 7.56 (dd, J=2.8 Hz, 6.4 Hz, 1H), 7.22 (m, 1H), 7.04 (t, J=8.8 Hz, 1H), 6.62 (s, 1H), 3.72 (m, 4H), 3.22 (m, 4H), 2.24 (s, 6H), 1.98 (m, 2H).

Compound 044 was prepared from compound 4B with a similar procedure to that of preparing compound 047 from compound 4A. (Yield: 7 mg, 18%). LCMS: 397 [M+1].

General Procedure H:

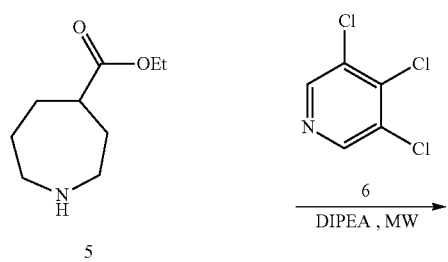

-continued

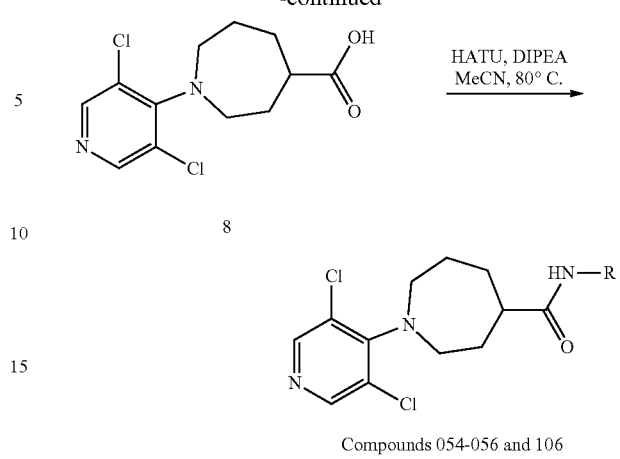

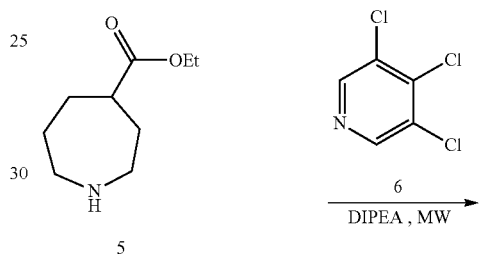

Compounds 054-056 and 106

3.23 Preparation of Compound 7

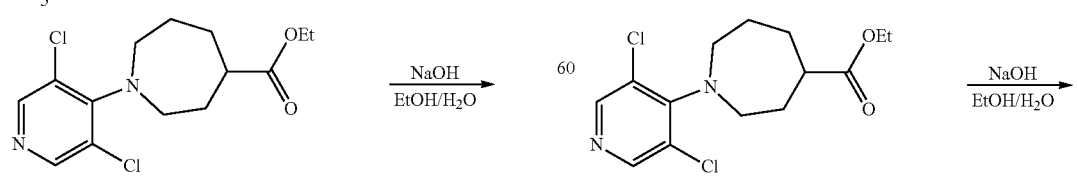

A mixture of compound 5 (650 mg, 3.8 mmol), compound 6 (650 mg, 3.6 mol) and DIPEA (981 mg, 7.6 mol) in NMP (10 mL) was radiated at 180° C. for 0.5 h by microwave. The mixture was diluted with EA (100 mL) and washed with water. The organic layer was dried and concentrated to give the crude product, which was purified by flash column chromatography to give the desired product (370 mg, 31%). LCMS: 317/319 [M+1].

3.24 Preparation of Compound 8

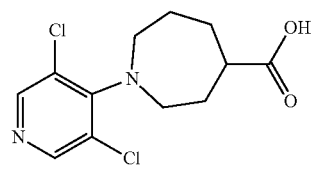

8

A mixture of compound 7 (370 mg, 1.2 mmol) and NaOH (71 mg, 1.8 mmol) in EtOH/H$_2$O (5/1, mL) was stirred at 85° C. for 1 h. The reaction mixture was acidified with HCl (2 N) to pH=5 and extracted with EA (100 mL). The organic layer was dried and concentrated to give the crude product, which was used for the next step directly (320 mg, 95%). LCMS: 289/291 [M+1].

3.25 Preparation of Compounds 054-056, and 106

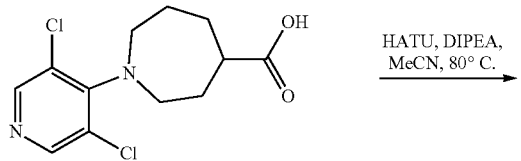

8

HATU, DIPEA, MeCN, 80° C.

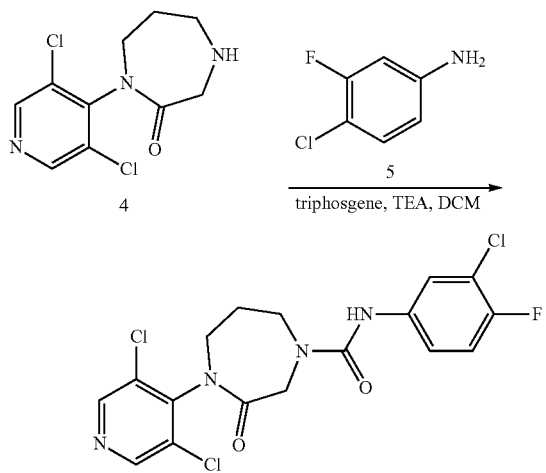

3

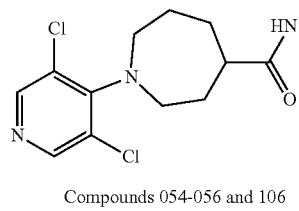 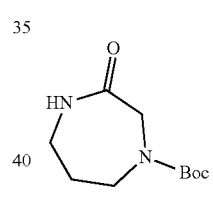

4     5 triphosgene, TEA, DCM

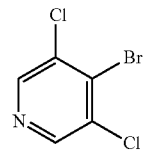

Compound 059

3.26 Preparation of Compound 3

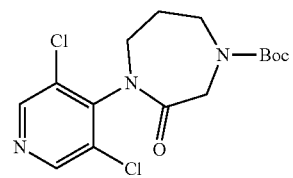

Compounds 054-056 and 106

To a solution of Compound 8 (100 mg, 0.35 mmol), HATU (158 mg, 0.42 mmol) and DIPEA (67 mg, 0.52 mmol) in MeCN (4 mL) was added 3-chloro-4-fluoroaniline (55 mg, 0.38 mmol), and the mixture was heated to 70° C. for 16 h. The mixture was filtered, and the filtrate was purified by Prep-HPLC to give the desired product, compound 055 (99 mg, 69%). LCMS: 416.0/418.0 [M+1].

Compound 054, 056, and 106 were prepared following the same procedure for that used to prepare compound 55.

General Procedure I:

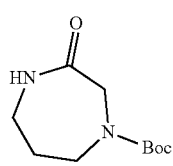 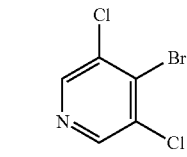

1     2

Pd(OAc)$_2$, Xantphos t-BuONa, toluene

A mixture of compound 1 (600 mg, 2.7 mmol), compound 2 (600 mg, 2.8 mmol), Pd(OAc)$_2$ (90 mg, 0.4 mmol), Xantphos (460 mg, 0.8 mmol) and t-BuONa (510 mg, 5.3 mmol) in toluene (50 mL) was heated to 115° C. for 16 h under N$_2$. The mixture was filtered and the filtrate was concentrated in vacuo. The residue diluted with EA (150 mL) and washed with brine (100 mL). The organic layer was dried and concentrated to give the crude product, which was purified by flash column chromatography to give the desired product, compound 3 (190 mg, 20%). $^1$H NMR (400 MHz, CDCl$_3$): δ ppm: 8.59 (s, 2H), 4.28-4.26 (m, 2H), 3.73-3.67 (m, 4H), 2.14-2.12 (m, 2H), 1.51 (s, 9H).

3.27 Preparation of Compound 4

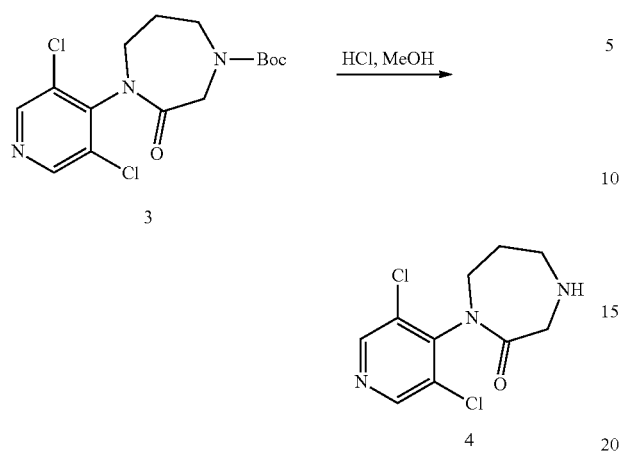

To a solution of compound 3 (190 mg, 0.53 mmol) in MeOH (5 mL) was added HCl/MeOH (4 N, 5 mL), and stirred at 25° C. for 0.5 h. The formed mixture was concentrated to give the crude product, which was used in the next step directly (156 mg, 100%).

3.28 Preparation of Compound Compound 059

To a solution of compound 4 (50 mg, 0.17 mmol) in DCM (15 mL) was added TEA (0.5 mL, 3.5 mmol) and triphosgene (31 mg, 0.10 mmol) at 0° C. under $N_2$. After stirring for 5 min, compound 5 (25 mg, 0.17 mmol) was added, and the reaction mixture was stirred at 25° C. for 1 h. The resulting mixture was diluted with DCM (50 mL), and washed with brine. The organic layer was dried and concentrated to give the crude product, which was purified by Prep-HPLC to give the desired product (42.11 mg, 58%). LCMS: 431/433 [M+1].

Compounds 057 and 058 were prepared following the same procedure as used to prepare compound 059.

General Procedure J:

3.29 Preparation of Compound 3

To a solution of compound 1 (200 mg, 0.78 mmol) and $K_2CO_3$ (214 mg, 1.56 mmol) in MeCN (10 mL) was added compound 2 (234 mg, 2.34 mmol). The reaction mixture was stirred at 90° C. overnight. The reaction mixture was filtered and concentrated. The residue was dissolved in water (20 mL) and extracted with EA (30 mL). The organic layer was dried and concentrated to give the crude product, and purified by column to give the product (130 mg, yield: 73%). LCMS: 230/232 [M+1].

3.30 Preparation of Compound 045

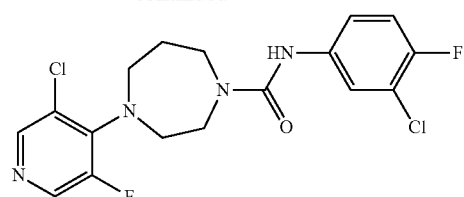

Compound 045

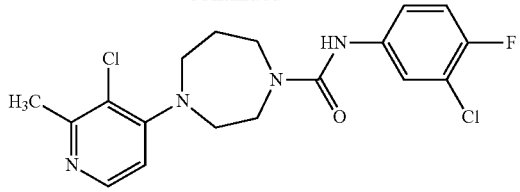

Compound 046

To a solution of compound 3 (46 mg, 0.2 mmol) in DCM (10 mL) was added TEA (202 mg, 2 mmol) and triphosgene (36 mg, 0.12 mmol) at 0° C. under N$_2$. After stirring for 5 min, compound 4 (28 mg, 0.2 mmol) was added, and the reaction mixture was stirred at 25° C. for 1 h. The resulting mixture was diluted with DCM (50 mL), and washed with brine. The organic layer was dried and concentrated to give the crude product, which was purified by Prep-HPLC to give the desired product (40 mg, 50%). LCMS: 401/403 [M+1].

General Procedure K:

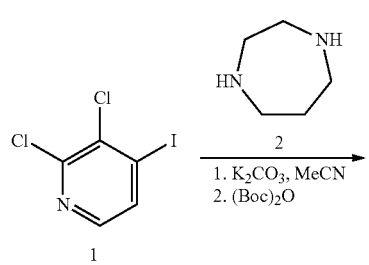

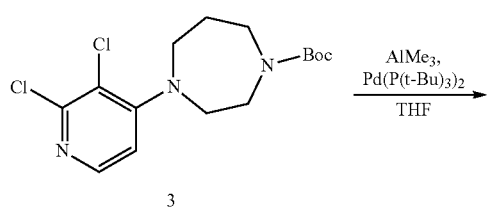

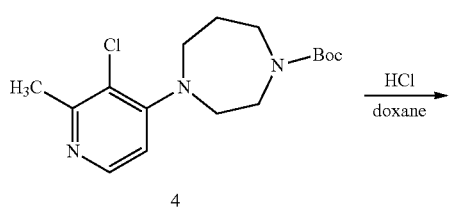

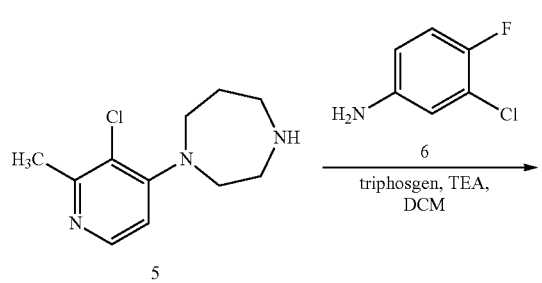

3.31 Preparation of Compound 3

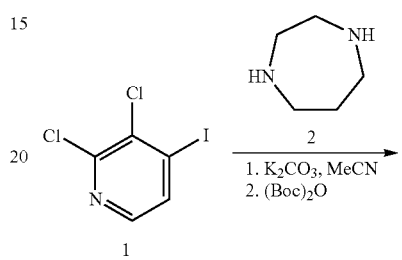

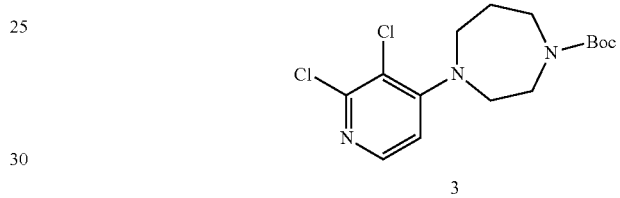

A mixture of compound 1 (1.6 g, 16.0 mmol), compound 2 (2.85 g, 10.4 mmol) and K$_2$CO$_3$ (2.87 g, 20.8 mmol) in MeCN (40 mL) was heated to 70° C. for 20 h, (Boc)$_2$O (6.6 g, 31.2 mmol) added into the mixture and stirred at rt for another 5 h. The mixture was extracted with EA and water. The organic phase was dried over Na$_2$SO$_4$, and concentrated in vacuo. The residue was purified by column chromatography on silica gel (PE:EA=8:1) to give product (400 mg, 11.8%) as yellow oil. LCMS: 346/348 [M+1].

3.32 Preparation of Compound 4

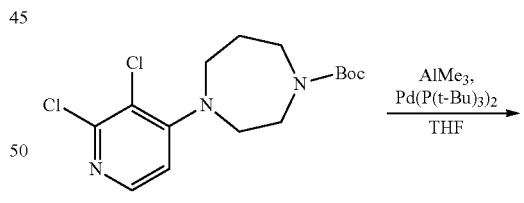

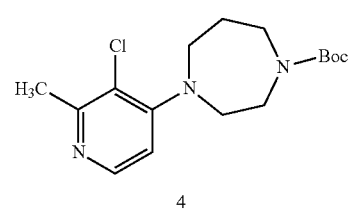

To a solution of compound 3 (200 mg, 0.56 mmol) and Pd(P(t-Bu)$_3$)$_2$ (42.9 mg, 0.084 mmol) in THF (5.0 ml) was added AlMe$_3$ (2.0 M, 0.56 ml) in one portion at 30° C. under N$_2$. The mixture was heated to 70° C. for 2 h. Another batch of AlMe$_3$ (2.0 M, 0.56 ml) and Pd(P(t-Bu)$_3$)$_2$ (42.9 mg, 0.084 mmol) was added. The mixture was continued to heat to 70° C. for another 2 h. The mixture was quenched with saturated NH$_4$Cl, and extracted with EA. The combined organic layer was washed with aq. Na$_2$CO$_3$ and brine, dried over Na$_2$SO$_4$, and concentrated in vacuum. The crude product was purified by column chromatography on silica gel (PE:EA=3:1) to give the product (80 mg, 43.8%) as yellow oil. LCMS: 326/328 [M+1].

3.33 Preparation of Compound 5

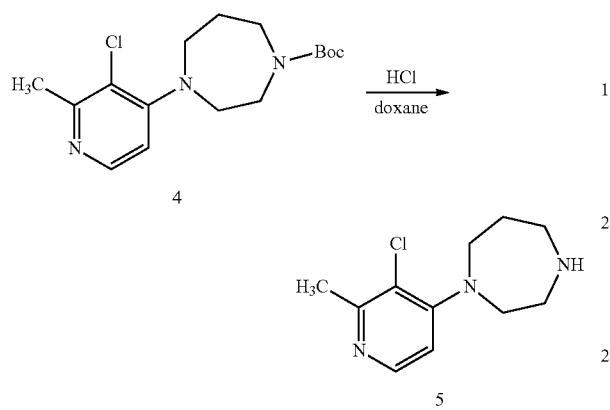

Compound 4 (80 mg, 0.245 mmol) was treated with HCl/Dioxane (4N, 2.0 mL). The mixture was stirred at 25° C. for 3 h. Then, the mixture was concentrated in vacuum to give crude product as, used directly in next step. LCMS: 226/228 [M+1].

3.34 Preparation of Compound 046

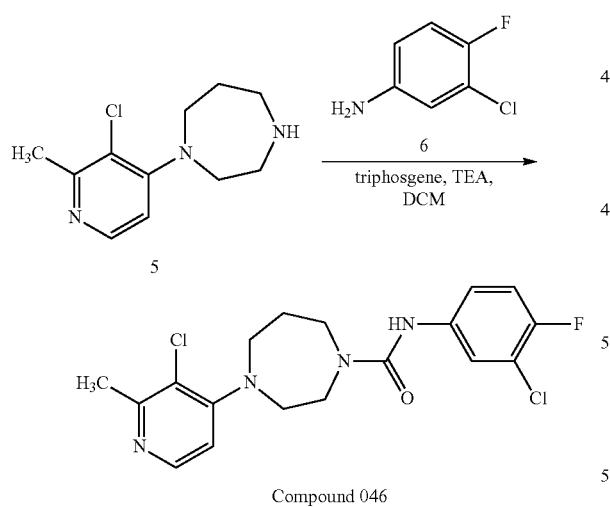

To a solution of compound 5 (45 mg, 0.2 mmol) in DCM (10 mL) was added TEA (202 mg, 2 mmol) and triphosgene (36 mg, 0.12 mmol) at 0° C. under N$_2$. After stirring for 5 min, compound 6 (28 mg, 0.2 mmol) was added, and the reaction mixture was stirred at 25° C. for 1 h. The resulting mixture was diluted with DCM (50 mL), and washed with brine. The organic layer was dried and concentrated to give the crude product, which was purified by Prep-HPLC to give the desired product (40 mg, 50%). LCMS: 397/399 [M+1].

General Procedure L:

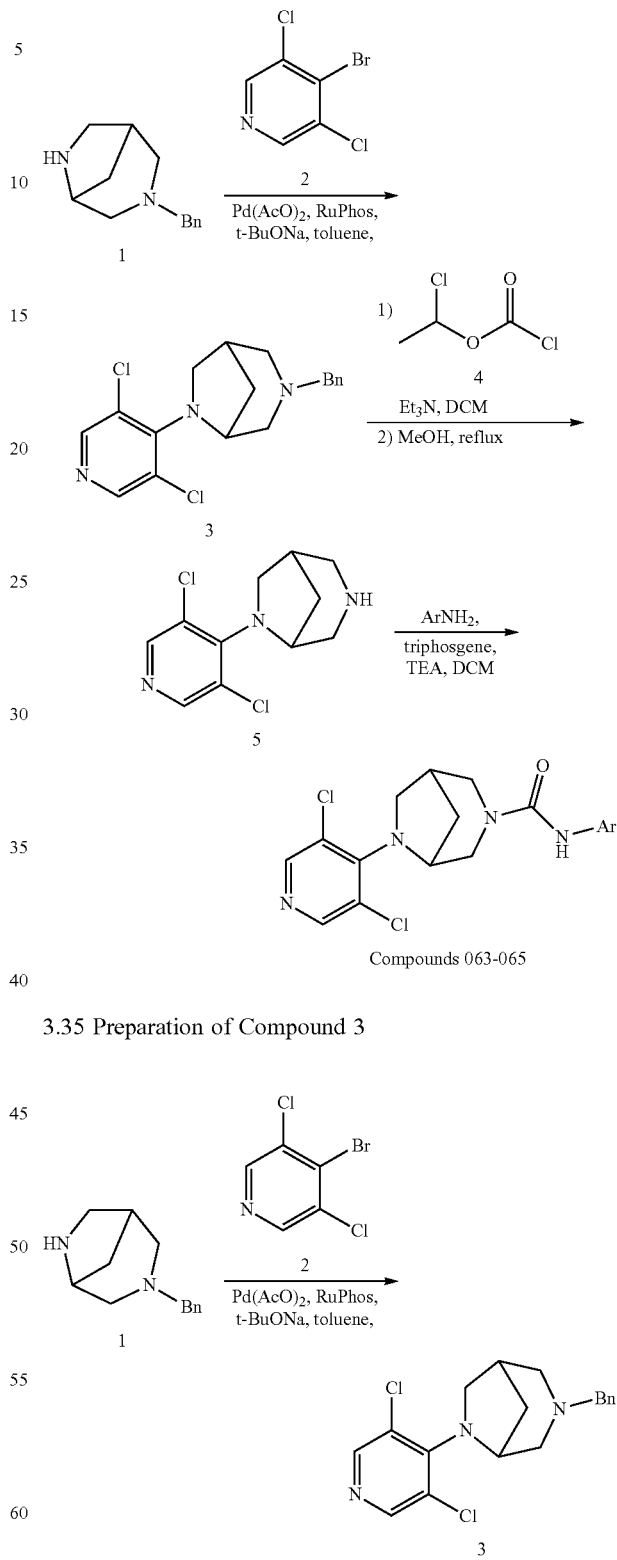

3.35 Preparation of Compound 3

To a solution of compound 1 (707 mg, 3.5 mmol), compound 2 (795 mg, 3.5 mmol), and NaO(t-Bu) (672 mg, 7.0 mmol) in toluene (20 mL) were added Pd(OAc)$_2$ (78 mg, 0.35 mmol) and Ruphos (244 mg, 0.52 mmol) under N$_2$.

Then the mixture was heated to reflux overnight. The solvent was removed and the residue was extracted with EA (80 mL×2). The organic layer was washed with water and concentrated to give the crude product, which was purified by silica gel chromatography to give the desired product, compound 3 (480 mg, 39%). LCMS: 348/350 [M+1].

3.36 Preparation of Compound 5

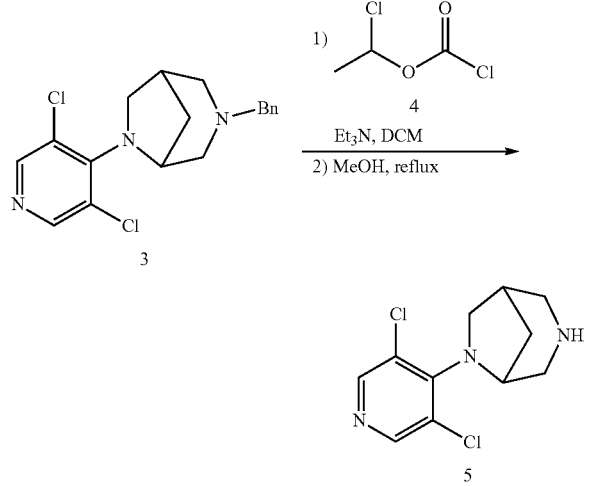

To a solution of compound 3 (200 mg, 0.57 mmol) in DCM (5 mL) were added compound 4 (408 mg, 2.86 mmol) and Et₃N (172 mg, 1.71 mmol). Then the mixture was heated to reflux overnight. The solvent was removed and the residue was dissolved in MeOH. The resulting mixture was heated to reflux for another 2 h. The mixture was concentrated in vacuo and purified by silica gel chromatography to give the desired product (180 mg, 81%). LCMS: 258/260 [M+1].

3.37 Preparation of Compounds 063-065

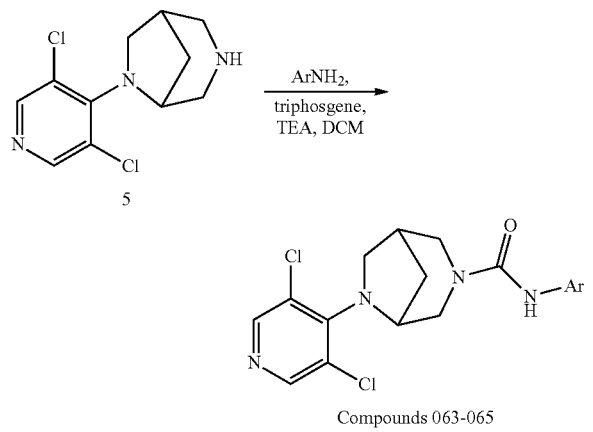

To a solution of ArNH₂ (0.15 mmol) and Et₃N (76 mg, 0.75 mmol) in DCM (10 mL) was added triphosgene (25 mg, 0.08 mmol). After the mixture stirring for 2 min, compound 5 (40 mg, 0.15 mmol) was added and stirred at rt for 30 min. The solvent was removed and the residue was purified by prep-HPLC (FA) to give the desired product.

General Procedure M:

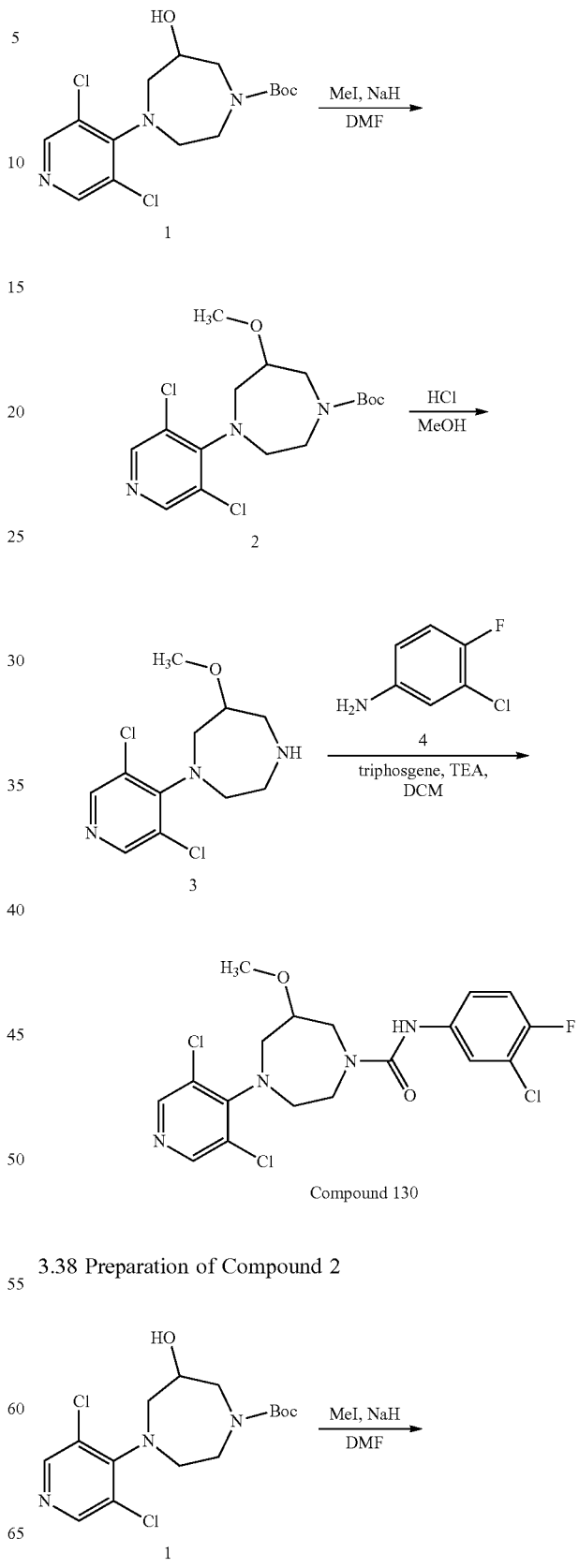

3.38 Preparation of Compound 2

-continued

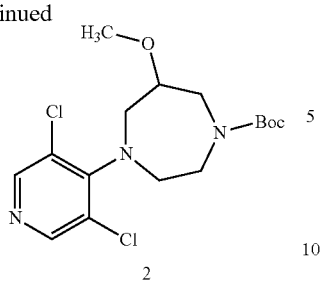

2

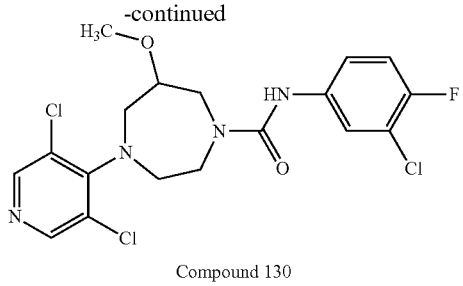

Compound 130

To a solution of compound 1 (100 mg, 0.28 mmol) in DMF (10 mL) was added NaH (17 mg, 0.42 mmol) at 0° C. The resulting mixture was stirred at rt for 15 min. Then MeI (78 mg, 0.55 mmol) was added and the mixture was stirred for 4 h. The mixture was quenched with water, and extracted with EA. The combined organic layers were dried over $Na_2SO_4$ and concentrated in vacuo. Then the residue was purified by column chromatography (PE:EA=15:1) to give compound 2 (91 mg, 87%). LCMS: 376 (M+1).

3.39 Preparation of Compound 3

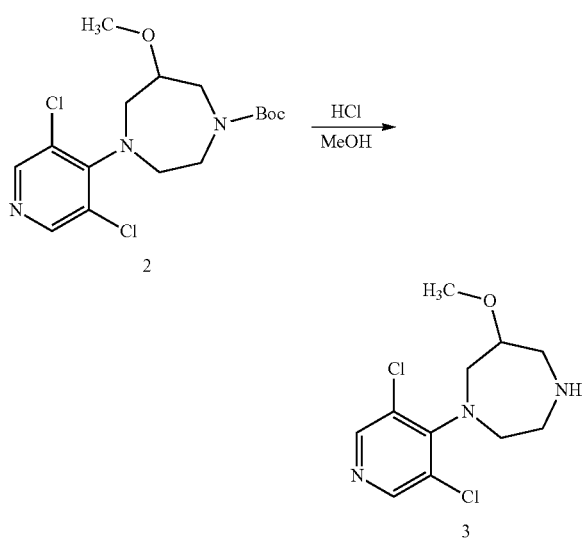

To a solution of Compound 2 (91 mg, 0.24 mmol) in MeOH (10 mL) was added HCl/MeOH (5 mL). The resulting mixture was stirred at 26° C. for 5 h. Then the mixture was concentrated under vacuum to give the crude product, used directly in next step.

3.40 Preparation of Compound 130

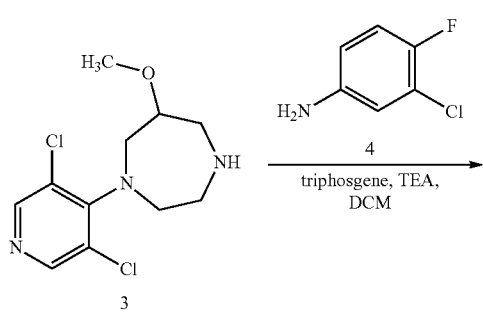

To a solution of compound 4 (41.3 mg, 0.32 mmol) in DCM (10 mL) was added TEA (161 mg, 1.6 mmol) and triphosgene (57.6 mg, 0.19 mmol). The resulting mixture was stirred for 15 min. Then, compound 3 (100 mg, 0.32 mmol) was added and the mixture was stirred for another 0.5 h. The mixture was concentrated in vacuo. The residue was purified by prep-HPLC to give the compound 130 (42.09 mg, 29%). LCMS: 447/449 (M+1).

Example: HBV Assembly Assay

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 mM, and the assembly reactions are initiated by addition of NaCl. The reaction is allowed to continue for 1 hour at room temperature.

To determine the effect on capsid assembly, each test compound is initially screened at least 4 different concentrations in duplicates. Primary hits are compounds that show activity in the assembly assay at 10 uM. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

Selected compounds of the invention were assayed in the HBV assembly assay, as described above. The assembly assay was conducted in 96-well plate format. The assembly reactions were carried out in 50 mM Hepes buffer, pH 7.5 and 150 mM NaCl. The compounds were pre-incubated with the HBV CA protein for 15 mM, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 5 different concentrations: about 30 µM, 10 µM, 3 µM, 1 µM, and 0.3 µM in duplicates. Primary hits were compounds that show >50% activity in the assembly assay at about 10 µM and a representative group of these active compounds is shown in Table 2.

TABLE 2

HBV assembly assay

| Compound | Activity |
|---|---|
| 004 | + |
| 005 | + |
| 010 | + |
| 011 | + |
| 044 | + |
| 045 | + |
| 047 | + |
| 055 | + |
| 056 | + |
| 091 | + |
| 092 | + |
| 097 | + |
| 098 | + |
| 099 | + |
| 100 | + |
| 107 | + |
| 108 | + |
| 109 | + |
| 110 | + |
| 120 | + |

('+' indicates >50% activity at about 10 µM)

TABLE 3

Compounds in the following table have HBV assembly potency ($IC_{50}$ < 20 µM).

| Compound | Activity |
|---|---|
| 091 | + |
| 092 | + |
| 107 | + |
| 108 | + |
| 109 | + |
| 110 | + |

Example: Dot-Blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Selected compounds, which were shown to be active in the HBV assembly assay, were tested for their activity and toxicity in cellular assay. In the first anti-viral assay, the ability of compounds to inhibit HBV replication in an HBV-producing hepatoma cell line using the dot-blot method was evaluated.

Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results are illustrated in Table 4.

Cytotoxicity ($CC_{50}$) was measured in this same HepG2-2.2.15 cell line using a CellTiter Blue-based cytotoxicity assay employed as recommended by manufacturer (Promega). All compounds in Table 4 demonstrated low toxicity at 5 µM.

TABLE 4

"Activity" represents activity in dot-blot-assay

| Compound | Activity |
|---|---|
| 005 | + |
| 010 | + |

TABLE 4-continued

"Activity" represents activity in dot-blot-assay

| Compound | Activity |
|---|---|
| 011 | + |
| 025 | + |
| 040 | + |
| 041 | + |
| 043 | + |
| 044 | + |
| 045 | + |
| 047 | + |
| 049 | + |
| 056 | + |
| 065 | + |
| 077 | + |
| 087 | + |
| 092 | + |
| 097 | + |
| 099 | + |
| 100 | + |
| 107 | + |
| 109 | + |
| 115 | + |
| 120 | + |
| 121 | + |
| 126 | + |
| 129 | + |
| 130 | + |
| 131 | + |
| 135 | + |

('+' indicates >50% activity at 10 μM)

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

I claim:

1. A compound of Formula Ia:

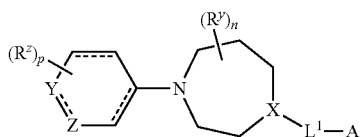

Ia or a pharmaceutically acceptable salt thereof,
wherein
a ═══ line denotes a double bond;
X is C or N;
each Y and Z are independently selected from N and C;
$L^1$ is —C(O)$NR^1$—, —$SO_2NR^1$—, —C(O)—, —C(O)O—, or $C_{1-4}$ alkyl;
A is $C_{1-6}$ alkyl, -$(L^2)_q$-$OR^3$, $C_{3-10}$ cycloalkyl, $C_{3-10}$ heterocycloalkyl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl), wherein A is optionally substituted with one or more occurrences of $R^x$;
$R^x$ is independently, at each occurrence, halo, —CN, —$NO_2$, —$C_{1-6}$ haloalkyl, —$C_{1-6}$ dihaloalkyl, —$C_{1-6}$ trihaloalkyl, -$(L^2)_q$-C(═O)$R^2$, -$(L^2)_q$$CO_2R^3$, or -$(L^2)_q$-C(═O)N($R^3$)$_2$;

$R^y$ is independently, at each occurrence, $C_{1-6}$ alkyl, halo, —CN, —$NO_2$, -$(L^2)_q$-$OR^3$, -$(L^2)_q$-$SR^2$, -$(L^2)_q$-S(═O)$R^2$, -$(L^2)_q$-S(═O)$_2R^2$, -$(L^2)_q$-NHS(═O)$_2R^2$, -$(L^2)_q$-C(═O)$R^2$, -$(L^2)_q$-OC(═O)$R^2$, -$(L^2)_q$$CO_2R^3$, -$(L^2)_q$-$OCO_2R^3$, -$(L^2)_q$-N($R^3$)$_2$, -$(L^2)_q$-C(═O)N($R^3$)$_2$, -$(L^2)_q$-OC(═O)N($R^3$)$_2$, -$(L^2)_q$-NHC(═O)NH($R^3$), -$(L^2)_q$-NHC(═O)$R^2$, -$(L^2)_q$-NHC(═O)$OR^2$, -$(L^2)_q$-C(OH)($R^3$)$_2$, -$(L^2)_q$C(NH$_2$)($R^3$)$_2$, —$C_{1-6}$ haloalkyl, —$C_{1-6}$ dihaloalkyl, —$C_{1-6}$ trihaloalkyl, —$C_{3-7}$ cycloalkyl, —$C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

or two $R^y$ groups on adjacent carbon atoms are taken together to form a fused ring; or two $R^y$ groups on non-adjacent carbon atoms are taken together to form a bridge of a bridged bicyclic group;

$R^z$ is independently, at each occurrence, $C_{1-6}$ alkyl, halo, —CN, —$NO_2$, -$(L^2)_q$-$OR^3$, -$(L^2)_q$-$SR^2$, -$(L^2)_q$-S(═O)$R^2$, -$(L^2)_q$-S(═O)$_2R^2$, -$(L^2)_q$-NHS(═O)$_2R^2$, -$(L^2)_q$-C(═O)$R^2$, -$(L^2)_q$- OC(═O)$R^2$, -$(L^2)_q$$CO_2R^3$, -$(L^2)_q$-$OCO_2R^3$, -$(L^2)_q$-N($R^3$)$_2$, -$(L^2)_q$-C(═O)N($R^3$)$_2$, -$(L^2)_q$-OC(═O)N($R^3$)$_2$, -$(L^2)_q$-NHC(═O)NH($R^3$), -$(L^2)_q$-NHC(═O)$R^2$, -$(L^2)_q$-NHC(═O)$OR^2$, -$(L^2)_q$-C(OH)($R^3$)$_2$, -$(L^2)_q$C(NH$_2$)($R^3$)$_2$, —$C_{1-6}$ haloalkyl, —$C_{1-6}$ dihaloalkyl, —$C_{1-6}$ trihaloalkyl, $C_{3-7}$ cycloalkyl, $C_{3-10}$ heterocycloalkyl, aryl, heteroaryl, —$C_{1-4}$ alkylene-($C_{3-7}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

$L^2$ is independently, at each occurrence, a bivalent radical selected from —($C_{1-3}$ alkylene), —($C_{3-7}$ cycloalkylene)-, —($C_{1-3}$ alkylene)$_q$-O—($C_{1-3}$ alkylene)$_q$-, or —($C_{1-3}$ alkylene)$_q$-NH—($C_{1-3}$ alkylene)$_q$-;

$R^1$ is H or $C_{1-6}$-alkyl;

$R^2$ is $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

each $R^3$ is independently, at each occurrence, H, $C_{1-6}$ alkyl, —$C_{1-6}$ haloalkyl, —$C_{1-6}$ dihaloalkyl, —$C_{1-6}$ trihaloalkyl, $C_{3-10}$ cycloalkyl, $C_{3-10}$ heterocycloalkyl, aryl, heteroaryl, —$C_{1-4}$ alkylene-($C_{3-10}$ cycloalkyl), —$C_{1-4}$ alkylene-($C_{3-10}$ heterocycloalkyl), —$C_{1-4}$ alkylene-(aryl), or —$C_{1-4}$ alkylene-(heteroaryl);

n is 0, 1, 2, or 3;

p is 1, 2, or 3; and q is 0 or 1.

2. The compound of claim 1, or a pharmaceutically acceptable salt thereof, wherein Y is N, and Z is C.

3. The compound of claim 1, or a pharmaceutically acceptable salt thereof, wherein $L^1$ is —C(O)$NR^1$— or —$SO_2NR^1$—.

4. The compound of claim 1, or a pharmaceutically acceptable salt thereof, wherein $L^1$ is —C(O)NH—.

5. The compound of claim 1, or a pharmaceutically acceptable salt thereof, wherein $R^x$ is independently, at each occurrence, halo.

6. The compound of claim 1, or a pharmaceutically acceptable salt thereof, wherein $R^y$ is $C_{1-6}$ alkyl, halo, -$(L^2)_q$-$OR^3$, -$(L^2)_q$$CO_2R^3$, or —$C_{1-4}$ alkylene-(aryl).

7. The compound of claim 1, or a pharmaceutically acceptable salt thereof, wherein two $R^y$ groups on adjacent carbon atoms are taken together to form a fused ring, and wherein the ring is $C_{3-10}$-cycloalkyl or phenyl.

8. The compound of claim 1, or a pharmaceutically acceptable salt thereof, wherein two $R^y$ groups on non-adjacent carbon atoms are taken together to form a bridge of a bridged bicyclic group, and wherein the bridge is a $C_{1-3}$-alkyl chain.

9. The compound of claim 1, or a pharmaceutically acceptable salt thereof, wherein $R^z$ is independently, at each occurrence, $C_{1-6}$ alkyl, halo, $-(L^2)_q-OR^3$, or $C_{3-7}$ cycloalkyl.

10. The compound of claim 1, or a pharmaceutically acceptable salt thereof, wherein $R^z$ is independently, at each occurrence, halo or $C_{1-6}$ alkyl.

11. A compound selected from:

002
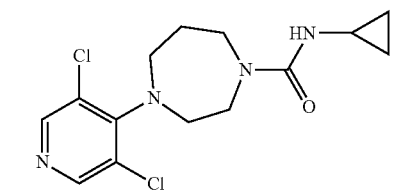

003
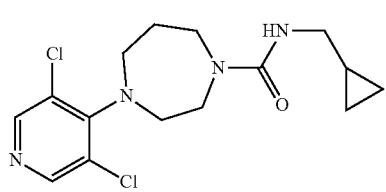

006
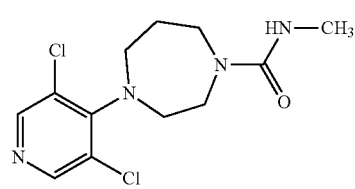

007
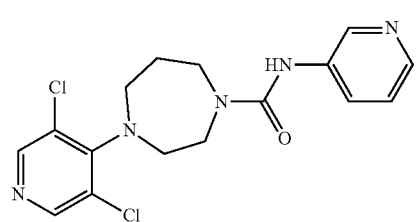

008
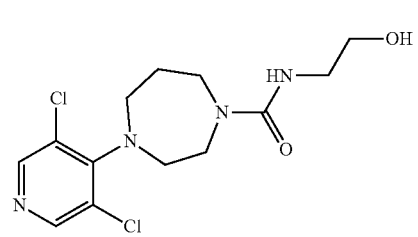

009
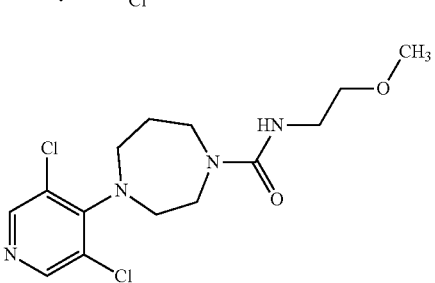

-continued

014
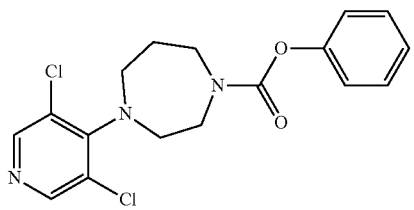

015
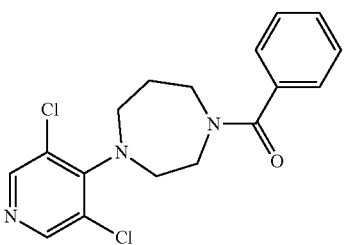

016
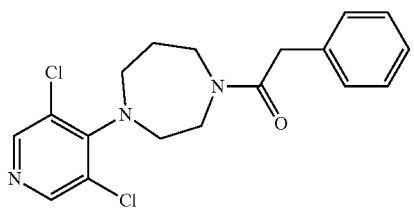

017
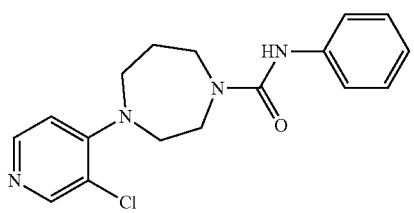

018
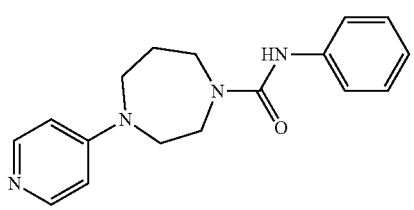

019
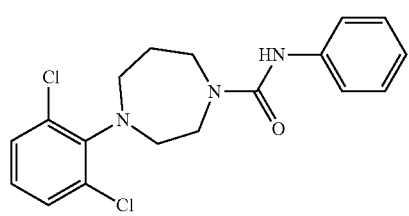

020
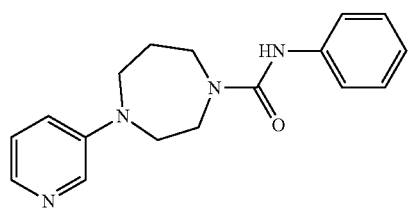

021
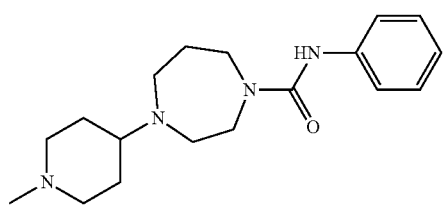
024
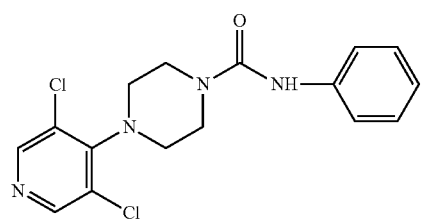
031
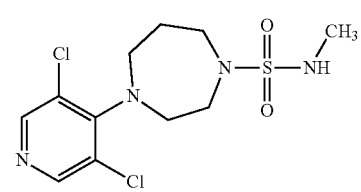
032
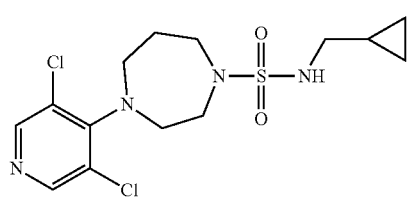
033
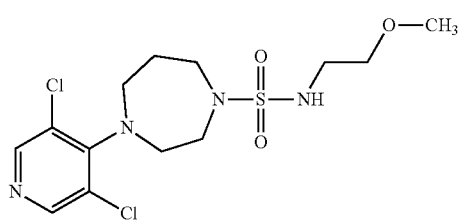
034
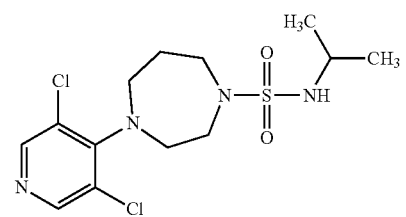
035
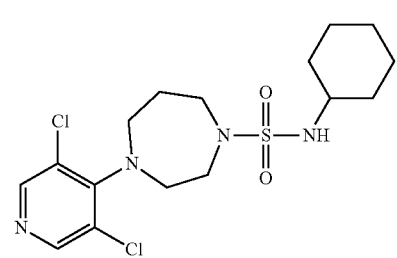
038
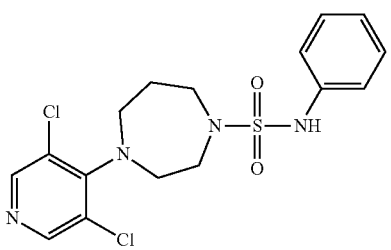
039
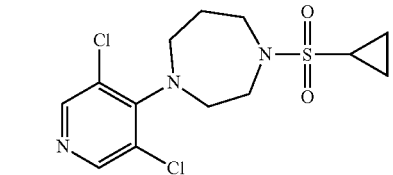
050
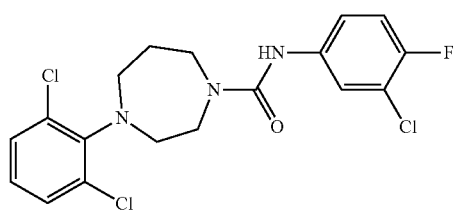
054
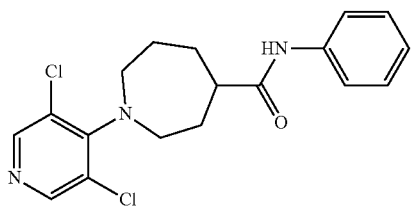
057
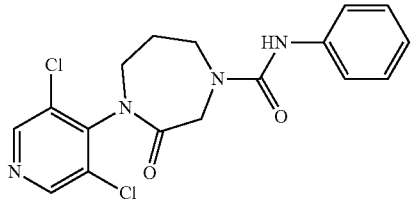
060
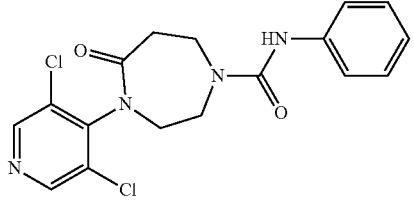
063
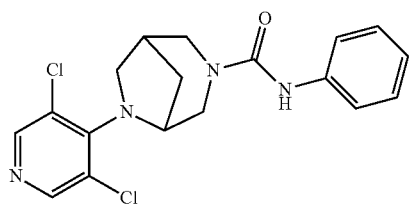

066
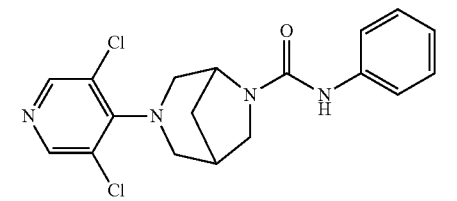
069
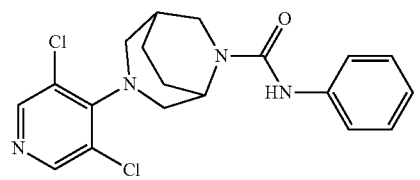
070
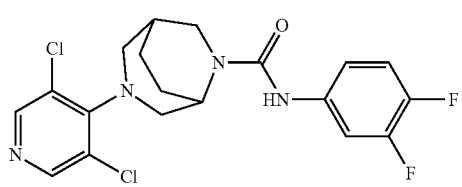
071
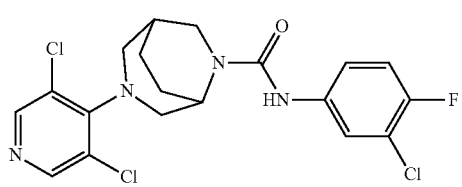
072
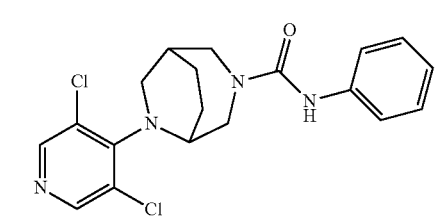
073
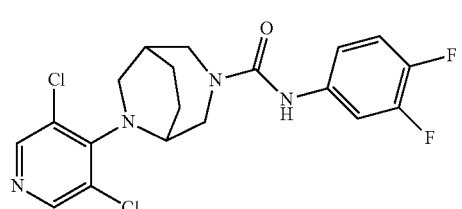
074
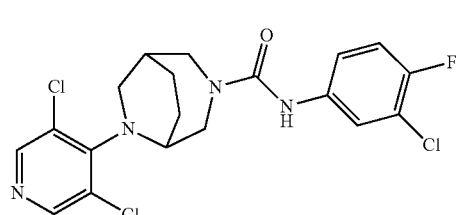
075
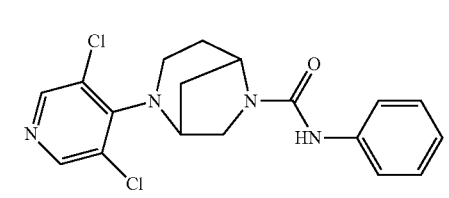
076
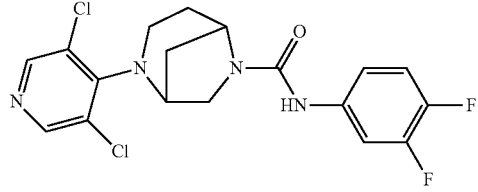
077
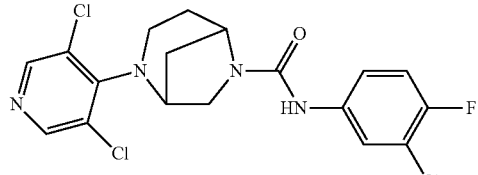
078
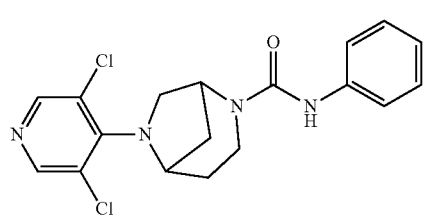
079
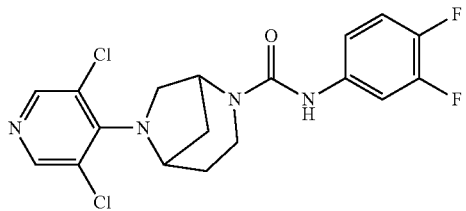
080
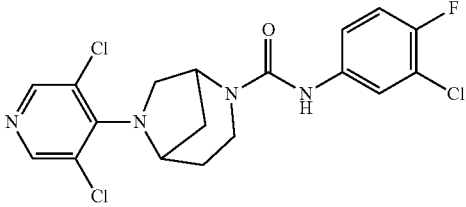
081
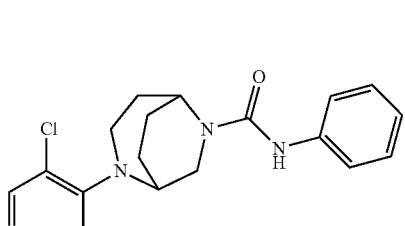
082
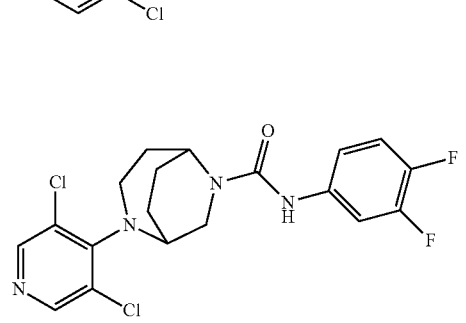

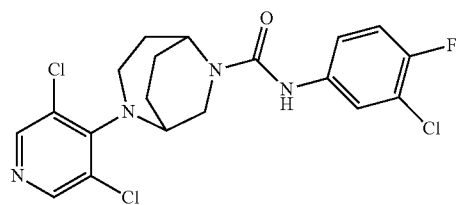
083
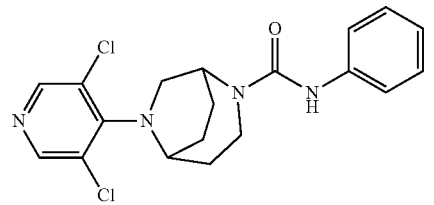
084
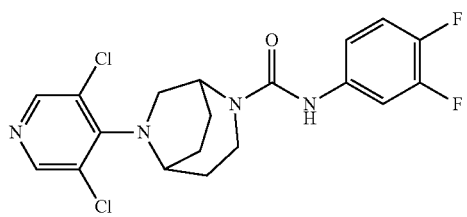
085
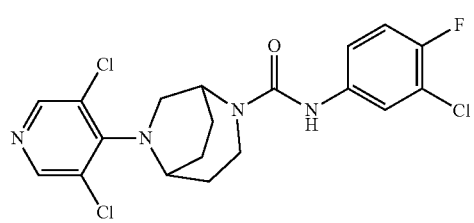
086
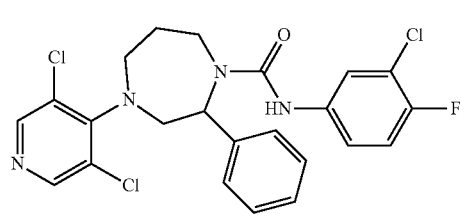
090
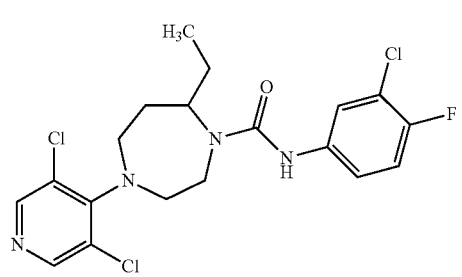
093
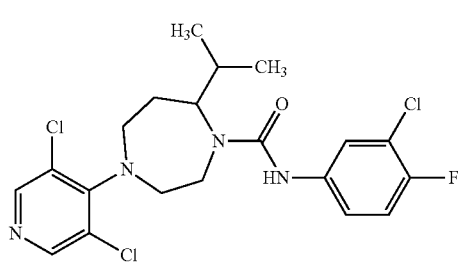
094
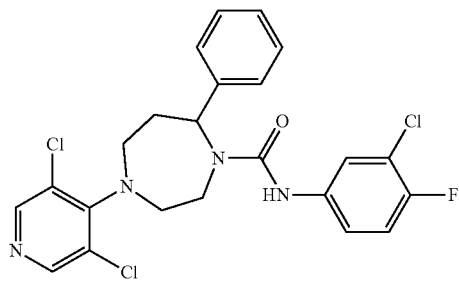
095
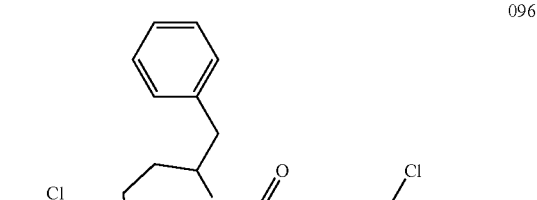
096
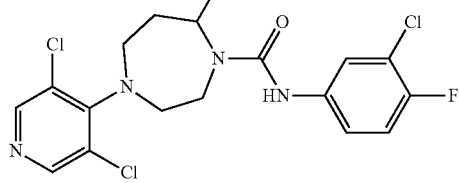
104
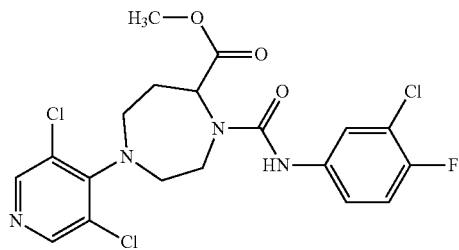
105
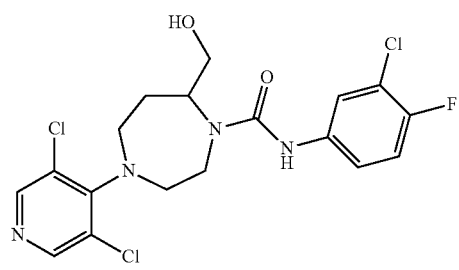
106
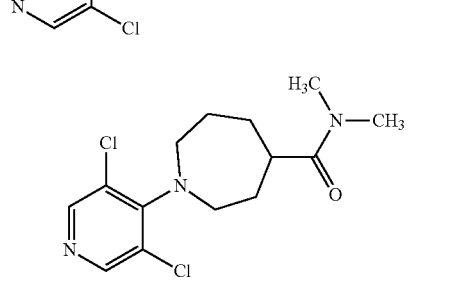
111

112 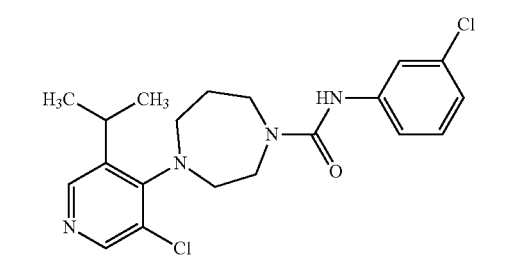
113 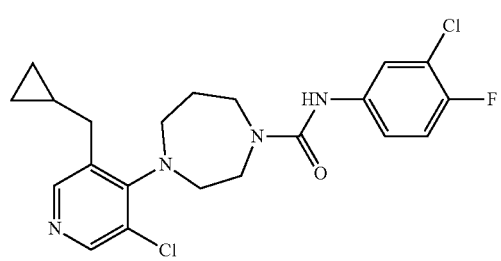
114 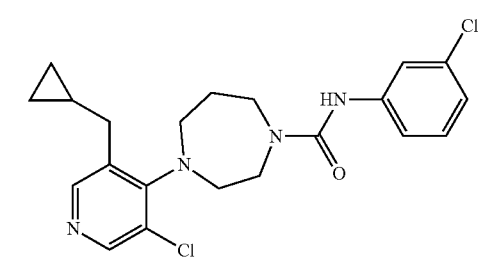
115 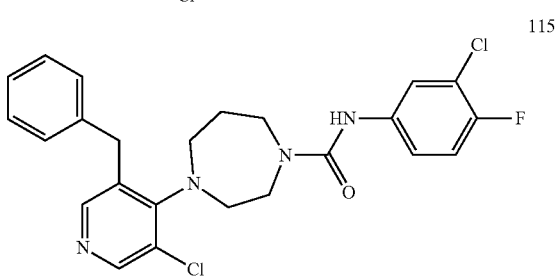
116 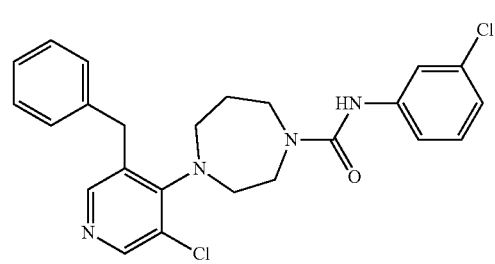
117 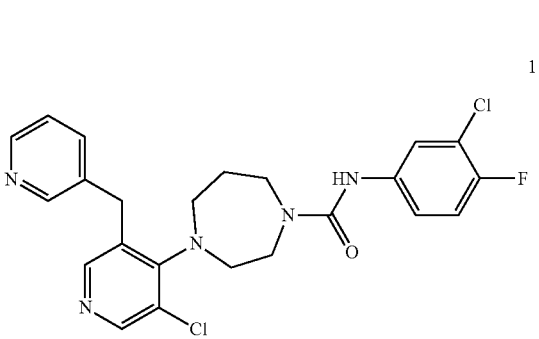
118 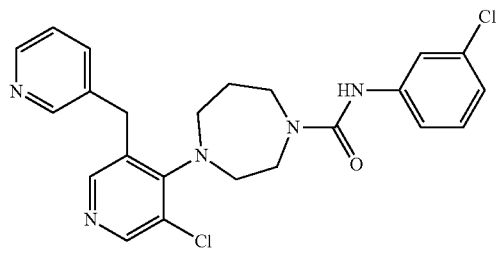
119 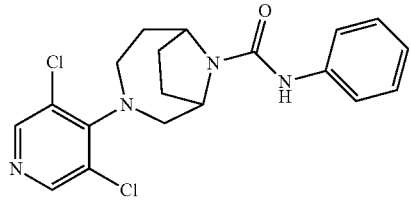
126 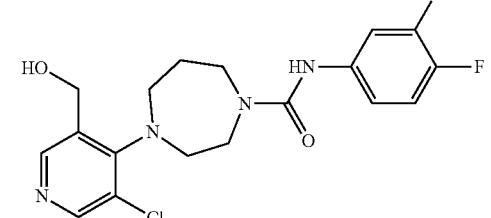
127 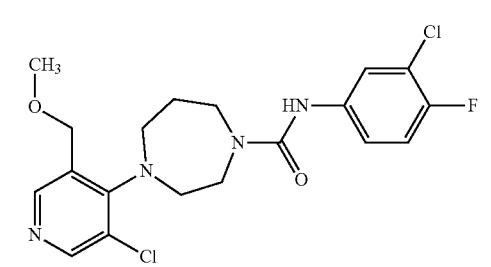
128 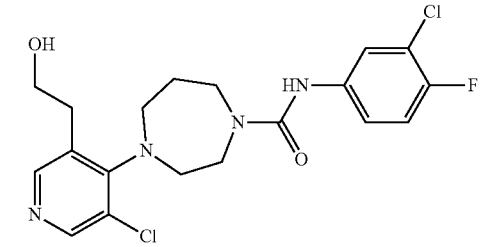
129 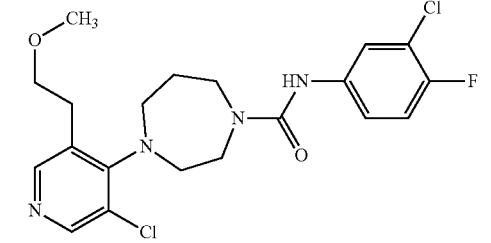
or a pharmaceutically acceptable salt thereof.
12. A pharmaceutical composition comprising a compound of claim 1, or a pharmaceutically acceptable salt thereof, together with a pharmaceutically acceptable carrier.

13. A method of treating an HBV infection in an individual in need thereof, comprising administering to the individual a therapeutically effective amount of a compound according to claim 1.

14. The method of claim 13, further comprising administering to the individual at least one additional therapeutic agent selected from the group consisting of a HBV polymerase inhibitor, interferon, viral entry inhibitor, viral maturation inhibitor, BAY 41-4109, reverse transcriptase inhibitor, a TLR-agonist, AT-61 ((E)-N-(1-chloro-3-oxo-1-phenyl-3(piperidine-1-yl)prop-1-en-2-yl)benzamide), and AT-130 ((E)-N-(1-bromo-1-(2-methoxyphenyl)-3-oxo-3-(piperidine-1-yl)prop-1en-2-yl)-4-nitrobenzamide), and a combination thereof.

15. The method of claim 14, wherein the therapeutic agent is a reverse transcriptase inhibitor, and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

16. The method of claim 14, wherein the TLR agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)-propyl]amino}methyl)phenyl]acetate).

17. The method of claim 14, wherein the therapeutic agent is an interferon, and wherein the interferon is any interferon, which may be optionally pegylated.

18. The method of claim 17, wherein the interferon is interferon alpha (IFN-α), interferon beta (IFN-β), interferon lambda (IFN-λ), interferon gamma (IFN-γ), interferon-alpha-2a, interferon-alpha-2b, interferon-alpha-n1, pegylated interferon-alpha-2a, or pegylated interferon-alpha-2b.

* * * * *